United States Patent
Dooley et al.

(10) Patent No.: US 10,561,740 B2
(45) Date of Patent: *Feb. 18, 2020

(54) PREPARATION OF THERAPEUTIC EXOSOMES USING MEMBRANE PROTEINS

(71) Applicant: Codiak BioSciences, Inc., Cambridge, MA (US)

(72) Inventors: Kevin P. Dooley, Boston, MA (US); Rane A. Harrison, Belmont, MA (US); Russell E. McConnell, Brighton, MA (US); Ke Xu, Sudbury, MA (US); Damian J. Houde, Plymouth, MA (US); Nikki Ross, Cambridge, MA (US); Sonya Haupt, Cambridge, MA (US); John D. Kulman, Belmont, MA (US); Douglas E. Williams, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/231,012

(22) Filed: Dec. 21, 2018

(65) Prior Publication Data

US 2019/0117792 A1    Apr. 25, 2019

Related U.S. Application Data

(63) Continuation of application No. 16/112,547, filed on Aug. 24, 2018, now Pat. No. 10,195,290.

(60) Provisional application No. 62/656,956, filed on Apr. 12, 2018, provisional application No. 62/550,543, filed on Aug. 25, 2017.

(51) Int. Cl.
*A61K 47/69* (2017.01)
*C07K 14/705* (2006.01)
*C07K 14/755* (2006.01)
*C07K 16/28* (2006.01)
*A61K 38/00* (2006.01)

(52) U.S. Cl.
CPC .... *A61K 47/6917* (2017.08); *C07K 14/70503* (2013.01); *C07K 14/70596* (2013.01); *C07K 14/755* (2013.01); *C07K 16/2851* (2013.01); *A61K 38/00* (2013.01); *C07K 2317/55* (2013.01); *C07K 2317/622* (2013.01); *C07K 2319/00* (2013.01); *C07K 2319/30* (2013.01); *C07K 2319/43* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 5,747,660 A | 5/1998 | Orlicky | |
| 9,518,125 B2 | 12/2016 | Yong et al. | |
| 10,195,290 B1 | 2/2019 | Dooley | |
| 2004/0049010 A1 | 3/2004 | Warren et al. | |
| 2005/0119215 A1 | 6/2005 | Al-Mahmood et al. | |
| 2013/0156801 A1 | 6/2013 | Bond et al. | |
| 2014/0179006 A1 | 6/2014 | Zhang | |
| 2015/0290343 A1 | 10/2015 | Lotvall et al. | |
| 2015/0301058 A1 | 10/2015 | Schettini et al. | |

FOREIGN PATENT DOCUMENTS

| | | |
|---|---|---|
| WO | WO2001/093836 A3 | 10/2002 |
| WO | WO-2007053648 A2 | 5/2007 |
| WO | WO2007/126386 A1 | 11/2007 |
| WO | WO2012/048372 A1 | 4/2012 |
| WO | WO-2014138793 A1 | 9/2014 |
| WO | WO2016/057755 A1 | 4/2016 |
| WO | WO2016/077639 A2 | 5/2016 |
| WO | WO-2017117585 A1 | 7/2017 |
| WO | WO2017/161010 A1 | 9/2017 |
| WO | WO-2018226758 A2 | 12/2018 |
| WO | WO-2019040920 A1 | 2/2019 |

OTHER PUBLICATIONS

Bellavia, D. et al., "Interleukin 3-receptor targeted exosomes inhibit in vitro and in vivo Chronic Myelogenous Leukemia cell growth," Theranostics, 2017, vol. 7, No. 5, pp. 1333-1345.
Kooijmans, S.A.A. et al., "Modulation of tissue tropism and biological activity of exosomes and other extracellular vesicles: New nanotools for cancer treatment," Pharmacological Research, Sep. 2016, vol. 111, pp. 487-500.
Lai, R.C. et al. "Mesenchymal Stem Cell Exosome: a Novel Stem Cell Based Therapy for Cardiovascular Disease," Regenerative Medicine, Jul. 2011, vol. 6. No. 4, pp. 481-492.
Moss, M. et al. "Shedding of Membrane Proteins by ADAM Family Proteases." Essays in Biochemistry, Oct. 2002, vol. 38, pp. 141-154.
PCT International Search Report and Written Opinion, PCT Application No. PCT/US2018/048026, dated Oct. 30, 2018, 23 pages.
Yang, J. et al., "Exosome Mediated Delivery of miR-124 Promotes Neurogenesis after Ischemia," Molecular Therapy Nucleic Acids, Jun. 2017, vol. 7, pp. 278-287.

*Primary Examiner* — Daniel C Gamett

(57) ABSTRACT

The present invention relates to methods of preparing a therapeutic exosome using a protein newly-identified to be enriched on the surface of exosomes. Specifically, the present invention provides methods of using the proteins for affinity purification of exosomes. It also provides methods of localizing a therapeutic peptide on exosomes, and targeting exosomes to a specific organ, tissue or cell by using the proteins. The methods involve generation of surface-engineered exosomes that include one or more of the exosome proteins at higher density, or a variant or a fragment of the exosome protein.

15 Claims, 45 Drawing Sheets

Figure 1:
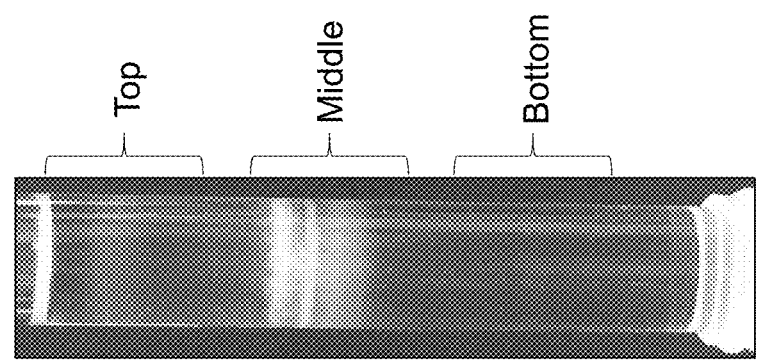

Specification includes a Sequence Listing.

Figure 3

PTGFRN (Q9P2B2)

Modifications
C: Carbamidomethyl (C)
D: Deamidated (Q, N)
O: Oxidation (M)

Figure 4

IGSF8 (Q969P0)

Modifications
C: Carbamidomethyl (C)
D: Deamidated (Q)

Figure 5

BSG (P35613)

```
                    1          51         101        151        201        251        301        351    385

Modifications                                              D     C C
P35613          MAAALFVLLG FALLGTHGAS GAAGFVQAPL SQQMVGGSV ELHCEAVGSP VPEIQWWFEG QGPNTCSQL MGARLDRVH IHATTHQHAA STISIDTLVE
                                                                                    C
Modifications                     C    G                      D  C C                      C                           O
P35613          HPIGTTECPA SSDPDRNHHI RAPRYRGEA QAVYILHPG LVTTVEDLG SKILIESLN DSRIEVTCHR VLKGYYISE ERLFCQKTEE KTHSSQVRSS
                                C  G
Modifications       C  G  G                        D  G  C                     G                          O
P35613          YSCVELPKPH GTAMIQLEEP PRVKAYESSE MDREETAML VCKSESVPPV TDWYYKITD SKDALNRGG ESRRYSSGG GESLNLESL NRGADPSGYE
                                                                                                  O
Modifications
P35613          CRGTSSGSR QRIILKVUS HLAALWPFLG IVAEVLVLVT IIFIYEKRR FKDLNEHRA GSRPLKSGCQ HGNDLGENPR QRNSS
```

Modifications

C: Carbamidomethyl (C)
D: Deamidated (N, Q)
O: Oxidation (M)

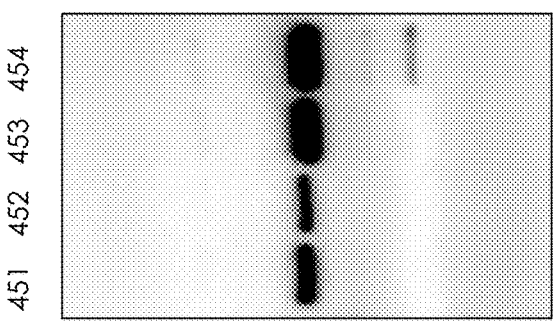
Figure 14C
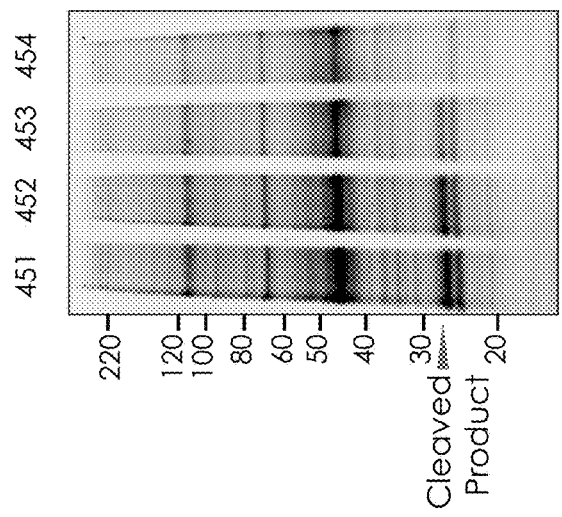
Figure 14B
Figure 14A

Figure 21

PTGFRN Ectodomain Binding Partners (pH 7.4)

| Rank | Name | A Score |
|---|---|---|
| 1 | LGALS1 | 144.801 |
| 2 | FCN1 | 20.788 |
| 3 | MGAT4B | 9.738 |

PTGFRN Ectodomain Binding Partners (pH 5.6)

| Rank | Name | A Score |
|---|---|---|
| 1 | EPN1 | 112.017 |
| 2 | LGALS1 | 82.059 |
| 3 | ZCCHC8 | 29.974 |
| 4 | MGAT4B | 13.778 |
| 5 | FCN1 | 10.605 |

Figure 31

No. of Peptide Spectrum Matches (PSMs)

| Gene Name | HEK | HT1080 | K562 | MB231 | Raji | MSC* |
|---|---|---|---|---|---|---|
| PTGFRN | 197 | 151 | 37 | 0 | 0 | 111 |
| IGSF8 | 61 | 19 | 31 | 5 | 10 | 52 |
| IGSF3 | 5 | 3 | 14 | 0 | 0 | 0 |
| BSG | 91 | 60 | 62 | 24 | 48 | 82 |
| SLC3A2 | 163 | 117 | 59 | 117 | 95 | 35 |
| ITGB1 | 74 | 400 | 82 | 252 | 95 | 319 |
| CD81 | 34 | 21 | 2 | 9 | 9 | 48 |
| CD9 | 21 | 6 | 0 | 31 | 0 | 41 |

*Performed in a separate experiment

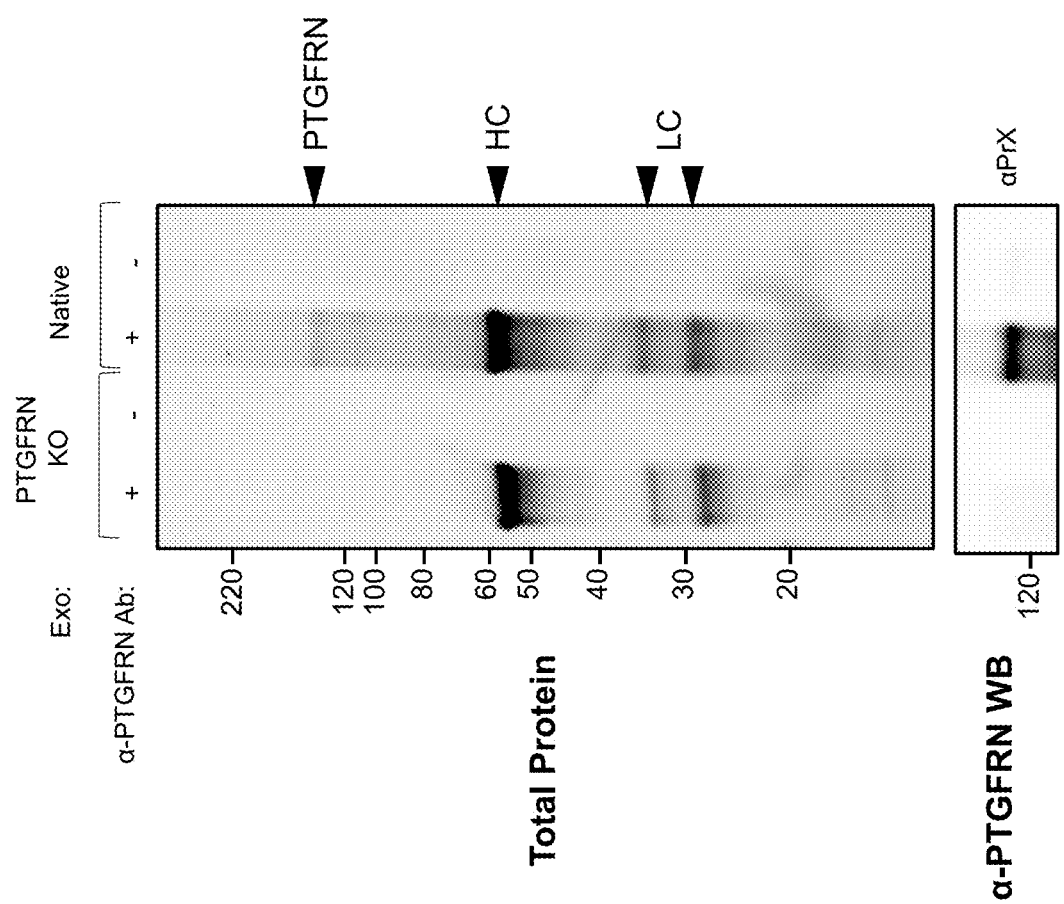
Figure 35A
Figure 35B

Figure 36A

Figure 36B scFab-αCLEC9A-PTGFRN-mEGFP-FLAG

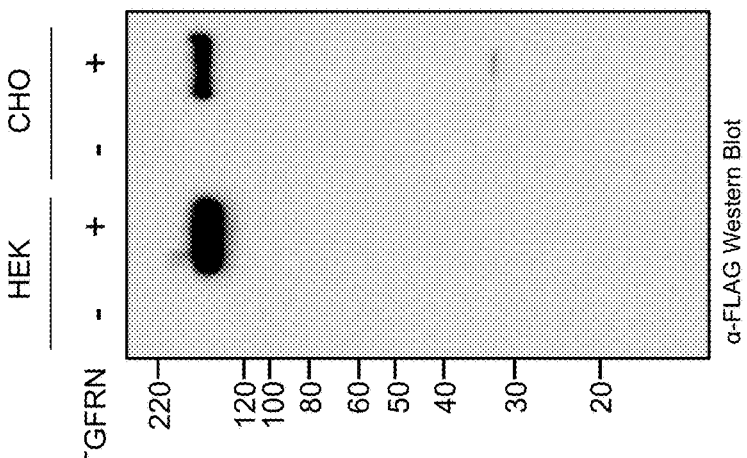
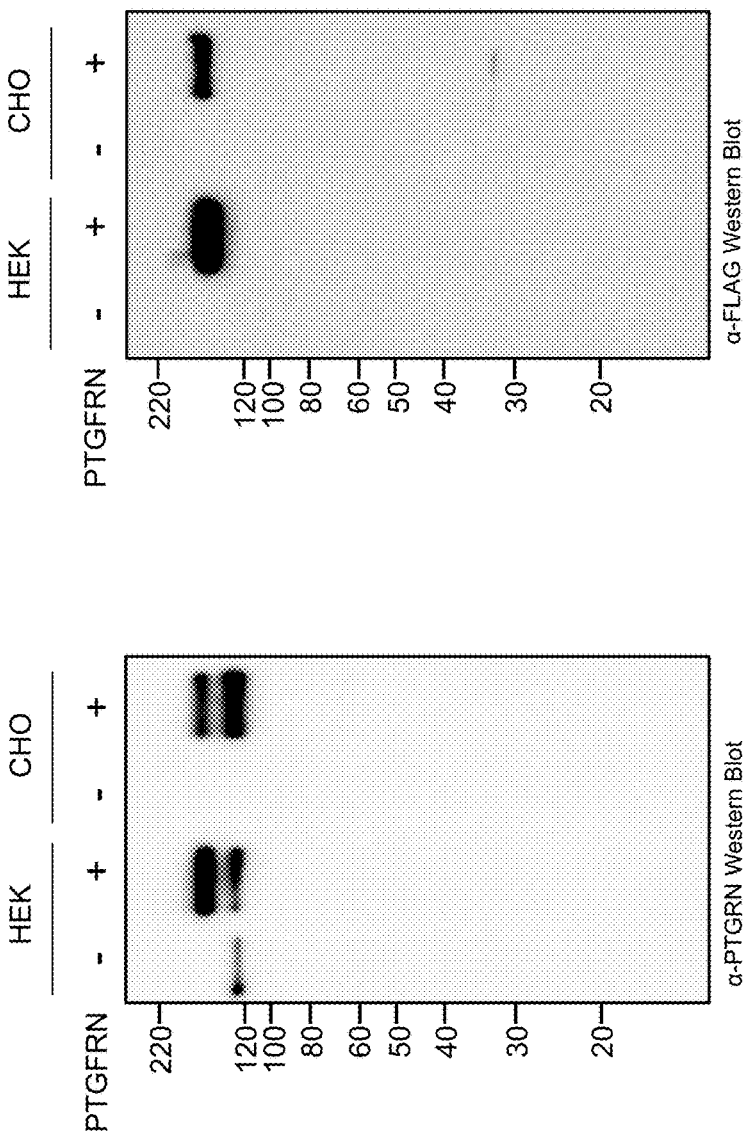
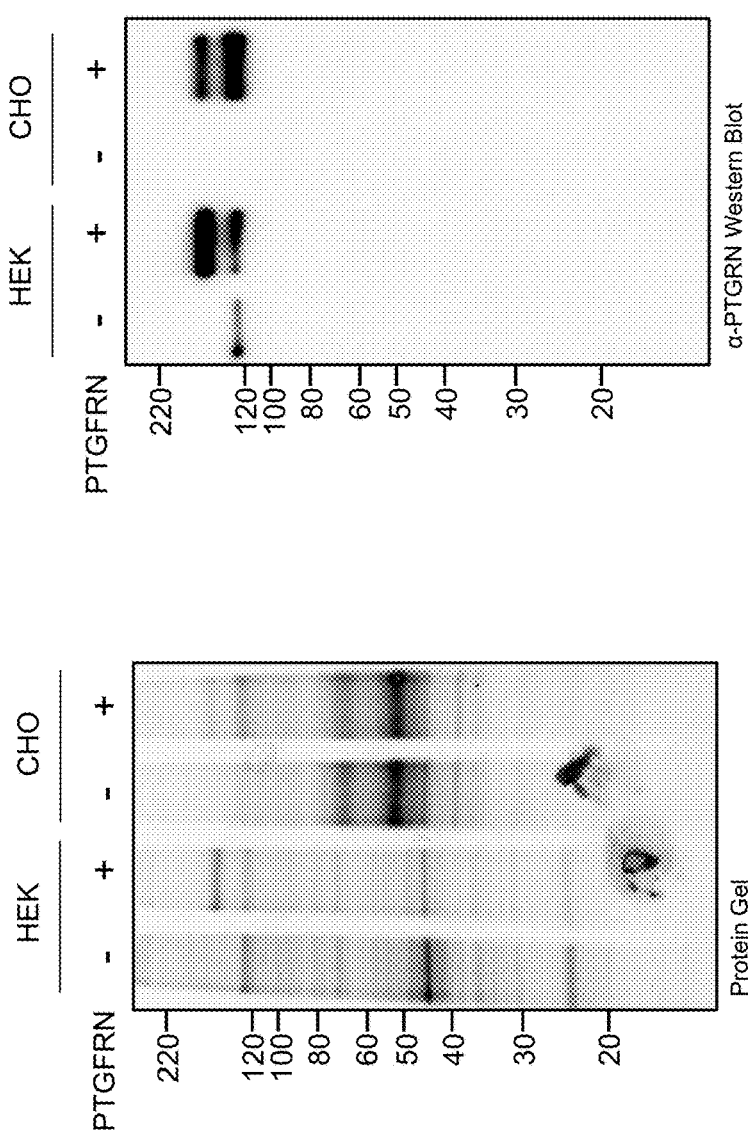
Figure 43C
Figure 43B
Figure 43A

SEQUENCE LISTING

```
<160> NUMBER OF SEQ ID NOS: 46

<210> SEQ ID NO 1
<211> LENGTH: 879
<212> TYPE: PRT
<213> ORGANISM: Homo sapiens

<400> SEQUENCE: 1

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190
```

```
Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605
```

```
Asp Gln Asp Ser Val Val Lys Leu Glu Asn Trp Thr Asp Ala Ser Arg
    610                 615                 620
Val Asp Gly Val Val Leu Glu Lys Val Gln Glu Asp Glu Phe Arg Tyr
625                 630                 635                 640
Arg Met Tyr Gln Thr Gln Val Ser Asp Ala Gly Leu Tyr Arg Cys Met
                    645                 650                 655
Val Thr Ala Trp Ser Pro Val Arg Gly Ser Leu Trp Arg Glu Ala Ala
                660                 665                 670
Thr Ser Leu Ser Asn Pro Ile Glu Ile Asp Phe Gln Thr Ser Gly Pro
            675                 680                 685
Ile Phe Asn Ala Ser Val His Ser Asp Thr Pro Ser Val Ile Arg Gly
        690                 695                 700
Asp Leu Ile Lys Leu Phe Cys Ile Ile Thr Val Glu Gly Ala Ala Leu
705                 710                 715                 720
Asp Pro Asp Asp Met Ala Phe Asp Val Ser Trp Phe Ala Val His Ser
                    725                 730                 735
Phe Gly Leu Asp Lys Ala Pro Val Leu Leu Ser Ser Leu Asp Arg Lys
                740                 745                 750
Gly Ile Val Thr Thr Ser Arg Arg Asp Trp Lys Ser Asp Leu Ser Leu
            755                 760                 765
Glu Arg Val Ser Val Leu Glu Phe Leu Leu Gln Val His Gly Ser Glu
        770                 775                 780
Asp Gln Asp Phe Gly Asn Tyr Tyr Cys Ser Val Thr Pro Trp Val Lys
785                 790                 795                 800
Ser Pro Thr Gly Ser Trp Gln Lys Glu Ala Glu Ile His Ser Lys Pro
                    805                 810                 815
Val Phe Ile Thr Val Lys Met Asp Val Leu Asn Ala Phe Lys Tyr Pro
                820                 825                 830
Leu Leu Ile Gly Val Gly Leu Ser Thr Val Ile Gly Leu Leu Ser Cys
            835                 840                 845
Leu Ile Gly Tyr Cys Ser Ser His Trp Cys Cys Lys Lys Glu Val Gln
        850                 855                 860
Glu Thr Arg Arg Glu Arg Arg Arg Leu Met Ser Met Glu Met Asp
865                 870                 875

<210> SEQ ID NO 2
<211> LENGTH: 731
<212> TYPE: PRT
<213> ORGANISM: Homo sapiens

<400> SEQUENCE: 2

Pro Ser Ala Arg Pro Pro Ser Leu Ser Leu Arg Glu Gly Glu Pro
1               5                   10                  15
Phe Glu Leu Arg Cys Thr Ala Ala Ser Ala Ser Pro Leu His Thr His
                20                  25                  30
Leu Ala Leu Leu Trp Glu Val His Arg Gly Pro Ala Arg Arg Ser Val
            35                  40                  45
Leu Ala Leu Thr His Glu Gly Arg Phe His Pro Gly Leu Gly Tyr Glu
        50                  55                  60
Gln Arg Tyr His Ser Gly Asp Val Arg Leu Asp Thr Val Gly Ser Asp
65                  70                  75                  80
Ala Tyr Arg Leu Ser Val Ser Arg Ala Leu Ser Ala Asp Gln Gly Ser
                85                  90                  95
Tyr Arg Cys Ile Val Ser Glu Trp Ile Ala Glu Gln Gly Asn Trp Gln
                100                 105                 110
```

```
Glu Ile Gln Glu Lys Ala Val Glu Val Ala Thr Val Val Ile Gln Pro
            115                 120                 125

Ser Val Leu Arg Ala Ala Val Pro Lys Asn Val Ser Val Ala Glu Gly
        130                 135                 140

Lys Glu Leu Asp Leu Thr Cys Asn Ile Thr Thr Asp Arg Ala Asp Asp
145                 150                 155                 160

Val Arg Pro Glu Val Thr Trp Ser Phe Ser Arg Met Pro Asp Ser Thr
                165                 170                 175

Leu Pro Gly Ser Arg Val Leu Ala Arg Leu Asp Arg Asp Ser Leu Val
            180                 185                 190

His Ser Ser Pro His Val Ala Leu Ser His Val Asp Ala Arg Ser Tyr
        195                 200                 205

His Leu Leu Val Arg Asp Val Ser Lys Glu Asn Ser Gly Tyr Tyr Tyr
    210                 215                 220

Cys His Val Ser Leu Trp Ala Pro Gly His Asn Arg Ser Trp His Lys
225                 230                 235                 240

Val Ala Glu Ala Val Ser Ser Pro Ala Gly Val Gly Val Thr Trp Leu
                245                 250                 255

Glu Pro Asp Tyr Gln Val Tyr Leu Asn Ala Ser Lys Val Pro Gly Phe
            260                 265                 270

Ala Asp Asp Pro Thr Glu Leu Ala Cys Arg Val Val Asp Thr Lys Ser
        275                 280                 285

Gly Glu Ala Asn Val Arg Phe Thr Val Ser Trp Tyr Tyr Arg Met Asn
    290                 295                 300

Arg Arg Ser Asp Asn Val Val Thr Ser Glu Leu Leu Ala Val Met Asp
305                 310                 315                 320

Gly Asp Trp Thr Leu Lys Tyr Gly Glu Arg Ser Lys Gln Arg Ala Gln
                325                 330                 335

Asp Gly Asp Phe Ile Phe Ser Lys Glu His Thr Asp Thr Phe Asn Phe
            340                 345                 350

Arg Ile Gln Arg Thr Thr Glu Glu Asp Arg Gly Asn Tyr Tyr Cys Val
        355                 360                 365

Val Ser Ala Trp Thr Lys Gln Arg Asn Asn Ser Trp Val Lys Ser Lys
    370                 375                 380

Asp Val Phe Ser Lys Pro Val Asn Ile Phe Trp Ala Leu Glu Asp Ser
385                 390                 395                 400

Val Leu Val Val Lys Ala Arg Gln Pro Lys Pro Phe Phe Ala Ala Gly
                405                 410                 415

Asn Thr Phe Glu Met Thr Cys Lys Val Ser Ser Lys Asn Ile Lys Ser
            420                 425                 430

Pro Arg Tyr Ser Val Leu Ile Met Ala Glu Lys Pro Val Gly Asp Leu
        435                 440                 445

Ser Ser Pro Asn Glu Thr Lys Tyr Ile Ile Ser Leu Asp Gln Asp Ser
    450                 455                 460

Val Val Lys Leu Glu Asn Trp Thr Asp Ala Ser Arg Val Asp Gly Val
465                 470                 475                 480

Val Leu Glu Lys Val Gln Glu Asp Glu Phe Arg Tyr Arg Met Tyr Gln
                485                 490                 495

Thr Gln Val Ser Asp Ala Gly Leu Tyr Arg Cys Met Val Thr Ala Trp
            500                 505                 510

Ser Pro Val Arg Gly Ser Leu Trp Arg Glu Ala Ala Thr Ser Leu Ser
        515                 520                 525
```

Asn Pro Ile Glu Ile Asp Phe Gln Thr Ser Gly Pro Ile Phe Asn Ala
530                 535                 540

Ser Val His Ser Asp Thr Pro Ser Val Ile Arg Gly Asp Leu Ile Lys
545                 550                 555                 560

Leu Phe Cys Ile Ile Thr Val Glu Gly Ala Ala Leu Asp Pro Asp Asp
                565                 570                 575

Met Ala Phe Asp Val Ser Trp Phe Ala Val His Ser Phe Gly Leu Asp
                580                 585                 590

Lys Ala Pro Val Leu Leu Ser Ser Leu Asp Arg Lys Gly Ile Val Thr
                595                 600                 605

Thr Ser Arg Arg Asp Trp Lys Ser Asp Leu Ser Leu Glu Arg Val Ser
610                 615                 620

Val Leu Glu Phe Leu Leu Gln Val His Gly Ser Glu Asp Gln Asp Phe
625                 630                 635                 640

Gly Asn Tyr Tyr Cys Ser Val Thr Pro Trp Val Lys Ser Pro Thr Gly
                645                 650                 655

Ser Trp Gln Lys Glu Ala Glu Ile His Ser Lys Pro Val Phe Ile Thr
                660                 665                 670

Val Lys Met Asp Val Leu Asn Ala Phe Lys Tyr Pro Leu Leu Ile Gly
                675                 680                 685

Val Gly Leu Ser Thr Val Ile Gly Leu Leu Ser Cys Leu Ile Gly Tyr
                690                 695                 700

Cys Ser Ser His Trp Cys Cys Lys Lys Glu Val Gln Glu Thr Arg Arg
705                 710                 715                 720

Glu Arg Arg Arg Leu Met Ser Met Glu Met Asp
                725                 730

<210> SEQ ID NO 3
<211> LENGTH: 611
<212> TYPE: PRT
<213> ORGANISM: Homo sapiens

<400> SEQUENCE: 3

Val Ala Thr Val Val Ile Gln Pro Ser Val Leu Arg Ala Ala Val Pro
1               5                   10                  15

Lys Asn Val Ser Val Ala Glu Gly Lys Glu Leu Asp Leu Thr Cys Asn
                20                  25                  30

Ile Thr Thr Asp Arg Ala Asp Asp Val Arg Pro Glu Val Thr Trp Ser
            35                  40                  45

Phe Ser Arg Met Pro Asp Ser Thr Leu Pro Gly Ser Arg Val Leu Ala
50                  55                  60

Arg Leu Asp Arg Asp Ser Leu Val His Ser Ser Pro His Val Ala Leu
65                  70                  75                  80

Ser His Val Asp Ala Arg Ser Tyr His Leu Leu Val Arg Asp Val Ser
                85                  90                  95

Lys Glu Asn Ser Gly Tyr Tyr Tyr Cys His Val Ser Leu Trp Ala Pro
                100                 105                 110

Gly His Asn Arg Ser Trp His Lys Val Ala Glu Ala Val Ser Ser Pro
            115                 120                 125

Ala Gly Val Gly Val Thr Trp Leu Glu Pro Asp Tyr Gln Val Tyr Leu
130                 135                 140

Asn Ala Ser Lys Val Pro Gly Phe Ala Asp Asp Pro Thr Glu Leu Ala
145                 150                 155                 160

Cys Arg Val Val Asp Thr Lys Ser Gly Glu Ala Asn Val Arg Phe Thr
                165                 170                 175

```
Val Ser Trp Tyr Tyr Arg Met Asn Arg Arg Ser Asp Asn Val Val Thr
            180                 185                 190

Ser Glu Leu Leu Ala Val Met Asp Gly Asp Trp Thr Leu Lys Tyr Gly
            195                 200                 205

Glu Arg Ser Lys Gln Arg Ala Gln Asp Gly Asp Phe Ile Phe Ser Lys
            210                 215                 220

Glu His Thr Asp Thr Phe Asn Phe Arg Ile Gln Arg Thr Thr Glu Glu
225                 230                 235                 240

Asp Arg Gly Asn Tyr Tyr Cys Val Val Ser Ala Trp Thr Lys Gln Arg
                245                 250                 255

Asn Asn Ser Trp Val Lys Ser Lys Asp Val Phe Ser Lys Pro Val Asn
            260                 265                 270

Ile Phe Trp Ala Leu Glu Asp Ser Val Leu Val Val Lys Ala Arg Gln
            275                 280                 285

Pro Lys Pro Phe Phe Ala Ala Gly Asn Thr Phe Glu Met Thr Cys Lys
            290                 295                 300

Val Ser Ser Lys Asn Ile Lys Ser Pro Arg Tyr Ser Val Leu Ile Met
305                 310                 315                 320

Ala Glu Lys Pro Val Gly Asp Leu Ser Ser Pro Asn Glu Thr Lys Tyr
                325                 330                 335

Ile Ile Ser Leu Asp Gln Asp Ser Val Val Lys Leu Glu Asn Trp Thr
            340                 345                 350

Asp Ala Ser Arg Val Asp Gly Val Val Leu Glu Lys Val Gln Glu Asp
            355                 360                 365

Glu Phe Arg Tyr Arg Met Tyr Gln Thr Gln Val Ser Asp Ala Gly Leu
            370                 375                 380

Tyr Arg Cys Met Val Thr Ala Trp Ser Pro Val Arg Gly Ser Leu Trp
385                 390                 395                 400

Arg Glu Ala Ala Thr Ser Leu Ser Asn Pro Ile Glu Ile Asp Phe Gln
                405                 410                 415

Thr Ser Gly Pro Ile Phe Asn Ala Ser Val His Ser Asp Thr Pro Ser
            420                 425                 430

Val Ile Arg Gly Asp Leu Ile Lys Leu Phe Cys Ile Ile Thr Val Glu
            435                 440                 445

Gly Ala Ala Leu Asp Pro Asp Asp Met Ala Phe Asp Val Ser Trp Phe
450                 455                 460

Ala Val His Ser Phe Gly Leu Asp Lys Ala Pro Val Leu Leu Ser Ser
465                 470                 475                 480

Leu Asp Arg Lys Gly Ile Val Thr Thr Ser Arg Arg Asp Trp Lys Ser
                485                 490                 495

Asp Leu Ser Leu Glu Arg Val Ser Val Leu Glu Phe Leu Leu Gln Val
            500                 505                 510

His Gly Ser Glu Asp Gln Asp Phe Gly Asn Tyr Tyr Cys Ser Val Thr
            515                 520                 525

Pro Trp Val Lys Ser Pro Thr Gly Ser Trp Gln Lys Glu Ala Glu Ile
            530                 535                 540

His Ser Lys Pro Val Phe Ile Thr Val Lys Met Asp Val Leu Asn Ala
545                 550                 555                 560

Phe Lys Tyr Pro Leu Leu Ile Gly Val Gly Leu Ser Thr Val Ile Gly
                565                 570                 575

Leu Leu Ser Cys Leu Ile Gly Tyr Cys Ser Ser His Trp Cys Cys Lys
            580                 585                 590
```

-continued

Lys Glu Val Gln Glu Thr Arg Arg Glu Arg Arg Leu Met Ser Met
            595                 600                 605
Glu Met Asp
    610

<210> SEQ ID NO 4
<211> LENGTH: 485
<212> TYPE: PRT
<213> ORGANISM: Homo sapiens

<400> SEQUENCE: 4

Ser Pro Ala Gly Val Gly Val Thr Trp Leu Glu Pro Asp Tyr Gln Val
1               5                   10                  15

Tyr Leu Asn Ala Ser Lys Val Pro Gly Phe Ala Asp Asp Pro Thr Glu
            20                  25                  30

Leu Ala Cys Arg Val Val Asp Thr Lys Ser Gly Glu Ala Asn Val Arg
        35                  40                  45

Phe Thr Val Ser Trp Tyr Tyr Arg Met Asn Arg Ser Asp Asn Val
    50                  55                  60

Val Thr Ser Glu Leu Leu Ala Val Met Asp Gly Asp Trp Thr Leu Lys
65                  70                  75                  80

Tyr Gly Glu Arg Ser Lys Gln Arg Ala Gln Asp Gly Asp Phe Ile Phe
                85                  90                  95

Ser Lys Glu His Thr Asp Thr Phe Asn Phe Arg Ile Gln Arg Thr Thr
            100                 105                 110

Glu Glu Asp Arg Gly Asn Tyr Tyr Cys Val Val Ser Ala Trp Thr Lys
        115                 120                 125

Gln Arg Asn Asn Ser Trp Val Lys Ser Lys Asp Val Phe Ser Lys Pro
    130                 135                 140

Val Asn Ile Phe Trp Ala Leu Glu Asp Ser Val Leu Val Val Lys Ala
145                 150                 155                 160

Arg Gln Pro Lys Pro Phe Phe Ala Ala Gly Asn Thr Phe Glu Met Thr
                165                 170                 175

Cys Lys Val Ser Ser Lys Asn Ile Lys Ser Pro Arg Tyr Ser Val Leu
            180                 185                 190

Ile Met Ala Glu Lys Pro Val Gly Asp Leu Ser Ser Pro Asn Glu Thr
        195                 200                 205

Lys Tyr Ile Ile Ser Leu Asp Gln Asp Ser Val Val Lys Leu Glu Asn
    210                 215                 220

Trp Thr Asp Ala Ser Arg Val Asp Gly Val Val Leu Glu Lys Val Gln
225                 230                 235                 240

Glu Asp Glu Phe Arg Tyr Arg Met Tyr Gln Thr Gln Val Ser Asp Ala
                245                 250                 255

Gly Leu Tyr Arg Cys Met Val Thr Ala Trp Ser Pro Val Arg Gly Ser
            260                 265                 270

Leu Trp Arg Glu Ala Ala Thr Ser Leu Ser Asn Pro Ile Glu Ile Asp
        275                 280                 285

Phe Gln Thr Ser Gly Pro Ile Phe Asn Ala Ser Val His Ser Asp Thr
    290                 295                 300

Pro Ser Val Ile Arg Gly Asp Leu Ile Lys Leu Phe Cys Ile Ile Thr
305                 310                 315                 320

Val Glu Gly Ala Ala Leu Asp Pro Asp Met Ala Phe Asp Val Ser
                325                 330                 335

Trp Phe Ala Val His Ser Phe Gly Leu Asp Lys Ala Pro Val Leu Leu
            340                 345                 350

```
Ser Ser Leu Asp Arg Lys Gly Ile Val Thr Thr Ser Arg Arg Asp Trp
        355                 360                 365

Lys Ser Asp Leu Ser Leu Glu Arg Val Ser Val Leu Glu Phe Leu Leu
    370                 375                 380

Gln Val His Gly Ser Glu Asp Gln Asp Phe Gly Asn Tyr Tyr Cys Ser
385                 390                 395                 400

Val Thr Pro Trp Val Lys Ser Pro Thr Gly Ser Trp Gln Lys Glu Ala
                405                 410                 415

Glu Ile His Ser Lys Pro Val Phe Ile Thr Val Lys Met Asp Val Leu
                420                 425                 430

Asn Ala Phe Lys Tyr Pro Leu Leu Ile Gly Val Gly Leu Ser Thr Val
            435                 440                 445

Ile Gly Leu Leu Ser Cys Leu Ile Gly Tyr Cys Ser Ser His Trp Cys
        450                 455                 460

Cys Lys Lys Glu Val Gln Glu Thr Arg Arg Glu Arg Arg Arg Leu Met
465                 470                 475                 480

Ser Met Glu Met Asp
                485

<210> SEQ ID NO 5
<211> LENGTH: 343
<212> TYPE: PRT
<213> ORGANISM: Homo sapiens

<400> SEQUENCE: 5

Lys Pro Val Asn Ile Phe Trp Ala Leu Glu Asp Ser Val Leu Val Val
1               5                   10                  15

Lys Ala Arg Gln Pro Lys Pro Phe Phe Ala Ala Gly Asn Thr Phe Glu
            20                  25                  30

Met Thr Cys Lys Val Ser Ser Lys Asn Ile Lys Ser Pro Arg Tyr Ser
        35                  40                  45

Val Leu Ile Met Ala Glu Lys Pro Val Gly Asp Leu Ser Ser Pro Asn
    50                  55                  60

Glu Thr Lys Tyr Ile Ile Ser Leu Asp Gln Asp Ser Val Val Lys Leu
65                  70                  75                  80

Glu Asn Trp Thr Asp Ala Ser Arg Val Asp Gly Val Val Leu Glu Lys
                85                  90                  95

Val Gln Glu Asp Glu Phe Arg Tyr Arg Met Tyr Gln Thr Gln Val Ser
            100                 105                 110

Asp Ala Gly Leu Tyr Arg Cys Met Val Thr Ala Trp Ser Pro Val Arg
        115                 120                 125

Gly Ser Leu Trp Arg Glu Ala Ala Thr Ser Leu Ser Asn Pro Ile Glu
    130                 135                 140

Ile Asp Phe Gln Thr Ser Gly Pro Ile Phe Asn Ala Ser Val His Ser
145                 150                 155                 160

Asp Thr Pro Ser Val Ile Arg Gly Asp Leu Ile Lys Leu Phe Cys Ile
                165                 170                 175

Ile Thr Val Glu Gly Ala Ala Leu Asp Pro Asp Asp Met Ala Phe Asp
            180                 185                 190

Val Ser Trp Phe Ala Val His Ser Phe Gly Leu Asp Lys Ala Pro Val
        195                 200                 205

Leu Leu Ser Ser Leu Asp Arg Lys Gly Ile Val Thr Thr Ser Arg Arg
    210                 215                 220

Asp Trp Lys Ser Asp Leu Ser Leu Glu Arg Val Ser Val Leu Glu Phe
```

```
                225                 230                 235                 240
Leu Leu Gln Val His Gly Ser Glu Asp Gln Asp Phe Gly Asn Tyr Tyr
                245                 250                 255

Cys Ser Val Thr Pro Trp Val Lys Ser Pro Thr Gly Ser Trp Gln Lys
                260                 265                 270

Glu Ala Glu Ile His Ser Lys Pro Val Phe Ile Thr Val Lys Met Asp
                275                 280                 285

Val Leu Asn Ala Phe Lys Tyr Pro Leu Leu Ile Gly Val Gly Leu Ser
                290                 295                 300

Thr Val Ile Gly Leu Leu Ser Cys Leu Ile Gly Tyr Cys Ser Ser His
305                 310                 315                 320

Trp Cys Cys Lys Lys Glu Val Gln Glu Thr Arg Arg Glu Arg Arg Arg
                325                 330                 335

Leu Met Ser Met Glu Met Asp
                340

<210> SEQ ID NO 6
<211> LENGTH: 217
<212> TYPE: PRT
<213> ORGANISM: Homo sapiens

<400> SEQUENCE: 6

Val Arg Gly Ser Leu Trp Arg Glu Ala Ala Thr Ser Leu Ser Asn Pro
1               5                   10                  15

Ile Glu Ile Asp Phe Gln Thr Ser Gly Pro Ile Phe Asn Ala Ser Val
                20                  25                  30

His Ser Asp Thr Pro Ser Val Ile Arg Gly Asp Leu Ile Lys Leu Phe
                35                  40                  45

Cys Ile Ile Thr Val Glu Gly Ala Ala Leu Asp Pro Asp Asp Met Ala
            50                  55                  60

Phe Asp Val Ser Trp Phe Ala Val His Ser Phe Gly Leu Asp Lys Ala
65                  70                  75                  80

Pro Val Leu Leu Ser Ser Leu Asp Arg Lys Gly Ile Val Thr Thr Ser
                85                  90                  95

Arg Arg Asp Trp Lys Ser Asp Leu Ser Leu Glu Arg Val Ser Val Leu
                100                 105                 110

Glu Phe Leu Leu Gln Val His Gly Ser Glu Asp Gln Asp Phe Gly Asn
                115                 120                 125

Tyr Tyr Cys Ser Val Thr Pro Trp Val Lys Ser Pro Thr Gly Ser Trp
            130                 135                 140

Gln Lys Glu Ala Glu Ile His Ser Lys Pro Val Phe Ile Thr Val Lys
145                 150                 155                 160

Met Asp Val Leu Asn Ala Phe Lys Tyr Pro Leu Leu Ile Gly Val Gly
                165                 170                 175

Leu Ser Thr Val Ile Gly Leu Leu Ser Cys Leu Ile Gly Tyr Cys Ser
                180                 185                 190

Ser His Trp Cys Cys Lys Lys Glu Val Gln Glu Thr Arg Arg Glu Arg
            195                 200                 205

Arg Arg Leu Met Ser Met Glu Met Asp
    210                 215

<210> SEQ ID NO 7
<211> LENGTH: 66
<212> TYPE: PRT
<213> ORGANISM: Homo sapiens
```

```
<400> SEQUENCE: 7

Ser Lys Pro Val Phe Ile Thr Val Lys Met Asp Val Leu Asn Ala Phe
1               5                   10                  15

Lys Tyr Pro Leu Leu Ile Gly Val Gly Leu Ser Thr Val Ile Gly Leu
            20                  25                  30

Leu Ser Cys Leu Ile Gly Tyr Cys Ser Ser His Trp Cys Cys Lys Lys
        35                  40                  45

Glu Val Gln Glu Thr Arg Arg Glu Arg Arg Leu Met Ser Met Glu
50                  55                  60

Met Asp
65

<210> SEQ ID NO 8
<211> LENGTH: 21
<212> TYPE: PRT
<213> ORGANISM: Homo sapiens

<400> SEQUENCE: 8

Met Gly Arg Leu Ala Ser Arg Pro Leu Leu Leu Ala Leu Leu Ser Leu
1               5                   10                  15

Ala Leu Cys Arg Gly
            20

<210> SEQ ID NO 9
<211> LENGTH: 385
<212> TYPE: PRT
<213> ORGANISM: Homo sapiens

<400> SEQUENCE: 9

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
```

```
                210                 215                 220
Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
                275                 280                 285

Asn Leu Asn Met Glu Ala Asp Pro Gly Gln Tyr Arg Cys Asn Gly Thr
            290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
                355                 360                 365

Gly Gln His Gln Asn Asp Lys Gly Lys Asn Val Arg Gln Arg Asn Ser
            370                 375                 380

Ser
385

<210> SEQ ID NO 10
<211> LENGTH: 247
<212> TYPE: PRT
<213> ORGANISM: Homo sapiens

<400> SEQUENCE: 10

Pro Gly Thr Val Phe Thr Thr Val Glu Asp Leu Gly Ser Lys Ile Leu
1               5                   10                  15

Leu Thr Cys Ser Leu Asn Asp Ser Ala Thr Glu Val Thr Gly His Arg
                20                  25                  30

Trp Leu Lys Gly Gly Val Val Leu Lys Glu Asp Ala Leu Pro Gly Gln
            35                  40                  45

Lys Thr Glu Phe Lys Val Asp Ser Asp Asp Gln Trp Gly Glu Tyr Ser
50                  55                  60

Cys Val Phe Leu Pro Glu Pro Met Gly Thr Ala Asn Ile Gln Leu His
65                  70                  75                  80

Gly Pro Pro Arg Val Lys Ala Val Lys Ser Ser Glu His Ile Asn Glu
                85                  90                  95

Gly Glu Thr Ala Met Leu Val Cys Lys Ser Glu Ser Val Pro Pro Val
            100                 105                 110

Thr Asp Trp Ala Trp Tyr Lys Ile Thr Asp Ser Glu Asp Lys Ala Leu
        115                 120                 125

Met Asn Gly Ser Glu Ser Arg Phe Phe Val Ser Ser Ser Gln Gly Arg
130                 135                 140

Ser Glu Leu His Ile Glu Asn Leu Asn Met Glu Ala Asp Pro Gly Gln
145                 150                 155                 160

Tyr Arg Cys Asn Gly Thr Ser Ser Lys Gly Ser Asp Gln Ala Ile Ile
                165                 170                 175

Thr Leu Arg Val Arg Ser His Leu Ala Ala Leu Trp Pro Phe Leu Gly
            180                 185                 190
```

Ile Val Ala Glu Val Leu Val Leu Val Thr Ile Ile Phe Ile Tyr Glu
         195                 200                 205

Lys Arg Arg Lys Pro Glu Asp Val Leu Asp Asp Asp Ala Gly Ser
210                 215                 220

Ala Pro Leu Lys Ser Ser Gly Gln His Gln Asn Asp Lys Gly Lys Asn
225                 230                 235                 240

Val Arg Gln Arg Asn Ser Ser
                245

<210> SEQ ID NO 11
<211> LENGTH: 168
<212> TYPE: PRT
<213> ORGANISM: Homo sapiens

<400> SEQUENCE: 11

His Gly Pro Pro Arg Val Lys Ala Val Lys Ser Ser Glu His Ile Asn
1               5                   10                  15

Glu Gly Glu Thr Ala Met Leu Val Cys Lys Ser Glu Ser Val Pro Pro
                20                  25                  30

Val Thr Asp Trp Ala Trp Tyr Lys Ile Thr Asp Ser Glu Asp Lys Ala
            35                  40                  45

Leu Met Asn Gly Ser Glu Ser Arg Phe Phe Val Ser Ser Ser Gln Gly
    50                  55                  60

Arg Ser Glu Leu His Ile Glu Asn Leu Asn Met Glu Ala Asp Pro Gly
65                  70                  75                  80

Gln Tyr Arg Cys Asn Gly Thr Ser Ser Lys Gly Ser Asp Gln Ala Ile
                85                  90                  95

Ile Thr Leu Arg Val Arg Ser His Leu Ala Ala Leu Trp Pro Phe Leu
            100                 105                 110

Gly Ile Val Ala Glu Val Leu Val Leu Val Thr Ile Ile Phe Ile Tyr
        115                 120                 125

Glu Lys Arg Arg Lys Pro Glu Asp Val Leu Asp Asp Asp Ala Gly
    130                 135                 140

Ser Ala Pro Leu Lys Ser Ser Gly Gln His Gln Asn Asp Lys Gly Lys
145                 150                 155                 160

Asn Val Arg Gln Arg Asn Ser Ser
                165

<210> SEQ ID NO 12
<211> LENGTH: 66
<212> TYPE: PRT
<213> ORGANISM: Homo sapiens

<400> SEQUENCE: 12

Ser His Leu Ala Ala Leu Trp Pro Phe Leu Gly Ile Val Ala Glu Val
1               5                   10                  15

Leu Val Leu Val Thr Ile Ile Phe Ile Tyr Glu Lys Arg Arg Lys Pro
                20                  25                  30

Glu Asp Val Leu Asp Asp Asp Ala Gly Ser Ala Pro Leu Lys Ser
            35                  40                  45

Ser Gly Gln His Gln Asn Asp Lys Gly Lys Asn Val Arg Gln Arg Asn
    50                  55                  60

Ser Ser
65

<210> SEQ ID NO 13
<211> LENGTH: 18

```
<212> TYPE: PRT
<213> ORGANISM: Homo sapiens

<400> SEQUENCE: 13

Met Ala Ala Leu Phe Val Leu Leu Gly Phe Ala Leu Leu Gly Thr
1               5                   10                  15

His Gly

<210> SEQ ID NO 14
<211> LENGTH: 613
<212> TYPE: PRT
<213> ORGANISM: Homo sapiens

<400> SEQUENCE: 14

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala Arg Glu Val Leu Val
                20                  25                  30

Pro Glu Gly Pro Leu Tyr Arg Val Ala Gly Thr Ala Val Ser Ile Ser
            35                  40                  45

Cys Asn Val Thr Gly Tyr Glu Gly Pro Ala Gln Gln Asn Phe Glu Trp
    50                  55                  60

Phe Leu Tyr Arg Pro Glu Ala Pro Asp Thr Ala Leu Gly Ile Val Ser
65                  70                  75                  80

Thr Lys Asp Thr Gln Phe Ser Tyr Ala Val Phe Lys Ser Arg Val Val
                85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205

Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255

Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala Glu
        275                 280                 285

Lys Arg Ala Val Leu Ala His Val Asp Val Gln Thr Leu Ser Ser Gln
    290                 295                 300

Leu Ala Val Thr Val Gly Pro Gly Glu Arg Arg Ile Gly Pro Gly Glu
305                 310                 315                 320

Pro Leu Glu Leu Leu Cys Asn Val Ser Gly Ala Leu Pro Pro Ala Gly
```

```
            325                 330                 335
Arg His Ala Ala Tyr Ser Val Gly Trp Glu Met Ala Pro Ala Gly Ala
            340                 345                 350
Pro Gly Pro Gly Arg Leu Val Ala Gln Leu Asp Thr Glu Gly Val Gly
            355                 360                 365
Ser Leu Gly Pro Gly Tyr Glu Gly Arg His Ile Ala Met Glu Lys Val
            370                 375                 380
Ala Ser Arg Thr Tyr Arg Leu Arg Leu Glu Ala Ala Arg Pro Gly Asp
385                 390                 395                 400
Ala Gly Thr Tyr Arg Cys Leu Ala Lys Ala Tyr Val Arg Gly Ser Gly
                405                 410                 415
Thr Arg Leu Arg Glu Ala Ala Ser Ala Arg Ser Arg Pro Leu Pro Val
                420                 425                 430
His Val Arg Glu Glu Gly Val Val Leu Glu Ala Val Ala Trp Leu Ala
                435                 440                 445
Gly Gly Thr Val Tyr Arg Gly Glu Thr Ala Ser Leu Leu Cys Asn Ile
            450                 455                 460
Ser Val Arg Gly Gly Pro Pro Gly Leu Arg Leu Ala Ala Ser Trp Trp
465                 470                 475                 480
Val Glu Arg Pro Glu Asp Gly Glu Leu Ser Ser Val Pro Ala Gln Leu
                485                 490                 495
Val Gly Gly Val Gly Gln Asp Gly Val Ala Glu Leu Gly Val Arg Pro
            500                 505                 510
Gly Gly Gly Pro Val Ser Val Glu Leu Val Gly Pro Arg Ser His Arg
            515                 520                 525
Leu Arg Leu His Ser Leu Gly Pro Glu Asp Glu Gly Val Tyr His Cys
            530                 535                 540
Ala Pro Ser Ala Trp Val Gln His Ala Asp Tyr Ser Trp Tyr Gln Ala
545                 550                 555                 560
Gly Ser Ala Arg Ser Gly Pro Val Thr Val Tyr Pro Tyr Met His Ala
                565                 570                 575
Leu Asp Thr Leu Phe Val Pro Leu Leu Val Gly Thr Gly Val Ala Leu
            580                 585                 590
Val Thr Gly Ala Thr Val Leu Gly Thr Ile Thr Cys Cys Phe Met Lys
            595                 600                 605
Arg Leu Arg Lys Arg
            610

<210> SEQ ID NO 15
<211> LENGTH: 456
<212> TYPE: PRT
<213> ORGANISM: Homo sapiens

<400> SEQUENCE: 15

Ala Pro Pro Gly Pro Arg Gly Arg Gln Ala Pro Thr Ser Pro Arg
1               5                   10                  15
Met Thr Val His Glu Gly Gln Glu Leu Ala Leu Gly Cys Leu Ala Arg
                20                  25                  30
Thr Ser Thr Gln Lys His Thr His Leu Ala Val Ser Phe Gly Arg Ser
            35                  40                  45
Val Pro Glu Ala Pro Val Gly Arg Ser Thr Leu Gln Glu Val Val Gly
        50                  55                  60
Ile Arg Ser Asp Leu Ala Val Glu Ala Gly Ala Pro Tyr Ala Glu Arg
65              70                  75                  80
```

```
Leu Ala Ala Gly Glu Leu Arg Leu Gly Lys Glu Gly Thr Asp Arg Tyr
                 85                  90                  95

Arg Met Val Val Gly Gly Ala Gln Ala Gly Asp Ala Gly Thr Tyr His
            100                 105                 110

Cys Thr Ala Ala Glu Trp Ile Gln Asp Pro Asp Gly Ser Trp Ala Gln
            115                 120                 125

Ile Ala Glu Lys Arg Ala Val Leu Ala His Val Asp Val Gln Thr Leu
            130                 135                 140

Ser Ser Gln Leu Ala Val Thr Val Gly Pro Gly Glu Arg Arg Ile Gly
145                 150                 155                 160

Pro Gly Glu Pro Leu Glu Leu Leu Cys Asn Val Ser Gly Ala Leu Pro
                165                 170                 175

Pro Ala Gly Arg His Ala Ala Tyr Ser Val Gly Trp Glu Met Ala Pro
                180                 185                 190

Ala Gly Ala Pro Gly Pro Gly Arg Leu Val Ala Gln Leu Asp Thr Glu
                195                 200                 205

Gly Val Gly Ser Leu Gly Pro Gly Tyr Glu Gly Arg His Ile Ala Met
        210                 215                 220

Glu Lys Val Ala Ser Arg Thr Tyr Arg Leu Arg Leu Glu Ala Ala Arg
225                 230                 235                 240

Pro Gly Asp Ala Gly Thr Tyr Arg Cys Leu Ala Lys Ala Tyr Val Arg
                245                 250                 255

Gly Ser Gly Thr Arg Leu Arg Glu Ala Ala Ser Ala Arg Ser Arg Pro
                260                 265                 270

Leu Pro Val His Val Arg Glu Glu Gly Val Val Leu Glu Ala Val Ala
                275                 280                 285

Trp Leu Ala Gly Gly Thr Val Tyr Arg Gly Glu Thr Ala Ser Leu Leu
        290                 295                 300

Cys Asn Ile Ser Val Arg Gly Gly Pro Pro Gly Leu Arg Leu Ala Ala
305                 310                 315                 320

Ser Trp Trp Val Glu Arg Pro Glu Asp Gly Leu Ser Ser Val Pro
                325                 330                 335

Ala Gln Leu Val Gly Val Gly Gln Asp Gly Val Ala Glu Leu Gly
                340                 345                 350

Val Arg Pro Gly Gly Pro Val Ser Val Glu Leu Val Gly Pro Arg
                355                 360                 365

Ser His Arg Leu Arg Leu His Ser Leu Gly Pro Glu Asp Glu Gly Val
370                 375                 380

Tyr His Cys Ala Pro Ser Ala Trp Val Gln His Ala Asp Tyr Ser Trp
385                 390                 395                 400

Tyr Gln Ala Gly Ser Ala Arg Ser Gly Pro Val Thr Val Tyr Pro Tyr
                405                 410                 415

Met His Ala Leu Asp Thr Leu Phe Val Pro Leu Leu Val Gly Thr Gly
                420                 425                 430

Val Ala Leu Val Thr Gly Ala Thr Val Leu Gly Thr Ile Thr Cys Cys
                435                 440                 445

Phe Met Lys Arg Leu Arg Lys Arg
    450                 455

<210> SEQ ID NO 16
<211> LENGTH: 320
<212> TYPE: PRT
<213> ORGANISM: Homo sapiens

<400> SEQUENCE: 16
```

Ala His Val Asp Val Gln Thr Leu Ser Ser Gln Leu Ala Val Thr Val
1               5                   10                  15

Gly Pro Gly Glu Arg Arg Ile Gly Pro Gly Glu Pro Leu Glu Leu Leu
            20                  25                  30

Cys Asn Val Ser Gly Ala Leu Pro Pro Ala Gly Arg His Ala Ala Tyr
            35                  40                  45

Ser Val Gly Trp Glu Met Ala Pro Ala Gly Ala Pro Gly Pro Gly Arg
50                      55                  60

Leu Val Ala Gln Leu Asp Thr Glu Gly Val Gly Ser Leu Gly Pro Gly
65                  70                  75                  80

Tyr Glu Gly Arg His Ile Ala Met Glu Lys Val Ala Ser Arg Thr Tyr
                85                  90                  95

Arg Leu Arg Leu Glu Ala Ala Arg Pro Gly Asp Ala Gly Thr Tyr Arg
            100                 105                 110

Cys Leu Ala Lys Ala Tyr Val Arg Gly Ser Gly Thr Arg Leu Arg Glu
            115                 120                 125

Ala Ala Ser Ala Arg Ser Arg Pro Leu Pro Val His Val Arg Glu Glu
130                 135                 140

Gly Val Val Leu Glu Ala Val Ala Trp Leu Ala Gly Gly Thr Val Tyr
145                 150                 155                 160

Arg Gly Glu Thr Ala Ser Leu Leu Cys Asn Ile Ser Val Arg Gly Gly
                165                 170                 175

Pro Pro Gly Leu Arg Leu Ala Ala Ser Trp Trp Val Glu Arg Pro Glu
            180                 185                 190

Asp Gly Glu Leu Ser Ser Val Pro Ala Gln Leu Val Gly Gly Val Gly
            195                 200                 205

Gln Asp Gly Val Ala Glu Leu Gly Val Arg Pro Gly Gly Gly Pro Val
210                 215                 220

Ser Val Glu Leu Val Gly Pro Arg Ser His Arg Leu Arg Leu His Ser
225                 230                 235                 240

Leu Gly Pro Glu Asp Glu Gly Val Tyr His Cys Ala Pro Ser Ala Trp
                245                 250                 255

Val Gln His Ala Asp Tyr Ser Trp Tyr Gln Ala Gly Ser Ala Arg Ser
            260                 265                 270

Gly Pro Val Thr Val Tyr Pro Tyr Met His Ala Leu Asp Thr Leu Phe
            275                 280                 285

Val Pro Leu Leu Val Gly Thr Gly Val Ala Leu Val Thr Gly Ala Thr
            290                 295                 300

Val Leu Gly Thr Ile Thr Cys Cys Phe Met Lys Arg Leu Arg Lys Arg
305                 310                 315                 320

<210> SEQ ID NO 17
<211> LENGTH: 179
<212> TYPE: PRT
<213> ORGANISM: Homo sapiens

<400> SEQUENCE: 17

Arg Glu Glu Gly Val Val Leu Glu Ala Val Ala Trp Leu Ala Gly Gly
1               5                   10                  15

Thr Val Tyr Arg Gly Glu Thr Ala Ser Leu Leu Cys Asn Ile Ser Val
            20                  25                  30

Arg Gly Gly Pro Pro Gly Leu Arg Leu Ala Ala Ser Trp Trp Val Glu
            35                  40                  45

Arg Pro Glu Asp Gly Glu Leu Ser Ser Val Pro Ala Gln Leu Val Gly

```
                     50                    55                   60
Gly Val Gly Gln Asp Gly Val Ala Glu Leu Gly Val Arg Pro Gly Gly
 65                  70                   75                   80

Gly Pro Val Ser Val Glu Leu Val Gly Pro Arg Ser His Arg Leu Arg
                 85                   90                   95

Leu His Ser Leu Gly Pro Glu Asp Glu Gly Val Tyr His Cys Ala Pro
                100                  105                  110

Ser Ala Trp Val Gln His Ala Asp Tyr Ser Trp Tyr Gln Ala Gly Ser
            115                  120                  125

Ala Arg Ser Gly Pro Val Thr Val Tyr Pro Tyr Met His Ala Leu Asp
130                  135                  140

Thr Leu Phe Val Pro Leu Leu Val Gly Thr Val Ala Leu Val Thr
145                  150                  155                  160

Gly Ala Thr Val Leu Gly Thr Ile Thr Cys Cys Phe Met Lys Arg Leu
                165                  170                  175

Arg Lys Arg

<210> SEQ ID NO 18
<211> LENGTH: 24
<212> TYPE: PRT
<213> ORGANISM: Homo sapiens

<400> SEQUENCE: 18

Val Ala Leu Val Thr Gly Ala Thr Val Leu Gly Thr Ile Thr Cys Cys
  1               5                  10                  15

Phe Met Lys Arg Leu Arg Lys Arg
                20

<210> SEQ ID NO 19
<211> LENGTH: 27
<212> TYPE: PRT
<213> ORGANISM: Homo sapiens

<400> SEQUENCE: 19

Met Gly Ala Leu Arg Pro Thr Leu Leu Pro Pro Ser Leu Pro Leu Leu
  1               5                  10                  15

Leu Leu Leu Met Leu Gly Met Gly Cys Trp Ala
                20                  25

<210> SEQ ID NO 20
<211> LENGTH: 1195
<212> TYPE: PRT
<213> ORGANISM: Homo sapiens

<400> SEQUENCE: 20

Met Lys Cys Phe Phe Pro Val Leu Ser Cys Leu Ala Val Leu Gly Val
  1               5                  10                  15

Val Ser Ala Gln Arg Gln Val Thr Val Gln Glu Gly Pro Leu Tyr Arg
                20                  25                  30

Thr Glu Gly Ser His Ile Thr Ile Trp Cys Asn Val Ser Gly Tyr Gln
            35                   40                  45

Gly Pro Ser Glu Gln Asn Phe Gln Trp Ser Ile Tyr Leu Pro Ser Ser
         50                  55                  60

Pro Glu Arg Glu Val Gln Ile Val Ser Thr Met Asp Ser Ser Phe Pro
 65                  70                   75                  80

Tyr Ala Ile Tyr Thr Gln Arg Val Arg Gly Gly Lys Ile Phe Ile Glu
                85                  90                   95
```

```
Arg Val Gln Gly Asn Ser Thr Leu Leu His Ile Thr Asp Leu Gln Ala
            100                 105                 110
Arg Asp Ala Gly Glu Tyr Glu Cys His Thr Pro Ser Thr Asp Lys Gln
            115                 120                 125
Tyr Phe Gly Ser Tyr Ser Ala Lys Met Asn Leu Val Val Ile Pro Asp
            130                 135                 140
Ser Leu Gln Thr Thr Ala Met Pro Gln Thr Leu His Arg Val Glu Gln
145                 150                 155                 160
Asp Pro Leu Glu Leu Thr Cys Glu Val Ala Ser Glu Thr Ile Gln His
                    165                 170                 175
Ser His Leu Ser Val Ala Trp Leu Arg Gln Lys Val Gly Glu Lys Pro
            180                 185                 190
Val Glu Val Ile Ser Leu Ser Arg Asp Phe Met Leu His Ser Ser Ser
            195                 200                 205
Glu Tyr Ala Gln Arg Gln Ser Leu Gly Glu Val Arg Leu Asp Lys Leu
            210                 215                 220
Gly Arg Thr Thr Phe Arg Leu Thr Ile Phe His Leu Gln Pro Ser Asp
225                 230                 235                 240
Gln Gly Glu Phe Tyr Cys Glu Ala Ala Glu Trp Ile Gln Asp Pro Asp
                    245                 250                 255
Gly Ser Trp Tyr Ala Met Thr Arg Lys Arg Ser Glu Gly Ala Val Val
                260                 265                 270
Asn Val Gln Pro Thr Asp Lys Glu Phe Thr Val Arg Leu Glu Thr Glu
            275                 280                 285
Lys Arg Leu His Thr Val Gly Glu Pro Val Glu Phe Arg Cys Ile Leu
290                 295                 300
Glu Ala Gln Asn Val Pro Asp Arg Tyr Phe Ala Val Ser Trp Ala Phe
305                 310                 315                 320
Asn Ser Ser Leu Ile Ala Thr Met Gly Pro Asn Ala Val Pro Val Leu
                325                 330                 335
Asn Ser Glu Phe Ala His Arg Glu Ala Arg Gly Gln Leu Lys Val Ala
                340                 345                 350
Lys Glu Ser Asp Ser Val Phe Val Leu Lys Ile Tyr His Leu Arg Gln
            355                 360                 365
Glu Asp Ser Gly Lys Tyr Asn Cys Arg Val Thr Glu Arg Glu Lys Thr
            370                 375                 380
Val Thr Gly Glu Phe Ile Asp Lys Glu Ser Lys Arg Pro Lys Asn Ile
385                 390                 395                 400
Pro Ile Ile Val Leu Pro Leu Lys Ser Ser Ile Ser Val Glu Val Ala
                    405                 410                 415
Ser Asn Ala Ser Val Ile Leu Glu Gly Glu Asp Leu Arg Phe Ser Cys
            420                 425                 430
Ser Val Arg Thr Ala Gly Arg Pro Gln Gly Arg Phe Ser Val Ile Trp
            435                 440                 445
Gln Leu Val Asp Arg Gln Asn Arg Arg Ser Asn Ile Met Trp Leu Asp
            450                 455                 460
Arg Asp Gly Thr Val Gln Pro Gly Ser Ser Tyr Trp Glu Arg Ser Ser
465                 470                 475                 480
Phe Gly Gly Val Gln Met Glu Gln Val Gln Pro Asn Ser Phe Ser Leu
                    485                 490                 495
Gly Ile Phe Asn Ser Arg Lys Glu Asp Glu Gly Gln Tyr Glu Cys His
                500                 505                 510
Val Thr Glu Trp Val Arg Ala Val Asp Gly Glu Trp Gln Ile Val Gly
```

```
            515                 520                 525
Glu Arg Arg Ala Ser Thr Pro Ile Ser Ile Thr Ala Leu Glu Met Gly
530                 535                 540

Phe Ala Val Thr Ala Ile Ser Arg Thr Pro Gly Val Thr Tyr Ser Asp
545                 550                 555                 560

Ser Phe Asp Leu Gln Cys Ile Ile Lys Pro His Tyr Pro Ala Trp Val
                565                 570                 575

Pro Val Ser Val Thr Trp Arg Phe Gln Pro Val Gly Thr Val Glu Phe
            580                 585                 590

His Asp Leu Val Thr Phe Thr Arg Asp Gly Gly Val Gln Trp Gly Asp
                595                 600                 605

Arg Ser Ser Ser Phe Arg Thr Arg Thr Ala Ile Glu Lys Ala Glu Ser
610                 615                 620

Ser Asn Asn Val Arg Leu Ser Ile Ser Arg Ala Ser Asp Thr Glu Ala
625                 630                 635                 640

Gly Lys Tyr Gln Cys Val Ala Glu Leu Trp Arg Lys Asn Tyr Asn Asn
                645                 650                 655

Thr Trp Thr Arg Leu Ala Glu Arg Thr Ser Asn Leu Leu Glu Ile Arg
                660                 665                 670

Val Leu Gln Pro Val Thr Lys Leu Gln Val Ser Lys Ser Lys Arg Thr
                675                 680                 685

Leu Thr Leu Val Glu Asn Lys Pro Ile Gln Leu Asn Cys Ser Val Lys
690                 695                 700

Ser Gln Thr Ser Gln Asn Ser His Phe Ala Val Leu Trp Tyr Val His
705                 710                 715                 720

Lys Pro Ser Asp Ala Asp Gly Lys Leu Ile Leu Lys Thr Thr His Asn
                725                 730                 735

Ser Ala Phe Glu Tyr Gly Thr Tyr Ala Glu Glu Glu Gly Leu Arg Ala
                740                 745                 750

Arg Leu Gln Phe Glu Arg His Val Ser Gly Gly Leu Phe Ser Leu Thr
                755                 760                 765

Val Gln Arg Ala Glu Val Ser Asp Ser Gly Ser Tyr Tyr Cys His Val
                770                 775                 780

Glu Glu Trp Leu Leu Ser Pro Asn Tyr Ala Trp Tyr Lys Leu Ala Glu
785                 790                 795                 800

Glu Val Ser Gly Arg Thr Glu Val Thr Val Lys Gln Pro Asp Ser Arg
                805                 810                 815

Leu Arg Leu Ser Gln Ala Gln Gly Asn Leu Ser Val Leu Glu Thr Arg
                820                 825                 830

Gln Val Gln Leu Glu Cys Val Val Leu Asn Arg Thr Ser Ile Thr Ser
                835                 840                 845

Gln Leu Met Val Glu Trp Phe Val Trp Lys Pro Asn His Pro Glu Arg
                850                 855                 860

Glu Thr Val Ala Arg Leu Ser Arg Asp Ala Thr Phe His Tyr Gly Glu
865                 870                 875                 880

Gln Ala Ala Lys Asn Asn Leu Lys Gly Arg Leu His Leu Glu Ser Pro
                885                 890                 895

Ser Pro Gly Val Tyr Arg Leu Phe Ile Gln Asn Val Ala Val Gln Asp
                900                 905                 910

Ser Gly Thr Tyr Ser Cys His Val Glu Glu Trp Leu Pro Ser Pro Ser
                915                 920                 925

Gly Met Trp Tyr Lys Arg Ala Glu Asp Thr Ala Gly Gln Thr Ala Leu
                930                 935                 940
```

```
Thr Val Met Arg Pro Asp Ala Ser Leu Gln Val Asp Thr Val Pro
945                 950                 955                 960

Asn Ala Thr Val Ser Glu Lys Ala Ala Phe Gln Leu Asp Cys Ser Ile
                965                 970                 975

Val Ser Arg Ser Ser Gln Asp Ser Arg Phe Ala Val Ala Trp Tyr Ser
            980                 985                 990

Leu Arg Thr Lys Ala Gly Gly Lys Arg Ser Ser Pro Gly Leu Glu Glu
        995                 1000                1005

Gln Glu Glu Glu Arg Glu Glu Glu Glu Glu Glu Glu Asp Asp
    1010                1015                1020

Asp Asp Asp Asp Pro Thr Glu Arg Thr Ala Leu Leu Ser Val Gly
    1025                1030                1035

Pro Asp Ala Val Phe Gly Pro Glu Gly Ser Pro Trp Glu Gly Arg
    1040                1045                1050

Leu Arg Phe Gln Arg Leu Ser Pro Val Leu Tyr Arg Leu Thr Val
    1055                1060                1065

Leu Gln Ala Ser Pro Gln Asp Thr Gly Asn Tyr Ser Cys His Val
    1070                1075                1080

Glu Glu Trp Leu Pro Ser Pro Gln Lys Gly Trp Tyr Arg Leu Thr
    1085                1090                1095

Glu Glu Glu Ser Ala Pro Ile Gly Ile Arg Val Leu Asp Thr Ser
    1100                1105                1110

Pro Thr Leu Gln Ser Ile Ile Cys Ser Asn Asp Ala Leu Phe Tyr
    1115                1120                1125

Phe Val Phe Phe Tyr Pro Phe Pro Ile Phe Gly Ile Leu Ile Ile
    1130                1135                1140

Thr Ile Leu Leu Val Arg Phe Lys Ser Arg Asn Ser Ser Lys Asn
    1145                1150                1155

Ser Asp Gly Lys Asn Gly Val Pro Leu Leu Trp Ile Lys Glu Pro
    1160                1165                1170

His Leu Asn Tyr Ser Pro Thr Cys Leu Glu Pro Pro Val Leu Ser
    1175                1180                1185

Ile His Pro Gly Ala Ile Asp
    1190                1195

<210> SEQ ID NO 21
<211> LENGTH: 798
<212> TYPE: PRT
<213> ORGANISM: Homo sapiens

<400> SEQUENCE: 21

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
```

```
                  100                 105                 110
    Gln Ile Gln Pro Gln Gln Leu Val Leu Arg Leu Arg Ser Gly Glu Pro
                      115                 120                 125
    Gln Thr Phe Thr Leu Lys Phe Lys Arg Ala Glu Asp Tyr Pro Ile Asp
    130                 135                 140
    Leu Tyr Tyr Leu Met Asp Leu Ser Tyr Ser Met Lys Asp Asp Leu Glu
    145                 150                 155                 160
    Asn Val Lys Ser Leu Gly Thr Asp Leu Met Asn Glu Met Arg Arg Ile
                      165                 170                 175
    Thr Ser Asp Phe Arg Ile Gly Phe Gly Ser Phe Val Glu Lys Thr Val
                      180                 185                 190
    Met Pro Tyr Ile Ser Thr Thr Pro Ala Lys Leu Arg Asn Pro Cys Thr
                      195                 200                 205
    Ser Glu Gln Asn Cys Thr Ser Pro Phe Ser Tyr Lys Asn Val Leu Ser
                      210                 215                 220
    Leu Thr Asn Lys Gly Glu Val Phe Asn Glu Leu Val Gly Lys Gln Arg
    225                 230                 235                 240
    Ile Ser Gly Asn Leu Asp Ser Pro Glu Gly Gly Phe Asp Ala Ile Met
                      245                 250                 255
    Gln Val Ala Val Cys Gly Ser Leu Ile Gly Trp Arg Asn Val Thr Arg
                      260                 265                 270
    Leu Leu Val Phe Ser Thr Asp Ala Gly Phe His Phe Ala Gly Asp Gly
                      275                 280                 285
    Lys Leu Gly Gly Ile Val Leu Pro Asn Asp Gly Gln Cys His Leu Glu
                      290                 295                 300
    Asn Asn Met Tyr Thr Met Ser His Tyr Tyr Asp Tyr Pro Ser Ile Ala
    305                 310                 315                 320
    His Leu Val Gln Lys Leu Ser Glu Asn Asn Ile Gln Thr Ile Phe Ala
                      325                 330                 335
    Val Thr Glu Glu Phe Gln Pro Val Tyr Lys Glu Leu Lys Asn Leu Ile
                      340                 345                 350
    Pro Lys Ser Ala Val Gly Thr Leu Ser Ala Asn Ser Ser Asn Val Ile
                      355                 360                 365
    Gln Leu Ile Ile Asp Ala Tyr Asn Ser Leu Ser Ser Glu Val Ile Leu
                      370                 375                 380
    Glu Asn Gly Lys Leu Ser Glu Gly Val Thr Ile Ser Tyr Lys Ser Tyr
    385                 390                 395                 400
    Cys Lys Asn Gly Val Asn Gly Thr Gly Glu Asn Gly Arg Lys Cys Ser
                      405                 410                 415
    Asn Ile Ser Ile Gly Asp Glu Val Gln Phe Glu Ile Ser Ile Thr Ser
                      420                 425                 430
    Asn Lys Cys Pro Lys Lys Asp Ser Asp Ser Phe Lys Ile Arg Pro Leu
                      435                 440                 445
    Gly Phe Thr Glu Glu Val Glu Val Ile Leu Gln Tyr Ile Cys Glu Cys
                      450                 455                 460
    Glu Cys Gln Ser Glu Gly Ile Pro Glu Ser Pro Lys Cys His Glu Gly
    465                 470                 475                 480
    Asn Gly Thr Phe Glu Cys Gly Ala Cys Arg Cys Asn Glu Gly Arg Val
                      485                 490                 495
    Gly Arg His Cys Glu Cys Ser Thr Asp Glu Val Asn Ser Glu Asp Met
                      500                 505                 510
    Asp Ala Tyr Cys Arg Lys Glu Asn Ser Ser Glu Ile Cys Ser Asn Asn
                      515                 520                 525
```

```
Gly Glu Cys Val Cys Gly Gln Cys Val Cys Arg Lys Arg Asp Asn Thr
            530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 22
<211> LENGTH: 1032
<212> TYPE: PRT
<213> ORGANISM: Homo sapiens

<400> SEQUENCE: 22

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
```

```
                100                 105                 110
Pro Cys Gly Lys Thr Cys Leu Glu Glu Arg Asp Asn Gln Trp Leu Gly
            115                 120                 125

Val Thr Leu Ser Arg Gln Pro Gly Glu Asn Gly Ser Ile Val Thr Cys
            130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
            165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
            195                 200                 205

Asp Leu Ile Val Met Gly Ala Pro Gly Ser Ser Tyr Trp Thr Gly Ser
            210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
            245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
            275                 280                 285

Lys Glu Leu Asn Ile Leu His Glu Met Lys Gly Lys Lys Leu Gly Ser
            290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
            325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
            355                 360                 365

Gly Glu Ser Ile Val Asn Leu Gly Asp Ile Asp Asn Asp Gly Phe Glu
            370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
            405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
            435                 440                 445

Ala Val Gly Ala Phe Arg Ser Asp Ser Ala Val Leu Leu Arg Thr Arg
            450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
            485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
            515                 520                 525
```

```
Ser Pro Pro Arg Phe Tyr Phe Ser Ser Asn Gly Thr Ser Asp Val Ile
    530                 535                 540
Thr Gly Ser Ile Gln Val Ser Ser Arg Glu Ala Asn Cys Arg Thr His
545                 550                 555                 560
Gln Ala Phe Met Arg Lys Asp Val Arg Asp Ile Leu Thr Pro Ile Gln
                565                 570                 575
Ile Glu Ala Ala Tyr His Leu Gly Pro His Val Ile Ser Lys Arg Ser
            580                 585                 590
Thr Glu Glu Phe Pro Pro Leu Gln Pro Ile Leu Gln Gln Lys Lys Glu
        595                 600                 605
Lys Asp Ile Met Lys Lys Thr Ile Asn Phe Ala Arg Phe Cys Ala His
    610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
                645                 650                 655
Leu Met Leu Asn Val Ser Leu Phe Asn Ala Gly Asp Asp Ala Tyr Glu
                660                 665                 670
Thr Thr Leu His Val Lys Leu Pro Val Gly Leu Tyr Phe Ile Lys Ile
            675                 680                 685
Leu Glu Leu Glu Glu Lys Gln Ile Asn Cys Glu Val Thr Asp Asn Ser
    690                 695                 700
Gly Val Val Gln Leu Asp Cys Ser Ile Gly Tyr Ile Tyr Val Asp His
705                 710                 715                 720
Leu Ser Arg Ile Asp Ile Ser Phe Leu Leu Asp Val Ser Ser Leu Ser
                725                 730                 735
Arg Ala Glu Glu Asp Leu Ser Ile Thr Val His Ala Thr Cys Glu Asn
                740                 745                 750
Glu Glu Glu Met Asp Asn Leu Lys His Ser Arg Val Thr Val Ala Ile
                755                 760                 765
Pro Leu Lys Tyr Glu Val Lys Leu Thr Val His Gly Phe Val Asn Pro
    770                 775                 780
Thr Ser Phe Val Tyr Gly Ser Asn Asp Glu Asn Glu Pro Glu Thr Cys
785                 790                 795                 800
Met Val Glu Lys Met Asn Leu Thr Phe His Val Ile Asn Thr Gly Asn
                805                 810                 815
Ser Met Ala Pro Asn Val Ser Val Glu Ile Met Val Pro Asn Ser Phe
                820                 825                 830
Ser Pro Gln Thr Asp Lys Leu Phe Asn Ile Leu Asp Val Gln Thr Thr
            835                 840                 845
Thr Gly Glu Cys His Phe Glu Asn Tyr Gln Arg Val Cys Ala Leu Glu
    850                 855                 860
Gln Gln Lys Ser Ala Met Gln Thr Leu Lys Gly Ile Val Arg Phe Leu
865                 870                 875                 880
Ser Lys Thr Asp Lys Arg Leu Leu Tyr Cys Ile Lys Ala Asp Pro His
                885                 890                 895
Cys Leu Asn Phe Leu Cys Asn Phe Gly Lys Met Glu Ser Gly Lys Glu
                900                 905                 910
Ala Ser Val His Ile Gln Leu Glu Gly Arg Pro Ser Ile Leu Glu Met
            915                 920                 925
Asp Glu Thr Ser Ala Leu Lys Phe Glu Ile Arg Ala Thr Gly Phe Pro
    930                 935                 940
```

-continued

```
Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
            965                 970                 975

Thr Ile Val Ile Ile Ser Ser Leu Leu Gly Leu Ile Val Leu
        980                 985                 990

Leu Leu Ile Ser Tyr Val Met Trp Lys Ala Gly Phe Phe Lys Arg Gln
    995                 1000                1005

Tyr Lys Ser Ile Leu Gln Glu Asn Arg Arg Asp Ser Trp Ser
    1010                1015                1020

Tyr Ile Asn Ser Lys Ser Asn Asp Asp
    1025                1030

<210> SEQ ID NO 23
<211> LENGTH: 661
<212> TYPE: PRT
<213> ORGANISM: Homo sapiens

<400> SEQUENCE: 23

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Leu Gly Ser His Cys Val Ala Gln Thr Gly
        35                  40                  45

Leu Glu Leu Leu Ala Ser Gly Asp Pro Leu Pro Ser Ala Ser Gln Asn
50                  55                  60

Ala Glu Met Ile Glu Thr Gly Ser Asp Cys Val Thr Gln Ala Gly Leu
65                  70                  75                  80

Gln Leu Leu Ala Ser Ser Asp Pro Pro Ala Leu Ala Ser Lys Asn Ala
                85                  90                  95

Glu Val Thr Glu Thr Gly Phe His His Val Ser Gln Ala Asp Ile Glu
            100                 105                 110

Phe Leu Thr Ser Ile Asp Pro Thr Ala Ser Ala Ser Gly Ser Ala Gly
        115                 120                 125

Ile Thr Gly Thr Met Ser Gln Asp Thr Glu Val Asp Met Lys Glu Val
130                 135                 140

Glu Leu Asn Glu Leu Glu Pro Glu Lys Gln Pro Met Asn Ala Ala Ser
145                 150                 155                 160

Gly Ala Ala Met Ser Leu Ala Gly Ala Glu Lys Asn Gly Leu Val Lys
                165                 170                 175

Ile Lys Val Ala Glu Asp Glu Ala Glu Ala Ala Ala Ala Ala Lys Phe
            180                 185                 190

Thr Gly Leu Ser Lys Glu Glu Leu Lys Val Ala Gly Ser Pro Gly
        195                 200                 205

Trp Val Arg Thr Arg Trp Ala Leu Leu Leu Phe Trp Leu Gly Trp
    210                 215                 220

Leu Gly Met Leu Ala Gly Ala Val Val Ile Val Arg Ala Pro Arg
225                 230                 235                 240

Cys Arg Glu Leu Pro Ala Gln Lys Trp Trp His Thr Gly Ala Leu Tyr
                245                 250                 255

Arg Ile Gly Asp Leu Gln Ala Phe Gln Gly His Gly Ala Gly Asn Leu
            260                 265                 270

Ala Gly Leu Lys Gly Arg Leu Asp Tyr Leu Ser Ser Leu Lys Val Lys
        275                 280                 285
```

```
Gly Leu Val Leu Gly Pro Ile His Lys Asn Gln Lys Asp Val Ala
    290                 295                 300

Gln Thr Asp Leu Leu Gln Ile Asp Pro Asn Phe Gly Ser Lys Glu Asp
305                 310                 315                 320

Phe Asp Ser Leu Leu Gln Ser Ala Lys Lys Ser Ile Arg Val Ile
            325                 330                 335

Leu Asp Leu Thr Pro Asn Tyr Arg Gly Glu Asn Ser Trp Phe Ser Thr
                340                 345                 350

Gln Val Asp Thr Val Ala Thr Lys Val Lys Asp Ala Leu Glu Phe Trp
            355                 360                 365

Leu Gln Ala Gly Val Asp Gly Phe Gln Val Arg Asp Ile Glu Asn Leu
    370                 375                 380

Lys Asp Ala Ser Ser Phe Leu Ala Glu Trp Gln Asn Ile Thr Lys Gly
385                 390                 395                 400

Phe Ser Glu Asp Arg Leu Leu Ile Ala Gly Thr Asn Ser Ser Asp Leu
                405                 410                 415

Gln Gln Ile Leu Ser Leu Leu Glu Ser Asn Lys Asp Leu Leu Leu Thr
            420                 425                 430

Ser Ser Tyr Leu Ser Asp Ser Gly Ser Thr Gly Glu His Thr Lys Ser
    435                 440                 445

Leu Val Thr Gln Tyr Leu Asn Ala Thr Gly Asn Arg Trp Cys Ser Trp
450                 455                 460

Ser Leu Ser Gln Ala Arg Leu Leu Thr Ser Phe Leu Pro Ala Gln Leu
465                 470                 475                 480

Leu Arg Leu Tyr Gln Leu Met Leu Phe Thr Leu Pro Gly Thr Pro Val
                485                 490                 495

Phe Ser Tyr Gly Asp Glu Ile Gly Leu Asp Ala Ala Leu Pro Gly
            500                 505                 510

Gln Pro Met Glu Ala Pro Val Met Leu Trp Asp Glu Ser Ser Phe Pro
    515                 520                 525

Asp Ile Pro Gly Ala Val Ser Ala Asn Met Thr Val Lys Gly Gln Ser
530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
            580                 585                 590

Arg Phe Leu Val Val Leu Asn Phe Gly Asp Val Gly Leu Ser Ala Gly
    595                 600                 605

Leu Gln Ala Ser Asp Leu Pro Ala Ser Ala Ser Leu Pro Ala Lys Ala
    610                 615                 620

Asp Leu Leu Leu Ser Thr Gln Pro Gly Arg Glu Glu Gly Ser Pro Leu
625                 630                 635                 640

Glu Leu Glu Arg Leu Lys Leu Glu Pro His Gly Leu Leu Leu Arg
                645                 650                 655

Phe Pro Tyr Ala Ala
            660

<210> SEQ ID NO 24
<211> LENGTH: 1023
<212> TYPE: PRT
<213> ORGANISM: Homo sapiens
```

```
<400> SEQUENCE: 24

Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
                20                  25                  30

Asp Glu Leu Lys Lys Glu Val Ser Met Asp Asp His Lys Leu Ser Leu
            35                  40                  45

Asp Glu Leu His Arg Lys Tyr Gly Thr Asp Leu Ser Arg Gly Leu Thr
        50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Pro Gln Asn Asp
        115                 120                 125

Asn Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
        275                 280                 285

Glu His Phe Ile His Ile Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
    370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415
```

```
Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
            435                 440                 445

Gly Asp Ala Ser Glu Ser Ala Leu Leu Lys Cys Ile Glu Leu Cys Cys
            450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
            485                 490                 495

Asn Thr Ser Glu Pro Gln His Leu Leu Val Met Lys Gly Ala Pro Glu
            500                 505                 510

Arg Ile Leu Asp Arg Cys Ser Ser Ile Leu Leu His Gly Lys Glu Gln
            515                 520                 525

Pro Leu Asp Glu Glu Leu Lys Asp Ala Phe Gln Asn Ala Tyr Leu Glu
            530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
            565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
            595                 600                 605

Ala Gly Ile Lys Val Ile Met Val Thr Gly Asp His Pro Ile Thr Ala
            610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
            645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
            675                 680                 685

Val Phe Ala Arg Thr Ser Pro Gln Gln Lys Leu Ile Ile Val Glu Gly
            690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
            725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
            755                 760                 765

Phe Asp Asn Leu Lys Lys Ser Ile Ala Tyr Thr Leu Thr Ser Asn Ile
            770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
            805                 810                 815

Val Pro Ala Ile Ser Leu Ala Tyr Glu Gln Ala Glu Ser Asp Ile Met
            820                 825                 830
```

```
                                           Lys Arg Gln Pro Arg Asn Pro Lys Thr Asp Lys Leu Val Asn Glu Arg
                                               835                 840                 845

Leu Ile Ser Met Ala Tyr Gly Gln Ile Gly Met Ile Gln Ala Leu Gly
                                           850                 855                 860

Gly Phe Phe Thr Tyr Phe Val Ile Leu Ala Glu Asn Gly Phe Leu Pro
                                           865                 870                 875                 880

Ile His Leu Leu Gly Leu Arg Val Asp Trp Asp Asp Arg Trp Ile Asn
                                                           885                 890                 895

Asp Val Glu Asp Ser Tyr Gly Gln Gln Trp Thr Tyr Glu Gln Arg Lys
                                                       900                 905                 910

Ile Val Glu Phe Thr Cys His Thr Ala Phe Pro Val Ser Ile Val Val
                                                       915                 920                 925

Val Gln Trp Ala Asp Leu Val Ile Cys Lys Thr Arg Arg Asn Ser Val
                                           930                 935                 940

Phe Gln Gln Gly Met Lys Asn Lys Ile Leu Ile Phe Gly Leu Phe Glu
                                           945                 950                 955                 960

Glu Thr Ala Leu Ala Ala Phe Leu Ser Tyr Cys Pro Gly Met Gly Val
                                                           965                 970                 975

Ala Leu Arg Met Tyr Pro Leu Lys Pro Thr Trp Trp Phe Cys Ala Phe
                                                       980                 985                 990

Pro Tyr Ser Leu Leu Ile Phe Val Tyr Asp Glu Val Arg Lys Leu Ile
                                                       995                 1000                1005

Ile Arg Arg Arg Pro Gly Gly Trp Val Glu Lys Glu Thr Tyr Tyr
                                                       1010                1015                1020

<210> SEQ ID NO 25
<211> LENGTH: 1020
<212> TYPE: PRT
<213> ORGANISM: Homo sapiens

<400> SEQUENCE: 25

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
            20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
                100                 105                 110

Tyr Gly Ile Gln Ala Ala Met Glu Asp Glu Pro Ser Asn Asp Asn Leu
            115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160

Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
            180                 185                 190
```

```
Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
210                 215                 220

Arg Ser Pro Glu Phe Thr His Glu Asn Pro Leu Glu Thr Arg Asn Ile
225                 230                 235                 240

Cys Phe Phe Ser Thr Asn Cys Val Glu Gly Thr Ala Arg Gly Ile Val
                245                 250                 255

Ile Ala Thr Gly Asp Arg Thr Val Met Gly Arg Ile Ala Thr Leu Ala
                260                 265                 270

Ser Gly Leu Glu Val Gly Arg Thr Pro Ile Ala Met Glu Ile Glu His
        275                 280                 285

Phe Ile Gln Leu Ile Thr Gly Val Ala Val Phe Leu Gly Val Ser Phe
        290                 295                 300

Phe Val Leu Ser Leu Ile Leu Gly Tyr Ser Trp Leu Glu Ala Val Ile
305                 310                 315                 320

Phe Leu Ile Gly Ile Ile Val Ala Asn Val Pro Glu Gly Leu Leu Ala
                325                 330                 335

Thr Val Thr Val Cys Leu Thr Leu Thr Ala Lys Arg Met Ala Arg Lys
                340                 345                 350

Asn Cys Leu Val Lys Asn Leu Glu Ala Val Glu Thr Leu Gly Ser Thr
        355                 360                 365

Ser Thr Ile Cys Ser Asp Lys Thr Gly Thr Leu Thr Gln Asn Arg Met
        370                 375                 380

Thr Val Ala His Met Trp Phe Asp Asn Gln Ile His Glu Ala Asp Thr
385                 390                 395                 400

Thr Glu Asp Gln Ser Gly Ala Thr Phe Asp Lys Arg Ser Pro Thr Trp
                405                 410                 415

Thr Ala Leu Ser Arg Ile Ala Gly Leu Cys Asn Arg Ala Val Phe Lys
                420                 425                 430

Ala Gly Gln Glu Asn Ile Ser Val Ser Lys Arg Asp Thr Ala Gly Asp
        435                 440                 445

Ala Ser Glu Ser Ala Leu Leu Lys Cys Ile Glu Leu Ser Cys Gly Ser
        450                 455                 460

Val Arg Lys Met Arg Asp Arg Asn Pro Lys Val Ala Glu Ile Pro Phe
465                 470                 475                 480

Asn Ser Thr Asn Lys Tyr Gln Leu Ser Ile His Glu Arg Glu Asp Ser
                485                 490                 495

Pro Gln Ser His Val Leu Val Met Lys Gly Ala Pro Glu Arg Ile Leu
                500                 505                 510

Asp Arg Cys Ser Thr Ile Leu Val Gln Gly Lys Glu Ile Pro Leu Asp
        515                 520                 525

Lys Glu Met Gln Asp Ala Phe Gln Asn Ala Tyr Met Glu Leu Gly Gly
        530                 535                 540

Leu Gly Glu Arg Val Leu Gly Phe Cys Gln Leu Asn Leu Pro Ser Gly
545                 550                 555                 560

Lys Phe Pro Arg Gly Phe Lys Phe Asp Thr Asp Glu Leu Asn Phe Pro
                565                 570                 575

Thr Glu Lys Leu Cys Phe Val Gly Leu Met Ser Met Ile Asp Pro Pro
                580                 585                 590

Arg Ala Ala Val Pro Asp Ala Val Gly Lys Cys Arg Ser Ala Gly Ile
        595                 600                 605
```

```
Lys Val Ile Met Val Thr Gly Asp His Pro Ile Thr Ala Lys Ala Ile
610                 615                 620

Ala Lys Gly Val Gly Ile Ile Ser Glu Gly Asn Glu Thr Val Glu Asp
625                 630                 635                 640

Ile Ala Ala Arg Leu Asn Ile Pro Met Ser Gln Val Asn Pro Arg Glu
                645                 650                 655

Ala Lys Ala Cys Val Val His Gly Ser Asp Leu Lys Asp Met Thr Ser
                660                 665                 670

Glu Gln Leu Asp Glu Ile Leu Lys Asn His Thr Glu Ile Val Phe Ala
                675                 680                 685

Arg Thr Ser Pro Gln Gln Lys Leu Ile Ile Val Glu Gly Cys Gln Arg
690                 695                 700

Gln Gly Ala Ile Val Ala Val Thr Gly Asp Gly Val Asn Asp Ser Pro
705                 710                 715                 720

Ala Leu Lys Lys Ala Asp Ile Gly Ile Ala Met Gly Ile Ser Gly Ser
                725                 730                 735

Asp Val Ser Lys Gln Ala Ala Asp Met Ile Leu Leu Asp Asp Asn Phe
                740                 745                 750

Ala Ser Ile Val Thr Gly Val Glu Glu Gly Arg Leu Ile Phe Asp Asn
                755                 760                 765

Leu Lys Lys Ser Ile Ala Tyr Thr Leu Thr Ser Asn Ile Pro Glu Ile
770                 775                 780

Thr Pro Phe Leu Leu Phe Ile Ile Ala Asn Ile Pro Leu Pro Leu Gly
785                 790                 795                 800

Thr Val Thr Ile Leu Cys Ile Asp Leu Gly Thr Asp Met Val Pro Ala
                805                 810                 815

Ile Ser Leu Ala Tyr Glu Ala Ala Glu Ser Asp Ile Met Lys Arg Gln
                820                 825                 830

Pro Arg Asn Ser Gln Thr Asp Lys Leu Val Asn Glu Arg Leu Ile Ser
                835                 840                 845

Met Ala Tyr Gly Gln Ile Gly Met Ile Gln Ala Leu Gly Gly Phe Phe
850                 855                 860

Thr Tyr Phe Val Ile Leu Ala Glu Asn Gly Phe Leu Pro Ser Arg Leu
865                 870                 875                 880

Leu Gly Ile Arg Leu Asp Trp Asp Asp Arg Thr Met Asn Asp Leu Glu
                885                 890                 895

Asp Ser Tyr Gly Gln Glu Trp Thr Tyr Glu Gln Arg Lys Val Val Glu
                900                 905                 910

Phe Thr Cys His Thr Ala Phe Phe Ala Ser Ile Val Val Gln Trp
                915                 920                 925

Ala Asp Leu Ile Ile Cys Lys Thr Arg Arg Asn Ser Val Phe Gln Gln
930                 935                 940

Gly Met Lys Asn Lys Ile Leu Ile Phe Gly Leu Leu Glu Glu Thr Ala
945                 950                 955                 960

Leu Ala Ala Phe Leu Ser Tyr Cys Pro Gly Met Gly Val Ala Leu Arg
                965                 970                 975

Met Tyr Pro Leu Lys Val Thr Trp Trp Phe Cys Ala Phe Pro Tyr Ser
                980                 985                 990

Leu Leu Ile Phe Ile Tyr Asp Glu Val Arg Lys Leu Ile Leu Arg Arg
                995                 1000                1005

Tyr Pro Gly Gly Trp Val Glu Lys Glu Thr Tyr Tyr
    1010            1015            1020
```

<210> SEQ ID NO 26
<211> LENGTH: 1026
<212> TYPE: PRT
<213> ORGANISM: Homo sapiens

<400> SEQUENCE: 26

```
Met Gly Ser Gly Gly Ser Asp Ser Tyr Arg Ile Ala Thr Ser Gln Asp
1               5                   10                  15

Lys Lys Asp Asp Lys Asp Ser Pro Lys Lys Asn Lys Gly Lys Glu Arg
            20                  25                  30

Arg Asp Leu Asp Asp Leu Lys Lys Glu Val Ala Met Thr Glu His Lys
        35                  40                  45

Met Ser Val Glu Glu Val Cys Arg Lys Tyr Asn Thr Asp Cys Val Gln
50                  55                  60

Gly Leu Thr His Ser Lys Ala Gln Glu Ile Leu Ala Arg Asp Gly Pro
65                  70                  75                  80

Asn Ala Leu Thr Pro Pro Thr Thr Pro Glu Trp Val Lys Phe Cys
            85                  90                  95

Arg Gln Leu Phe Gly Gly Phe Ser Ile Leu Leu Trp Ile Gly Ala Ile
            100                 105                 110

Leu Cys Phe Leu Ala Tyr Gly Ile Gln Ala Gly Thr Glu Asp Asp Pro
        115                 120                 125

Ser Gly Asp Asn Leu Tyr Leu Gly Ile Val Leu Ala Ala Val Val Ile
130                 135                 140

Ile Thr Gly Cys Phe Ser Tyr Tyr Gln Glu Ala Lys Ser Ser Lys Ile
145                 150                 155                 160

Met Glu Ser Phe Lys Asn Met Val Pro Gln Gln Ala Leu Val Ile Arg
            165                 170                 175

Glu Gly Glu Lys Met Gln Val Asn Ala Glu Glu Val Val Val Gly Asp
            180                 185                 190

Leu Val Glu Ile Lys Gly Gly Asp Arg Val Pro Ala Asp Leu Arg Ile
        195                 200                 205

Ile Ser Ala His Gly Cys Lys Val Asp Asn Ser Ser Leu Thr Gly Glu
210                 215                 220

Ser Glu Pro Gln Thr Arg Ser Pro Asp Cys Thr His Asp Asn Pro Leu
225                 230                 235                 240

Glu Thr Arg Asn Ile Thr Phe Phe Ser Thr Asn Cys Val Glu Gly Thr
            245                 250                 255

Ala Arg Gly Val Val Val Ala Thr Gly Asp Arg Thr Val Met Gly Arg
            260                 265                 270

Ile Ala Thr Leu Ala Ser Gly Leu Glu Val Gly Lys Thr Pro Ile Ala
        275                 280                 285

Ile Glu Ile Glu His Phe Ile Gln Leu Ile Thr Gly Val Ala Val Phe
290                 295                 300

Leu Gly Val Ser Phe Phe Ile Leu Ser Leu Ile Leu Gly Tyr Thr Trp
305                 310                 315                 320

Leu Glu Ala Val Ile Phe Leu Ile Gly Ile Ile Val Ala Asn Val Pro
            325                 330                 335

Glu Gly Leu Leu Ala Thr Val Thr Val Cys Leu Thr Leu Thr Ala Lys
            340                 345                 350

Arg Met Ala Arg Lys Asn Cys Leu Val Lys Asn Leu Glu Ala Val Glu
        355                 360                 365

Thr Leu Gly Ser Thr Ser Thr Ile Cys Ser Asp Lys Thr Gly Thr Leu
370                 375                 380
```

```
Thr Gln Asn Arg Met Thr Val Ala His Met Trp Phe Asp Asn Gln Ile
385                 390                 395                 400

His Glu Ala Asp Thr Thr Glu Asp Gln Ser Gly Thr Ser Phe Asp Lys
            405                 410                 415

Ser Ser His Thr Trp Val Ala Leu Ser His Ile Ala Gly Leu Cys Asn
        420                 425                 430

Arg Ala Val Phe Lys Gly Gly Gln Asp Asn Ile Pro Val Leu Lys Arg
        435                 440                 445

Asp Val Ala Gly Asp Ala Ser Glu Ser Ala Leu Leu Lys Cys Ile Glu
    450                 455                 460

Leu Ser Ser Gly Ser Val Lys Leu Met Arg Glu Arg Asn Lys Lys Val
465                 470                 475                 480

Ala Glu Ile Pro Phe Asn Ser Thr Asn Lys Tyr Gln Leu Ser Ile His
                485                 490                 495

Glu Thr Glu Asp Pro Asn Asp Asn Arg Tyr Leu Leu Val Met Lys Gly
            500                 505                 510

Ala Pro Glu Arg Ile Leu Asp Arg Cys Ser Thr Ile Leu Leu Gln Gly
        515                 520                 525

Lys Glu Gln Pro Leu Asp Glu Glu Met Lys Glu Ala Phe Gln Asn Ala
530                 535                 540

Tyr Leu Glu Leu Gly Gly Leu Gly Glu Arg Val Leu Gly Phe Cys His
545                 550                 555                 560

Tyr Tyr Leu Pro Glu Glu Gln Phe Pro Lys Gly Phe Ala Phe Asp Cys
                565                 570                 575

Asp Asp Val Asn Phe Thr Thr Asp Asn Leu Cys Phe Val Gly Leu Met
            580                 585                 590

Ser Met Ile Asp Pro Pro Arg Ala Ala Val Pro Asp Ala Val Gly Lys
        595                 600                 605

Cys Arg Ser Ala Gly Ile Lys Val Ile Met Val Thr Gly Asp His Pro
        610                 615                 620

Ile Thr Ala Lys Ala Ile Ala Lys Gly Val Gly Ile Ile Ser Glu Gly
625                 630                 635                 640

Asn Glu Thr Val Glu Asp Ile Ala Ala Arg Leu Asn Ile Pro Val Ser
                645                 650                 655

Gln Val Asn Pro Arg Asp Ala Lys Ala Cys Val Ile His Gly Thr Asp
            660                 665                 670

Leu Lys Asp Phe Thr Ser Glu Gln Ile Asp Glu Ile Leu Gln Asn His
        675                 680                 685

Thr Glu Ile Val Phe Ala Arg Thr Ser Pro Gln Gln Lys Leu Ile Ile
        690                 695                 700

Val Glu Gly Cys Gln Arg Gln Gly Ala Ile Val Ala Val Thr Gly Asp
705                 710                 715                 720

Gly Val Asn Asp Ser Pro Ala Leu Lys Lys Ala Asp Ile Gly Val Ala
                725                 730                 735

Met Gly Ile Ala Gly Ser Asp Val Ser Lys Gln Ala Ala Asp Met Ile
            740                 745                 750

Leu Leu Asp Asp Asn Phe Ala Ser Ile Val Thr Gly Val Glu Glu Gly
        755                 760                 765

Arg Leu Ile Phe Asp Asn Leu Lys Lys Ser Ile Ala Tyr Thr Leu Thr
        770                 775                 780

Ser Asn Ile Pro Glu Ile Thr Pro Phe Leu Leu Phe Ile Met Ala Asn
785                 790                 795                 800

Ile Pro Leu Pro Leu Gly Thr Ile Thr Ile Leu Cys Ile Asp Leu Gly
```

```
                        805                 810                 815
Thr Asp Met Val Pro Ala Ile Ser Leu Ala Tyr Glu Ala Ala Glu Ser
                820                 825                 830

Asp Ile Met Lys Arg Gln Pro Arg Asn Pro Arg Thr Asp Lys Leu Val
            835                 840                 845

Asn Glu Arg Leu Ile Ser Met Ala Tyr Gly Gln Ile Gly Met Ile Gln
    850                 855                 860

Ala Leu Gly Gly Phe Phe Ser Tyr Phe Val Ile Leu Ala Glu Asn Gly
865                 870                 875                 880

Phe Leu Pro Gly Asn Leu Val Gly Ile Arg Leu Asn Trp Asp Asp Arg
                885                 890                 895

Thr Val Asn Asp Leu Glu Asp Ser Tyr Gly Gln Gln Trp Thr Tyr Glu
            900                 905                 910

Gln Arg Lys Val Val Glu Phe Thr Cys His Thr Ala Phe Phe Val Ser
        915                 920                 925

Ile Val Val Val Gln Trp Ala Asp Leu Ile Ile Cys Lys Thr Arg Arg
930                 935                 940

Asn Ser Val Phe Gln Gln Gly Met Lys Asn Lys Ile Leu Ile Phe Gly
945                 950                 955                 960

Leu Phe Glu Glu Thr Ala Leu Ala Ala Phe Leu Ser Tyr Cys Pro Gly
                965                 970                 975

Met Asp Val Ala Leu Arg Met Tyr Pro Leu Lys Pro Ser Trp Trp Phe
            980                 985                 990

Cys Ala Phe Pro Tyr Ser Phe Leu Ile Phe Val Tyr Asp Glu Ile Arg
        995                 1000                1005

Lys Leu Ile Leu Arg Arg Asn Pro Gly Gly Trp Val Glu Lys Glu
    1010                1015                1020

Thr Tyr Tyr
    1025

<210> SEQ ID NO 27
<211> LENGTH: 1029
<212> TYPE: PRT
<213> ORGANISM: Homo sapiens

<400> SEQUENCE: 27

Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Met Val Lys
            20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Thr Pro Glu
                85                  90                  95

Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
        115                 120                 125

Phe Asn Glu Glu Pro Thr Lys Asp Asn Leu Tyr Leu Ser Ile Val Leu
    130                 135                 140
```

-continued

```
Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
                165                 170                 175

Ala Leu Val Ile Arg Gly Gly Lys Met Gln Ile Asn Val Gln Glu
            180                 185                 190

Val Val Leu Gly Asp Leu Val Glu Ile Lys Gly Gly Asp Arg Val Pro
        195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
        275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu
            340                 345                 350

Thr Leu Thr Ala Lys Arg Met Ala Arg Lys Asn Cys Leu Val Lys Asn
        355                 360                 365

Leu Glu Ala Val Glu Thr Leu Gly Ser Thr Ser Thr Ile Cys Ser Asp
    370                 375                 380

Lys Thr Gly Thr Leu Thr Gln Asn Arg Met Thr Val Ala His Met Trp
385                 390                 395                 400

Phe Asp Met Thr Val Tyr Glu Ala Asp Thr Thr Glu Glu Gln Thr Gly
                405                 410                 415

Lys Thr Phe Thr Lys Ser Ser Asp Thr Trp Phe Met Leu Ala Arg Ile
            420                 425                 430

Ala Gly Leu Cys Asn Arg Ala Asp Phe Lys Ala Asn Gln Glu Ile Leu
        435                 440                 445

Pro Ile Ala Lys Arg Ala Thr Thr Gly Asp Ala Ser Glu Ser Ala Leu
    450                 455                 460

Leu Lys Phe Ile Glu Gln Ser Tyr Ser Ser Val Ala Glu Met Arg Glu
465                 470                 475                 480

Lys Asn Pro Lys Val Ala Glu Ile Pro Phe Asn Ser Thr Asn Lys Tyr
                485                 490                 495

Gln Met Ser Ile His Leu Arg Glu Asp Ser Ser Gln Thr His Val Leu
            500                 505                 510

Met Met Lys Gly Ala Pro Glu Arg Ile Leu Glu Phe Cys Ser Thr Phe
        515                 520                 525

Leu Leu Asn Gly Gln Glu Tyr Ser Met Asn Asp Glu Met Lys Glu Ala
    530                 535                 540

Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
```

-continued

```
                565                 570                 575
Phe Asn Thr Asp Glu Ile Asn Phe Pro Met Asp Asn Leu Cys Phe Val
                580                 585                 590

Gly Leu Ile Ser Met Ile Asp Pro Arg Ala Ala Val Pro Asp Ala
                595                 600                 605

Val Ser Lys Cys Arg Ser Ala Gly Ile Lys Val Ile Met Val Thr Gly
            610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Val Ala Ala Arg Leu Lys Ile
                645                 650                 655

Pro Ile Ser Lys Val Asp Ala Ser Ala Lys Ala Ile Val Val His
                660                 665                 670

Gly Ala Glu Leu Lys Asp Ile Gln Ser Lys Gln Leu Asp Gln Ile Leu
                675                 680                 685

Gln Asn His Pro Glu Ile Val Phe Ala Arg Thr Ser Pro Gln Gln Lys
                690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
                740                 745                 750

Asp Met Ile Leu Leu Asp Asp Asn Phe Ala Ser Ile Val Thr Gly Val
                755                 760                 765

Glu Glu Gly Arg Leu Ile Phe Asp Asn Leu Lys Lys Ser Ile Met Tyr
                770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
                820                 825                 830

Ala Glu Ser Asp Ile Met Lys Arg Leu Pro Arg Asn Pro Lys Thr Asp
                835                 840                 845

Asn Leu Val Asn His Arg Leu Ile Gly Met Ala Tyr Gly Gln Ile Gly
                850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
                900                 905                 910

Thr Tyr Glu Gln Arg Lys Val Val Glu Phe Thr Cys Gln Thr Ala Phe
                915                 920                 925

Phe Val Thr Ile Val Val Val Gln Trp Ala Asp Leu Ile Ile Ser Lys
930                 935                 940

Thr Arg Arg Asn Ser Leu Phe Gln Gln Gly Met Arg Asn Lys Val Leu
945                 950                 955                 960

Ile Phe Gly Ile Leu Glu Glu Thr Leu Leu Ala Ala Phe Leu Ser Tyr
                965                 970                 975

Thr Pro Gly Met Asp Val Ala Leu Arg Met Tyr Pro Leu Lys Ile Thr
                980                 985                 990
```

```
Trp Trp Leu Cys Ala Ile Pro Tyr Ser Ile Leu Ile Phe Val Tyr Asp
        995                1000                1005

Glu Ile Arg Lys Leu Leu Ile Arg Gln His Pro Asp Gly Trp Val
    1010                1015                1020

Glu Arg Glu Thr Tyr Tyr
    1025

<210> SEQ ID NO 28
<211> LENGTH: 279
<212> TYPE: PRT
<213> ORGANISM: Homo sapiens

<400> SEQUENCE: 28

Met Thr Lys Asn Glu Lys Lys Ser Leu Asn Gln Ser Leu Ala Glu Trp
1               5                   10                  15

Lys Leu Phe Ile Tyr Asn Pro Thr Thr Gly Glu Phe Leu Gly Arg Thr
            20                  25                  30

Ala Lys Ser Trp Gly Leu Ile Leu Phe Tyr Leu Val Phe Tyr Gly
        35                  40                  45

Phe Leu Ala Ala Leu Phe Ser Phe Thr Met Trp Val Met Leu Gln Thr
50                  55                  60

Leu Asn Asp Glu Val Pro Lys Tyr Arg Asp Gln Ile Pro Ser Pro Gly
65                  70                  75                  80

Leu Met Val Phe Pro Lys Pro Val Thr Ala Leu Glu Tyr Thr Phe Ser
                85                  90                  95

Arg Ser Asp Pro Thr Ser Tyr Ala Gly Tyr Ile Glu Asp Leu Lys Lys
                100                 105                 110

Phe Leu Lys Pro Tyr Thr Leu Glu Glu Gln Lys Asn Leu Thr Val Cys
            115                 120                 125

Pro Asp Gly Ala Leu Phe Glu Gln Lys Gly Pro Val Tyr Val Ala Cys
        130                 135                 140

Gln Phe Pro Ile Ser Leu Leu Gln Ala Cys Ser Gly Met Asn Asp Pro
145                 150                 155                 160

Asp Phe Gly Tyr Ser Gln Gly Asn Pro Cys Ile Leu Val Lys Met Asn
                165                 170                 175

Arg Ile Ile Gly Leu Lys Pro Glu Gly Val Pro Arg Ile Asp Cys Val
                180                 185                 190

Ser Lys Asn Glu Asp Ile Pro Asn Val Ala Val Tyr Pro His Asn Gly
            195                 200                 205

Met Ile Asp Leu Lys Tyr Phe Pro Tyr Tyr Gly Lys Lys Leu His Val
        210                 215                 220

Gly Tyr Leu Gln Pro Leu Val Ala Val Gln Val Ser Phe Ala Pro Asn
225                 230                 235                 240

Asn Thr Gly Lys Glu Val Thr Val Glu Cys Lys Ile Asp Gly Ser Ala
                245                 250                 255

Asn Leu Lys Ser Gln Asp Asp Arg Asp Lys Phe Leu Gly Arg Val Met
            260                 265                 270

Phe Lys Ile Thr Ala Arg Ala
        275

<210> SEQ ID NO 29
<211> LENGTH: 1258
<212> TYPE: PRT
<213> ORGANISM: Homo sapiens

<400> SEQUENCE: 29
```

```
Met Gly Asp Met Ala Asn Ser Val Ala Tyr Ser Gly Val Lys Asn
1               5                   10                  15

Ser Leu Lys Glu Ala Asn His Asp Gly Asp Phe Gly Ile Thr Leu Ala
            20                  25                  30

Glu Leu Arg Ala Leu Met Glu Leu Arg Ser Thr Asp Ala Leu Arg Lys
            35                  40                  45

Ile Gln Glu Ser Tyr Gly Asp Val Tyr Gly Ile Cys Thr Lys Leu Lys
50                  55                  60

Thr Ser Pro Asn Glu Gly Leu Ser Gly Asn Pro Ala Asp Leu Glu Arg
65                  70                  75                  80

Arg Glu Ala Val Phe Gly Lys Asn Phe Ile Pro Pro Lys Lys Pro Lys
                85                  90                  95

Thr Phe Leu Gln Leu Val Trp Glu Ala Leu Gln Asp Val Thr Leu Ile
                100                 105                 110

Ile Leu Glu Ile Ala Ala Ile Val Ser Leu Gly Leu Ser Phe Tyr Gln
            115                 120                 125

Pro Pro Glu Gly Asp Asn Ala Leu Cys Gly Glu Val Ser Val Gly Glu
            130                 135                 140

Glu Glu Gly Glu Gly Thr Gly Trp Ile Glu Gly Ala Ala Ile Leu
145                 150                 155                 160

Leu Ser Val Val Cys Val Val Leu Val Thr Ala Phe Asn Asp Trp Ser
                165                 170                 175

Lys Glu Lys Gln Phe Arg Gly Leu Gln Ser Arg Ile Glu Gln Glu Gln
            180                 185                 190

Lys Phe Thr Val Ile Arg Gly Gly Gln Val Ile Gln Ile Pro Val Ala
            195                 200                 205

Asp Ile Thr Val Gly Asp Ile Ala Gln Val Lys Tyr Gly Asp Leu Leu
210                 215                 220

Pro Ala Asp Gly Ile Leu Ile Gln Gly Asn Asp Leu Lys Ile Asp Glu
225                 230                 235                 240

Ser Ser Leu Thr Gly Glu Ser Asp His Val Lys Lys Ser Leu Asp Lys
            245                 250                 255

Asp Pro Leu Leu Leu Ser Gly Thr His Val Met Glu Gly Ser Gly Arg
            260                 265                 270

Met Val Val Thr Ala Val Gly Val Asn Ser Gln Thr Gly Ile Ile Phe
            275                 280                 285

Thr Leu Leu Gly Ala Gly Gly Glu Glu Glu Lys Lys Asp Glu Lys
            290                 295                 300

Lys Lys Glu Lys Lys Asn Lys Lys Gln Asp Gly Ala Ile Glu Asn Arg
305                 310                 315                 320

Asn Lys Ala Lys Ala Gln Asp Gly Ala Ala Met Glu Met Gln Pro Leu
            325                 330                 335

Lys Ser Glu Glu Gly Gly Asp Gly Asp Glu Lys Asp Lys Lys Lys Ala
            340                 345                 350

Asn Leu Pro Lys Lys Glu Lys Ser Val Leu Gln Gly Lys Leu Thr Lys
            355                 360                 365

Leu Ala Val Gln Ile Gly Lys Ala Gly Leu Leu Met Ser Ala Ile Thr
            370                 375                 380

Val Ile Ile Leu Val Leu Tyr Phe Val Ile Asp Thr Phe Trp Val Gln
385                 390                 395                 400

Lys Arg Pro Trp Leu Ala Glu Cys Thr Pro Ile Tyr Ile Gln Tyr Phe
                405                 410                 415
```

```
Val Lys Phe Phe Ile Ile Gly Val Thr Val Leu Val Ala Val Pro
            420                 425                 430

Glu Gly Leu Pro Leu Ala Val Thr Ile Ser Leu Ala Tyr Ser Val Lys
            435                 440                 445

Lys Met Met Lys Asp Asn Asn Leu Val Arg His Leu Asp Ala Cys Glu
            450                 455                 460

Thr Met Gly Asn Ala Thr Ala Ile Cys Ser Asp Lys Thr Gly Thr Leu
465                 470                 475                 480

Thr Met Asn Arg Met Thr Val Val Gln Ala Tyr Ile Asn Glu Lys His
                485                 490                 495

Tyr Lys Lys Val Pro Glu Pro Glu Ala Ile Pro Pro Asn Ile Leu Ser
            500                 505                 510

Tyr Leu Val Thr Gly Ile Ser Val Asn Cys Ala Tyr Thr Ser Lys Ile
            515                 520                 525

Leu Pro Pro Glu Lys Glu Gly Gly Leu Pro Arg His Val Gly Asn Lys
            530                 535                 540

Thr Glu Cys Ala Leu Leu Gly Leu Leu Leu Asp Leu Lys Arg Asp Tyr
545                 550                 555                 560

Gln Asp Val Arg Asn Glu Ile Pro Glu Glu Ala Leu Tyr Lys Val Tyr
                565                 570                 575

Thr Phe Asn Ser Val Arg Lys Ser Met Ser Thr Val Leu Lys Asn Ser
            580                 585                 590

Asp Gly Ser Tyr Arg Ile Phe Ser Lys Gly Ala Ser Glu Ile Ile Leu
            595                 600                 605

Lys Lys Cys Phe Lys Ile Leu Ser Ala Asn Gly Glu Ala Lys Val Phe
610                 615                 620

Arg Pro Arg Asp Arg Asp Ile Val Lys Thr Val Ile Glu Pro Met
625                 630                 635                 640

Ala Ser Glu Gly Leu Arg Thr Ile Cys Leu Ala Phe Arg Asp Phe Pro
                645                 650                 655

Ala Gly Glu Pro Glu Pro Glu Trp Asp Asn Glu Asn Asp Ile Val Thr
            660                 665                 670

Gly Leu Thr Cys Ile Ala Val Val Gly Ile Glu Asp Pro Val Arg Pro
            675                 680                 685

Glu Val Pro Asp Ala Ile Lys Lys Cys Gln Arg Ala Gly Ile Thr Val
            690                 695                 700

Arg Met Val Thr Gly Asp Asn Ile Asn Thr Ala Arg Ala Ile Ala Thr
705                 710                 715                 720

Lys Cys Gly Ile Leu His Pro Gly Glu Asp Phe Leu Cys Leu Glu Gly
                725                 730                 735

Lys Asp Phe Asn Arg Arg Ile Arg Asn Glu Lys Gly Glu Ile Glu Gln
            740                 745                 750

Glu Arg Ile Asp Lys Ile Trp Pro Lys Leu Arg Val Leu Ala Arg Ser
            755                 760                 765

Ser Pro Thr Asp Lys His Thr Leu Val Lys Gly Ile Ile Asp Ser Thr
            770                 775                 780

Val Ser Asp Gln Arg Gln Val Val Ala Val Thr Gly Asp Gly Thr Asn
785                 790                 795                 800

Asp Gly Pro Ala Leu Lys Lys Ala Asp Val Gly Phe Ala Met Gly Ile
                805                 810                 815

Ala Gly Thr Asp Val Ala Lys Glu Ala Ser Asp Ile Ile Leu Thr Asp
            820                 825                 830

Asp Asn Phe Thr Ser Ile Val Lys Ala Val Met Trp Gly Arg Asn Val
```

```
                835                 840                 845
Tyr Asp Ser Ile Ser Lys Phe Leu Gln Phe Gln Leu Thr Val Asn Val
            850                 855                 860
Val Ala Val Ile Val Ala Phe Thr Gly Ala Cys Ile Thr Gln Asp Ser
865                 870                 875                 880
Pro Leu Lys Ala Val Gln Met Leu Trp Val Asn Leu Ile Met Asp Thr
                885                 890                 895
Leu Ala Ser Leu Ala Leu Ala Thr Glu Pro Thr Glu Ser Leu Leu
            900                 905                 910
Leu Arg Lys Pro Tyr Gly Arg Asn Lys Pro Leu Ile Ser Arg Thr Met
                915                 920                 925
Met Lys Asn Ile Leu Gly His Ala Phe Tyr Gln Leu Val Val Phe
            930                 935                 940
Thr Leu Leu Phe Ala Gly Glu Lys Phe Phe Asp Ile Asp Ser Gly Arg
945                 950                 955                 960
Asn Ala Pro Leu His Ala Pro Pro Ser Glu His Tyr Thr Ile Val Phe
                965                 970                 975
Asn Thr Phe Val Leu Met Gln Leu Phe Asn Glu Ile Asn Ala Arg Lys
            980                 985                 990
Ile His Gly Glu Arg Asn Val Phe Glu Gly Ile Phe Asn Asn Ala Ile
                995                 1000                1005
Phe Cys Thr Ile Val Leu Gly Thr Phe Val Val Gln Ile Ile Ile
        1010                1015                1020
Val Gln Phe Gly Gly Lys Pro Phe Ser Cys Ser Glu Leu Ser Ile
        1025                1030                1035
Glu Gln Trp Leu Trp Ser Ile Phe Leu Gly Met Gly Thr Leu Leu
        1040                1045                1050
Trp Gly Gln Leu Ile Ser Thr Ile Pro Thr Ser Arg Leu Lys Phe
        1055                1060                1065
Leu Lys Glu Ala Gly His Gly Thr Gln Lys Glu Ile Pro Glu
        1070                1075                1080
Glu Glu Leu Ala Glu Asp Val Glu Glu Ile Asp His Ala Glu Arg
        1085                1090                1095
Glu Leu Arg Arg Gly Gln Ile Leu Trp Phe Arg Gly Leu Asn Arg
        1100                1105                1110
Ile Gln Thr Gln Met Asp Val Val Asn Ala Phe Gln Ser Gly Ser
        1115                1120                1125
Ser Ile Gln Gly Ala Leu Arg Arg Gln Pro Ser Ile Ala Ser Gln
        1130                1135                1140
His His Asp Val Thr Asn Ile Ser Thr Pro Thr His Ile Arg Val
        1145                1150                1155
Val Asn Ala Phe Arg Ser Ser Leu Tyr Glu Gly Leu Glu Lys Pro
        1160                1165                1170
Glu Ser Arg Ser Ser Ile His Asn Phe Met Thr His Pro Glu Phe
        1175                1180                1185
Arg Ile Glu Asp Ser Glu Pro His Ile Pro Leu Ile Asp Asp Thr
        1190                1195                1200
Asp Ala Glu Asp Asp Ala Pro Thr Lys Arg Asn Ser Ser Pro Pro
        1205                1210                1215
Pro Ser Pro Asn Lys Asn Asn Ala Val Asp Ser Gly Ile His
        1220                1225                1230
Leu Thr Ile Glu Met Asn Lys Ser Ala Thr Ser Ser Ser Pro Gly
        1235                1240                1245
```

```
Ser Pro Leu His Ser Leu Glu Thr Ser Leu
    1250                1255

<210> SEQ ID NO 30
<211> LENGTH: 1272
<212> TYPE: PRT
<213> ORGANISM: Homo sapiens

<400> SEQUENCE: 30

Met Gly Asp Met Thr Asn Ser Asp Phe Tyr Ser Lys Asn Gln Arg Asn
1               5                   10                  15

Glu Ser Ser His Gly Gly Glu Phe Gly Cys Thr Met Glu Glu Leu Arg
            20                  25                  30

Ser Leu Met Glu Leu Arg Gly Thr Glu Ala Val Val Lys Ile Lys Glu
        35                  40                  45

Thr Tyr Gly Asp Thr Glu Ala Ile Cys Arg Arg Leu Lys Thr Ser Pro
    50                  55                  60

Val Glu Gly Leu Pro Gly Thr Ala Pro Asp Leu Glu Lys Arg Lys Gln
65                  70                  75                  80

Ile Phe Gly Gln Asn Phe Ile Pro Pro Lys Lys Pro Lys Thr Phe Leu
                85                  90                  95

Gln Leu Val Trp Glu Ala Leu Gln Asp Val Thr Leu Ile Ile Leu Glu
            100                 105                 110

Ile Ala Ala Ile Ile Ser Leu Gly Leu Ser Phe Tyr His Pro Pro Gly
        115                 120                 125

Glu Gly Asn Glu Gly Cys Ala Thr Ala Gln Gly Gly Ala Glu Asp Glu
    130                 135                 140

Gly Glu Ala Glu Ala Gly Trp Ile Glu Gly Ala Ala Ile Leu Leu Ser
145                 150                 155                 160

Val Ile Cys Val Val Leu Val Thr Ala Phe Asn Asp Trp Ser Lys Glu
                165                 170                 175

Lys Gln Phe Arg Gly Leu Gln Ser Arg Ile Glu Gln Glu Gln Lys Phe
            180                 185                 190

Thr Val Val Arg Ala Gly Gln Val Val Gln Ile Pro Val Ala Glu Ile
        195                 200                 205

Val Val Gly Asp Ile Ala Gln Val Lys Tyr Gly Asp Leu Leu Pro Ala
    210                 215                 220

Asp Gly Leu Phe Ile Gln Gly Asn Asp Leu Lys Ile Asp Glu Ser Ser
225                 230                 235                 240

Leu Thr Gly Glu Ser Asp Gln Val Arg Lys Ser Val Asp Lys Asp Pro
                245                 250                 255

Met Leu Leu Ser Gly Thr His Val Met Glu Gly Ser Gly Arg Met Leu
            260                 265                 270

Val Thr Ala Val Gly Val Asn Ser Gln Thr Gly Ile Ile Phe Thr Leu
        275                 280                 285

Leu Gly Ala Gly Gly Glu Glu Glu Lys Lys Asp Lys Lys Gly Val
    290                 295                 300

Lys Lys Gly Asp Gly Leu Gln Leu Pro Ala Ala Asp Gly Ala Ala Ala
305                 310                 315                 320

Ser Asn Ala Ala Asp Ser Ala Asn Ala Ser Leu Val Asn Gly Lys Met
                325                 330                 335

Gln Asp Gly Asn Val Asp Ala Ser Gln Ser Lys Ala Lys Gln Gln Asp
            340                 345                 350

Gly Ala Ala Ala Met Glu Met Gln Pro Leu Lys Ser Ala Glu Gly Gly
```

-continued

```
              355                 360                 365
Asp Ala Asp Arg Lys Lys Ala Ser Met His Lys Lys Glu Lys Ser
    370                 375                 380
Val Leu Gln Gly Lys Leu Thr Lys Leu Ala Val Gln Ile Gly Lys Ala
385                 390                 395                 400
Gly Leu Val Met Ser Ala Ile Thr Val Ile Leu Val Leu Tyr Phe
                405                 410                 415
Thr Val Asp Thr Phe Val Val Asn Lys Lys Pro Trp Leu Pro Glu Cys
            420                 425                 430
Thr Pro Val Tyr Val Gln Tyr Phe Val Lys Phe Phe Ile Ile Gly Val
            435                 440                 445
Thr Val Leu Val Val Ala Val Pro Glu Gly Leu Pro Leu Ala Val Thr
            450                 455                 460
Ile Ser Leu Ala Tyr Ser Val Lys Lys Met Met Lys Asp Asn Asn Leu
465                 470                 475                 480
Val Arg His Leu Asp Ala Cys Glu Thr Met Gly Asn Ala Thr Ala Ile
                485                 490                 495
Cys Ser Asp Lys Thr Gly Thr Leu Thr Thr Asn Arg Met Thr Val Val
            500                 505                 510
Gln Ala Tyr Val Gly Asp Val His Tyr Lys Glu Ile Pro Asp Pro Ser
            515                 520                 525
Ser Ile Asn Thr Lys Thr Met Glu Leu Leu Ile Asn Ala Ile Ala Ile
530                 535                 540
Asn Ser Ala Tyr Thr Thr Lys Ile Leu Pro Pro Glu Lys Glu Gly Ala
545                 550                 555                 560
Leu Pro Arg Gln Val Gly Asn Lys Thr Glu Cys Gly Leu Leu Gly Phe
                565                 570                 575
Val Leu Asp Leu Lys Gln Asp Tyr Glu Pro Val Arg Ser Gln Met Pro
            580                 585                 590
Glu Glu Lys Leu Tyr Lys Val Tyr Thr Phe Asn Ser Val Arg Lys Ser
            595                 600                 605
Met Ser Thr Val Ile Lys Leu Pro Asp Glu Ser Phe Arg Met Tyr Ser
    610                 615                 620
Lys Gly Ala Ser Glu Ile Val Leu Lys Lys Cys Cys Lys Ile Leu Asn
625                 630                 635                 640
Gly Ala Gly Glu Pro Arg Val Phe Arg Pro Arg Asp Arg Asp Glu Met
                645                 650                 655
Val Lys Lys Val Ile Glu Pro Met Ala Cys Asp Gly Leu Arg Thr Ile
                660                 665                 670
Cys Val Ala Tyr Arg Asp Phe Pro Ser Ser Pro Glu Pro Asp Trp Asp
            675                 680                 685
Asn Glu Asn Asp Ile Leu Asn Glu Leu Thr Cys Ile Cys Val Val Gly
    690                 695                 700
Ile Glu Asp Pro Val Arg Pro Glu Val Pro Glu Ala Ile Arg Lys Cys
705                 710                 715                 720
Gln Arg Ala Gly Ile Thr Val Arg Met Val Thr Gly Asp Asn Ile Asn
                725                 730                 735
Thr Ala Arg Ala Ile Ala Ile Lys Cys Gly Ile Ile His Pro Gly Glu
            740                 745                 750
Asp Phe Leu Cys Leu Glu Gly Lys Glu Phe Asn Arg Arg Ile Arg Asn
            755                 760                 765
Glu Lys Gly Glu Ile Glu Gln Glu Arg Ile Asp Lys Ile Trp Pro Lys
    770                 775                 780
```

-continued

```
Leu Arg Val Leu Ala Arg Ser Ser Pro Thr Asp Lys His Thr Leu Val
785                 790                 795                 800

Lys Gly Ile Ile Asp Ser Thr His Thr Glu Gln Arg Gln Val Val Ala
                805                 810                 815

Val Thr Gly Asp Gly Thr Asn Asp Gly Pro Ala Leu Lys Lys Ala Asp
            820                 825                 830

Val Gly Phe Ala Met Gly Ile Ala Gly Thr Asp Val Ala Lys Glu Ala
            835                 840                 845

Ser Asp Ile Ile Leu Thr Asp Asp Asn Phe Ser Ser Ile Val Lys Ala
850                 855                 860

Val Met Trp Gly Arg Asn Val Tyr Asp Ser Ile Ser Lys Phe Leu Gln
865                 870                 875                 880

Phe Gln Leu Thr Val Asn Val Val Ala Val Ile Val Ala Phe Thr Gly
                885                 890                 895

Ala Cys Ile Thr Gln Asp Ser Pro Leu Lys Ala Val Gln Met Leu Trp
            900                 905                 910

Val Asn Leu Ile Met Asp Thr Phe Ala Ser Leu Ala Leu Ala Thr Glu
            915                 920                 925

Pro Pro Thr Glu Thr Leu Leu Leu Arg Lys Pro Tyr Gly Arg Asn Lys
930                 935                 940

Pro Leu Ile Ser Arg Thr Met Met Lys Asn Ile Leu Gly His Ala Val
945                 950                 955                 960

Tyr Gln Leu Ala Leu Ile Phe Thr Leu Leu Phe Val Gly Glu Lys Met
                965                 970                 975

Phe Gln Ile Asp Ser Gly Arg Asn Ala Pro Leu His Ser Pro Pro Ser
            980                 985                 990

Glu His Tyr Thr Ile Ile Phe Asn Thr Phe Val Met Met Gln Leu Phe
            995                 1000                1005

Asn Glu Ile Asn Ala Arg Lys Ile His Gly Glu Arg Asn Val Phe
1010                1015                1020

Asp Gly Ile Phe Arg Asn Pro Ile Phe Cys Thr Ile Val Leu Gly
1025                1030                1035

Thr Phe Ala Ile Gln Ile Val Ile Val Gln Phe Gly Gly Lys Pro
1040                1045                1050

Phe Ser Cys Ser Pro Leu Gln Leu Asp Gln Trp Met Trp Cys Ile
1055                1060                1065

Phe Ile Gly Leu Gly Glu Leu Val Trp Gly Gln Val Ile Ala Thr
1070                1075                1080

Ile Pro Thr Ser Arg Leu Lys Phe Leu Lys Glu Ala Gly Arg Leu
1085                1090                1095

Thr Gln Lys Glu Glu Ile Pro Glu Glu Glu Leu Asn Glu Asp Val
1100                1105                1110

Glu Glu Ile Asp His Ala Glu Arg Glu Leu Arg Arg Gly Gln Ile
1115                1120                1125

Leu Trp Phe Arg Gly Leu Asn Arg Ile Gln Thr Gln Ile Glu Val
1130                1135                1140

Val Asn Thr Phe Lys Ser Gly Ala Ser Phe Gln Gly Ala Leu Arg
1145                1150                1155

Arg Gln Ser Ser Val Thr Ser Gln Ser Gln Asp Ile Arg Val Val
1160                1165                1170

Lys Ala Phe Arg Ser Ser Leu Tyr Glu Gly Leu Glu Lys Pro Glu
1175                1180                1185
```

```
Ser Arg Thr Ser Ile His Asn Phe Met Ala His Pro Glu Phe Arg
    1190                1195                1200

Ile Glu Asp Ser Gln Pro His Ile Pro Leu Ile Asp Asp Thr Asp
    1205                1210                1215

Leu Glu Glu Asp Ala Ala Leu Lys Gln Asn Ser Ser Pro Pro Ser
    1220                1225                1230

Ser Leu Asn Lys Asn Asn Ser Ala Ile Asp Ser Gly Ile Asn Leu
    1235                1240                1245

Thr Thr Asp Thr Ser Lys Ser Ala Thr Ser Ser Pro Gly Ser
    1250                1255                1260

Pro Ile His Ser Leu Glu Thr Ser Leu
    1265                1270

<210> SEQ ID NO 31
<211> LENGTH: 874
<212> TYPE: PRT
<213> ORGANISM: Homo sapiens

<400> SEQUENCE: 31

Met Gly Asp Met Ala Asn Ser Ser Ile Glu Phe His Pro Lys Pro Gln
1               5                   10                  15

Gln Gln Arg Asp Val Pro Gln Ala Gly Phe Gly Cys Thr Leu Ala
                20                  25                  30

Glu Leu Arg Thr Leu Met Glu Leu Arg Gly Ala Glu Ala Leu Gln Lys
            35                  40                  45

Ile Glu Glu Ala Tyr Gly Asp Val Ser Gly Leu Cys Arg Arg Leu Lys
        50                  55                  60

Thr Ser Pro Thr Glu Gly Leu Ala Asp Asn Thr Asn Asp Leu Glu Lys
65                  70                  75                  80

Arg Arg Gln Ile Tyr Gly Gln Asn Phe Ile Pro Pro Lys Gln Pro Lys
                85                  90                  95

Thr Phe Leu Gln Leu Val Trp Glu Ala Leu Gln Asp Val Thr Leu Ile
            100                 105                 110

Ile Leu Glu Val Ala Ala Ile Val Ser Leu Gly Leu Ser Phe Tyr Ala
        115                 120                 125

Pro Pro Gly Glu Glu Ser Glu Ala Cys Gly Asn Val Ser Gly Gly Ala
    130                 135                 140

Glu Asp Glu Gly Glu Ala Glu Ala Gly Trp Ile Glu Gly Ala Ala Ile
145                 150                 155                 160

Leu Leu Ser Val Ile Cys Val Val Leu Val Thr Ala Phe Asn Asp Trp
                165                 170                 175

Ser Lys Glu Lys Gln Phe Arg Gly Leu Gln Ser Arg Ile Glu Gln Glu
            180                 185                 190

Gln Lys Phe Thr Val Ile Arg Asn Gly Gln Leu Leu Gln Val Pro Val
        195                 200                 205

Ala Ala Leu Val Val Gly Asp Ile Ala Gln Val Lys Tyr Gly Asp Leu
    210                 215                 220

Leu Pro Ala Asp Gly Val Leu Ile Gln Ala Asn Asp Leu Lys Ile Asp
225                 230                 235                 240

Glu Ser Ser Leu Thr Gly Glu Ser Asp His Val Arg Lys Ser Ala Asp
                245                 250                 255

Lys Asp Pro Met Leu Leu Ser Gly Thr His Val Met Glu Gly Ser Gly
            260                 265                 270

Arg Met Val Val Thr Ala Val Gly Val Asn Ser Gln Thr Gly Ile Ile
        275                 280                 285
```

```
Phe Thr Leu Leu Gly Ala Gly Glu Glu Glu Lys Lys Asp Lys
    290                 295                 300
Lys Gly Lys Gln Gln Asp Gly Ala Met Glu Ser Ser Gln Thr Lys Ala
305                 310                 315                 320
Lys Lys Gln Asp Gly Ala Val Ala Met Glu Met Gln Pro Leu Lys Ser
                325                 330                 335
Ala Glu Gly Gly Glu Met Glu Glu Arg Glu Lys Lys Lys Ala Asn Ala
                340                 345                 350
Pro Lys Lys Glu Lys Ser Val Leu Gln Gly Lys Leu Thr Lys Leu Ala
            355                 360                 365
Val Gln Ile Gly Lys Ala Gly Leu Val Met Ser Ala Ile Thr Val Ile
    370                 375                 380
Ile Leu Val Leu Tyr Phe Val Ile Glu Thr Phe Val Val Glu Gly Arg
385                 390                 395                 400
Thr Trp Leu Ala Glu Cys Thr Pro Val Tyr Val Gln Tyr Phe Val Lys
                405                 410                 415
Phe Phe Ile Ile Gly Val Thr Val Leu Val Val Ala Val Pro Glu Gly
                420                 425                 430
Leu Pro Leu Ala Val Thr Ile Ser Leu Ala Tyr Ser Val Lys Lys Met
            435                 440                 445
Met Lys Asp Asn Asn Leu Val Arg His Leu Asp Ala Cys Glu Thr Met
    450                 455                 460
Gly Asn Ala Thr Ala Ile Cys Ser Asp Lys Thr Gly Thr Leu Thr Thr
465                 470                 475                 480
Asn Arg Met Thr Val Gln Ser Tyr Leu Gly Asp Thr His Tyr Lys
                485                 490                 495
Glu Ile Pro Ala Pro Ser Ala Leu Thr Pro Lys Ile Leu Asp Leu Leu
                500                 505                 510
Val His Ala Ile Ser Ile Asn Ser Ala Tyr Thr Thr Lys Ile Leu Pro
            515                 520                 525
Pro Glu Lys Glu Gly Ala Leu Pro Arg Gln Val Gly Asn Lys Thr Glu
    530                 535                 540
Cys Ala Leu Leu Gly Phe Val Leu Asp Leu Lys Arg Asp Phe Gln Pro
545                 550                 555                 560
Val Arg Glu Gln Ile Pro Glu Asp Lys Leu Tyr Lys Val Tyr Thr Phe
                565                 570                 575
Asn Ser Val Arg Lys Ser Met Ser Thr Val Ile Arg Met Pro Asp Gly
                580                 585                 590
Gly Phe Arg Leu Phe Ser Lys Gly Ala Ser Glu Ile Leu Leu Lys Lys
            595                 600                 605
Cys Thr Asn Ile Leu Asn Ser Asn Gly Glu Leu Arg Gly Phe Arg Pro
    610                 615                 620
Arg Asp Arg Asp Asp Met Val Arg Lys Ile Ile Glu Pro Met Ala Cys
625                 630                 635                 640
Asp Gly Leu Arg Thr Ile Cys Ile Ala Tyr Arg Asp Phe Ser Ala Gly
                645                 650                 655
Gln Glu Pro Asp Trp Asp Asn Glu Asn Glu Val Val Gly Asp Leu Thr
                660                 665                 670
Cys Ile Ala Val Val Gly Ile Glu Asp Pro Val Arg Pro Glu Val Pro
            675                 680                 685
Glu Ala Ile Arg Lys Cys Gln Arg Ala Gly Ile Thr Val Arg Met Val
    690                 695                 700
```

```
Thr Gly Asp Asn Ile Asn Thr Ala Arg Ala Ile Ala Ala Lys Cys Gly
705                 710                 715                 720

Ile Ile Gln Pro Gly Glu Asp Phe Leu Cys Leu Glu Gly Lys Glu Phe
                725                 730                 735

Asn Arg Arg Ile Arg Asn Glu Lys Gly Glu Ile Glu Gln Glu Arg Leu
            740                 745                 750

Asp Lys Val Trp Pro Lys Leu Arg Val Leu Ala Arg Ser Ser Pro Thr
        755                 760                 765

Asp Lys His Thr Leu Val Lys Gly Ile Ile Asp Ser Thr Thr Gly Glu
    770                 775                 780

Gln Arg Gln Val Val Ala Val Thr Gly Asp Gly Thr Asn Asp Gly Pro
785                 790                 795                 800

Ala Leu Lys Lys Ala Asp Val Gly Phe Ala Met Gly Ile Ala Gly Thr
                805                 810                 815

Asp Val Ala Lys Glu Ala Ser Asp Ile Ile Leu Thr Asp Asp Asn Phe
            820                 825                 830

Thr Ser Ile Val Lys Ala Val Met Trp Gly Arg Asn Val Tyr Asp Ser
        835                 840                 845

Ile Ser Lys Phe Leu Gln Phe Gln Leu Thr Val Asn Val Val Ala Val
    850                 855                 860

Ile Val Ala Phe Thr Gly Ala Cys Ile Thr
865                 870
```

<210> SEQ ID NO 32
<211> LENGTH: 1241
<212> TYPE: PRT
<213> ORGANISM: Homo sapiens

<400> SEQUENCE: 32

```
Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175

Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205
```

```
Gly Asp Ile Ala Gln Val Lys Tyr Gly Asp Leu Leu Pro Ala Asp Gly
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
                245                 250                 255

Leu Ser Gly Thr His Val Met Glu Gly Ser Gly Arg Met Val Val Thr
                260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Gly Lys Lys Gln
290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
                325                 330                 335

Lys Asp Lys Lys Ala Val Lys Val Pro Lys Lys Glu Lys Ser Val Leu
                340                 345                 350

Gln Gly Lys Leu Thr Arg Leu Ala Val Gln Ile Gly Lys Ala Gly Leu
                355                 360                 365

Leu Met Ser Ala Leu Thr Val Phe Ile Leu Ile Leu Tyr Phe Val Ile
        370                 375                 380

Asp Asn Phe Val Ile Asn Arg Arg Pro Trp Leu Pro Glu Cys Thr Pro
385                 390                 395                 400

Ile Tyr Ile Gln Tyr Phe Val Lys Phe Phe Ile Ile Gly Ile Thr Val
                405                 410                 415

Leu Val Val Ala Val Pro Glu Gly Leu Pro Leu Ala Val Thr Ile Ser
                420                 425                 430

Leu Ala Tyr Ser Val Lys Lys Met Met Lys Asp Asn Asn Leu Val Arg
                435                 440                 445

His Leu Asp Ala Cys Glu Thr Met Gly Asn Ala Thr Ala Ile Cys Ser
        450                 455                 460

Asp Lys Thr Gly Thr Leu Thr Met Asn Arg Met Thr Val Val Gln Ala
465                 470                 475                 480

Tyr Ile Gly Gly Ile His Tyr Arg Gln Ile Pro Ser Pro Asp Val Phe
                485                 490                 495

Leu Pro Lys Val Leu Asp Leu Ile Val Asn Gly Ile Ser Ile Asn Ser
                500                 505                 510

Ala Tyr Thr Ser Lys Ile Leu Pro Pro Glu Lys Glu Gly Gly Leu Pro
        515                 520                 525

Arg Gln Val Gly Asn Lys Thr Glu Cys Ala Leu Leu Gly Phe Val Thr
530                 535                 540

Asp Leu Lys Gln Asp Tyr Gln Ala Val Arg Asn Glu Val Pro Glu Glu
545                 550                 555                 560

Lys Leu Tyr Lys Val Tyr Thr Phe Asn Ser Val Arg Lys Ser Met Ser
                565                 570                 575

Thr Val Ile Arg Asn Pro Asn Gly Gly Phe Arg Met Tyr Ser Lys Gly
                580                 585                 590

Ala Ser Glu Ile Ile Leu Arg Lys Cys Asn Arg Ile Leu Asp Arg Lys
        595                 600                 605

Gly Glu Ala Val Pro Phe Lys Asn Lys Asp Arg Asp Met Val Arg
610                 615                 620
```

```
Thr Val Ile Glu Pro Met Ala Cys Asp Gly Leu Arg Thr Ile Cys Ile
625                 630                 635                 640

Ala Tyr Arg Asp Phe Asp Asp Thr Glu Pro Ser Trp Asp Asn Glu Asn
            645                 650                 655

Glu Ile Leu Thr Glu Leu Thr Cys Ile Ala Val Val Gly Ile Glu Asp
                660                 665                 670

Pro Val Arg Pro Glu Val Pro Asp Ala Ile Ala Lys Cys Lys Gln Ala
            675                 680                 685

Gly Ile Thr Val Arg Met Val Thr Gly Asp Asn Ile Asn Thr Ala Arg
    690                 695                 700

Ala Ile Ala Thr Lys Cys Gly Ile Leu Thr Pro Gly Asp Asp Phe Leu
705                 710                 715                 720

Cys Leu Glu Gly Lys Glu Phe Asn Arg Leu Ile Arg Asn Glu Lys Gly
                725                 730                 735

Glu Val Glu Gln Glu Lys Leu Asp Lys Ile Trp Pro Lys Leu Arg Val
            740                 745                 750

Leu Ala Arg Ser Ser Pro Thr Asp Lys His Thr Leu Val Lys Gly Ile
    755                 760                 765

Ile Asp Ser Thr Val Gly Glu His Arg Gln Val Ala Val Thr Gly
770                 775                 780

Asp Gly Thr Asn Asp Gly Pro Ala Leu Lys Lys Ala Asp Val Gly Phe
785                 790                 795                 800

Ala Met Gly Ile Ala Gly Thr Asp Val Ala Lys Glu Ala Ser Asp Ile
                805                 810                 815

Ile Leu Thr Asp Asp Asn Phe Thr Ser Ile Val Lys Ala Val Met Trp
            820                 825                 830

Gly Arg Asn Val Tyr Asp Ser Ile Ser Lys Phe Leu Gln Phe Gln Leu
    835                 840                 845

Thr Val Asn Val Val Ala Val Ile Val Ala Phe Thr Gly Ala Cys Ile
850                 855                 860

Thr Gln Asp Ser Pro Leu Lys Ala Val Gln Met Leu Trp Val Asn Leu
865                 870                 875                 880

Ile Met Asp Thr Phe Ala Ser Leu Ala Leu Ala Thr Glu Pro Pro Thr
                885                 890                 895

Glu Ser Leu Leu Lys Arg Arg Pro Tyr Gly Arg Asn Lys Pro Leu Ile
            900                 905                 910

Ser Arg Thr Met Met Lys Asn Ile Leu Gly His Ala Phe Tyr Gln Leu
    915                 920                 925

Ile Val Ile Phe Ile Leu Val Phe Ala Gly Glu Lys Phe Phe Asp Ile
930                 935                 940

Asp Ser Gly Arg Lys Ala Pro Leu His Ser Pro Ser Gln His Tyr
945                 950                 955                 960

Thr Ile Val Phe Asn Thr Phe Val Leu Met Gln Leu Phe Asn Glu Ile
                965                 970                 975

Asn Ser Arg Lys Ile His Gly Lys Asn Val Phe Ser Gly Ile Tyr
            980                 985                 990

Arg Asn Ile Ile Phe Cys Ser Val  Val Leu Gly Thr Phe  Ile Cys Gln
    995                 1000                1005

Ile Phe  Ile Val Glu Phe  Gly  Gly Lys Pro Phe  Ser  Cys Thr Ser
    1010                1015               1020

Leu Ser  Leu Ser Gln Trp Leu Trp Cys Leu Phe Ile  Gly Ile Gly
    1025               1030               1035

Glu Leu  Leu Trp Gly Gln Phe  Ile Ser Ala Ile Pro  Thr Arg Ser
```

```
                    1040                1045                1050

Leu Lys Phe Leu Lys Glu Ala Gly His Gly Thr Thr Lys Glu Glu
        1055                1060                1065

Ile Thr Lys Asp Ala Glu Gly Leu Asp Glu Ile Asp His Ala Glu
    1070                1075                1080

Met Glu Leu Arg Arg Gly Gln Ile Leu Trp Phe Arg Gly Leu Asn
1085                1090                1095

Arg Ile Gln Thr Gln Ile Asp Val Ile Asn Thr Phe Gln Thr Gly
    1100                1105                1110

Ala Ser Phe Lys Gly Val Leu Arg Arg Gln Asn Met Gly Gln His
    1115                1120                1125

Leu Asp Val Lys Leu Val Pro Ser Ser Ser Tyr Ile Lys Val Val
    1130                1135                1140

Lys Ala Phe His Ser Ser Leu His Glu Ser Ile Gln Lys Pro Tyr
    1145                1150                1155

Asn Gln Lys Ser Ile His Ser Phe Met Thr His Pro Glu Phe Ala
    1160                1165                1170

Ile Glu Glu Glu Leu Pro Arg Thr Pro Leu Leu Asp Glu Glu Glu
    1175                1180                1185

Glu Glu Asn Pro Asp Lys Ala Ser Lys Phe Gly Thr Arg Val Leu
    1190                1195                1200

Leu Leu Asp Gly Glu Val Thr Pro Tyr Ala Asn Thr Asn Asn Asn
    1205                1210                1215

Ala Val Asp Cys Asn Gln Val Gln Leu Pro Gln Ser Asp Ser Ser
    1220                1225                1230

Leu Gln Ser Leu Glu Thr Ser Val
    1235                1240

<210> SEQ ID NO 33
<211> LENGTH: 193
<212> TYPE: PRT
<213> ORGANISM: Homo sapiens

<400> SEQUENCE: 33

Gly Pro Ile Phe Asn Ala Ser Val His Ser Asp Thr Pro Ser Val Ile
1               5                   10                  15

Arg Gly Asp Leu Ile Lys Leu Phe Cys Ile Ile Thr Val Glu Gly Ala
            20                  25                  30

Ala Leu Asp Pro Asp Asp Met Ala Phe Asp Val Ser Trp Phe Ala Val
        35                  40                  45

His Ser Phe Gly Leu Asp Lys Ala Pro Val Leu Leu Ser Ser Leu Asp
    50                  55                  60

Arg Lys Gly Ile Val Thr Thr Ser Arg Arg Asp Trp Lys Ser Asp Leu
65                  70                  75                  80

Ser Leu Glu Arg Val Ser Val Leu Glu Phe Leu Leu Gln Val His Gly
                85                  90                  95

Ser Glu Asp Gln Asp Phe Gly Asn Tyr Tyr Cys Ser Val Thr Pro Trp
            100                 105                 110

Val Lys Ser Pro Thr Gly Ser Trp Gln Lys Glu Ala Glu Ile His Ser
        115                 120                 125

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160
```

```
Ser Cys Leu Ile Gly Tyr Cys Ser Ser His Trp Cys Cys Lys Lys Glu
                165                 170                 175

Val Gln Glu Thr Arg Arg Glu Arg Arg Leu Met Ser Met Glu Met
            180                 185                 190

Asp

<210> SEQ ID NO 34
<211> LENGTH: 1021
<212> TYPE: PRT
<213> ORGANISM: Homo sapiens

<400> SEQUENCE: 34

Met Ala Gly Ile Ser Tyr Val Ala Ser Phe Phe Leu Leu Leu Thr Lys
1               5                   10                  15

Leu Ser Ile Gly Gln Arg Glu Val Thr Val Gln Lys Gly Pro Leu Phe
                20                  25                  30

Arg Ala Glu Gly Tyr Pro Val Ser Ile Gly Cys Asn Val Thr Gly His
            35                  40                  45

Gln Gly Pro Ser Glu Gln His Phe Gln Trp Ser Val Tyr Leu Pro Thr
        50                  55                  60

Asn Pro Thr Gln Glu Val Gln Ile Ile Ser Thr Lys Asp Ala Ala Phe
65                  70                  75                  80

Ser Tyr Ala Val Tyr Thr Gln Arg Val Arg Ser Gly Asp Val Tyr Val
                85                  90                  95

Glu Arg Val Gln Gly Asn Ser Val Leu Leu His Ile Ser Lys Leu Gln
            100                 105                 110

Met Lys Asp Ala Gly Glu Tyr Glu Cys His Thr Pro Asn Thr Asp Glu
        115                 120                 125

Lys Tyr Tyr Gly Ser Tyr Ser Ala Lys Thr Asn Leu Ile Val Ile Pro
130                 135                 140

Asp Thr Leu Ser Ala Thr Met Ser Ser Gln Thr Leu Gly Lys Glu Glu
145                 150                 155                 160

Gly Glu Pro Leu Ala Leu Thr Cys Glu Ala Ser Lys Ala Thr Ala Gln
                165                 170                 175

His Thr His Leu Ser Val Thr Trp Tyr Leu Thr Gln Asp Gly Gly Gly
            180                 185                 190

Ser Gln Ala Thr Glu Ile Ile Ser Leu Ser Lys Asp Phe Ile Leu Val
        195                 200                 205

Pro Gly Pro Leu Tyr Thr Glu Arg Phe Ala Ala Ser Asp Val Gln Leu
210                 215                 220

Asn Lys Leu Gly Pro Thr Thr Phe Arg Leu Ser Ile Glu Arg Leu Gln
225                 230                 235                 240

Ser Ser Asp Gln Gly Gln Leu Phe Cys Glu Ala Thr Glu Trp Ile Gln
                245                 250                 255

Asp Pro Asp Glu Thr Trp Met Phe Ile Thr Lys Lys Gln Thr Asp Gln
            260                 265                 270

Thr Thr Leu Arg Ile Gln Pro Ala Val Lys Asp Phe Gln Val Asn Ile
        275                 280                 285

Thr Ala Asp Ser Leu Phe Ala Glu Gly Lys Pro Leu Glu Leu Val Cys
290                 295                 300

Leu Val Val Ser Ser Gly Arg Asp Pro Gln Leu Gln Gly Ile Trp Phe
305                 310                 315                 320

Phe Asn Gly Thr Glu Ile Ala His Ile Asp Ala Gly Gly Val Leu Gly
                325                 330                 335
```

-continued

Leu Lys Asn Asp Tyr Lys Glu Arg Ala Ser Gln Gly Glu Leu Gln Val
            340                 345                 350

Ser Lys Leu Gly Pro Lys Ala Phe Ser Leu Lys Ile Phe Ser Leu Gly
        355                 360                 365

Pro Glu Asp Glu Gly Ala Tyr Arg Cys Val Val Ala Glu Val Met Lys
    370                 375                 380

Thr Arg Thr Gly Ser Trp Gln Val Leu Gln Arg Lys Gln Ser Pro Asp
385                 390                 395                 400

Ser His Val His Leu Arg Lys Pro Ala Ala Arg Ser Val Val Met Ser
                405                 410                 415

Thr Lys Asn Lys Gln Gln Val Val Trp Glu Gly Glu Thr Leu Ala Phe
            420                 425                 430

Leu Cys Lys Ala Gly Gly Ala Glu Ser Pro Leu Ser Val Ser Trp Trp
        435                 440                 445

His Ile Pro Arg Asp Gln Thr Gln Pro Glu Phe Val Ala Gly Met Gly
    450                 455                 460

Gln Asp Gly Ile Val Gln Leu Gly Ala Ser Tyr Gly Val Pro Ser Tyr
465                 470                 475                 480

His Gly Asn Thr Arg Leu Glu Lys Met Asp Trp Ala Thr Phe Gln Leu
                485                 490                 495

Glu Ile Thr Phe Thr Ala Ile Thr Asp Ser Gly Thr Tyr Glu Cys Arg
            500                 505                 510

Val Ser Glu Lys Ser Arg Asn Gln Ala Arg Asp Leu Ser Trp Thr Gln
        515                 520                 525

Lys Ile Ser Val Thr Val Lys Ser Leu Glu Ser Ser Leu Gln Val Ser
    530                 535                 540

Leu Met Ser Arg Gln Pro Gln Val Met Leu Thr Asn Thr Phe Asp Leu
545                 550                 555                 560

Ser Cys Val Val Arg Ala Gly Tyr Ser Asp Leu Lys Val Pro Leu Thr
                565                 570                 575

Val Thr Trp Gln Phe Gln Pro Ala Ser Ser His Ile Phe His Gln Leu
            580                 585                 590

Ile Arg Ile Thr His Asn Gly Thr Ile Glu Trp Gly Asn Phe Leu Ser
        595                 600                 605

Arg Phe Gln Lys Lys Thr Lys Val Ser Gln Ser Leu Phe Arg Ser Gln
    610                 615                 620

Leu Leu Val His Asp Ala Thr Glu Glu Thr Gly Val Tyr Gln Cys
625                 630                 635                 640

Glu Val Glu Val Tyr Asp Arg Asn Ser Leu Tyr Asn Asn Arg Pro Pro
                645                 650                 655

Arg Ala Ser Ala Ile Ser His Pro Leu Arg Ile Ala Val Thr Leu Pro
            660                 665                 670

Glu Ser Lys Leu Lys Val Asn Ser Arg Ser Gln Val Gln Glu Leu Ser
        675                 680                 685

Ile Asn Ser Asn Thr Asp Ile Glu Cys Ser Ile Leu Ser Arg Ser Asn
    690                 695                 700

Gly Asn Leu Gln Leu Ala Ile Ile Trp Tyr Phe Ser Pro Val Ser Thr
705                 710                 715                 720

Asn Ala Ser Trp Leu Lys Ile Leu Glu Met Asp Gln Thr Asn Val Ile
                725                 730                 735

Lys Thr Gly Asp Glu Phe His Thr Pro Gln Arg Lys Gln Lys Phe His
            740                 745                 750

Thr Glu Lys Val Ser Gln Asp Leu Phe Gln Leu His Ile Leu Asn Val

```
                755                 760                 765
Glu Asp Ser Asp Arg Gly Lys Tyr His Cys Ala Val Glu Glu Trp Leu
    770                 775                 780
Leu Ser Thr Asn Gly Thr Trp His Lys Leu Gly Lys Lys Ser Gly
785                 790                 795                 800
Leu Thr Glu Leu Lys Leu Lys Pro Thr Gly Ser Lys Val Arg Val Ser
                805                 810                 815
Lys Val Tyr Trp Thr Glu Asn Val Thr Glu His Arg Glu Val Ala Ile
            820                 825                 830
Arg Cys Ser Leu Glu Ser Val Gly Ser Ser Ala Thr Leu Tyr Ser Val
                835                 840                 845
Met Trp Tyr Trp Asn Arg Glu Asn Ser Gly Ser Lys Leu Leu Val His
    850                 855                 860
Leu Gln His Asp Gly Leu Leu Glu Tyr Gly Glu Gly Leu Arg Arg
865                 870                 875                 880
His Leu His Cys Tyr Arg Ser Ser Thr Asp Phe Val Leu Lys Leu
                885                 890                 895
His Gln Val Glu Met Glu Asp Ala Gly Met Tyr Trp Cys Arg Val Ala
            900                 905                 910
Glu Trp Gln Leu His Gly His Pro Ser Lys Trp Ile Asn Gln Ala Ser
                915                 920                 925
Asp Glu Ser Gln Arg Met Val Leu Thr Val Leu Pro Ser Glu Pro Thr
    930                 935                 940
Leu Pro Ser Arg Ile Cys Ser Ser Ala Pro Leu Leu Tyr Phe Leu Phe
945                 950                 955                 960
Ile Cys Pro Phe Val Leu Leu Leu Leu Leu Ile Ser Leu Leu Cys
                965                 970                 975
Leu Tyr Trp Lys Ala Arg Lys Leu Ser Thr Leu Arg Ser Asn Thr Arg
            980                 985                 990
Lys Glu Lys Ala Leu Trp Val Asp  Leu Lys Glu Ala Gly  Gly Val Thr
                995                 1000                1005
Thr Asn  Arg Arg Glu Asp Glu  Glu Glu Asp Glu Gly  Asn
    1010                1015                1020

<210> SEQ ID NO 35
<211> LENGTH: 20
<212> TYPE: PRT
<213> ORGANISM: Homo sapiens

<400> SEQUENCE: 35

Met Ala Gly Ile Ser Tyr Val Ala Ser Phe Phe Leu Leu Leu Thr Lys
1               5                   10                  15

Leu Ser Ile Gly
            20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgttggcagt ccgccttaac                                                   20

<210> SEQ ID NO 37
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
catagtcact gacgttgcag                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttgtggagct tgcaagcacc                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gttctttatg tggagctcca                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tatcccttgc tgatcggcgt                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctgcagtac ccgatgagac                                                   20

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu His Ser Ala Gly Gly Gly Gly Ser Asp Tyr Lys Asp Asp Asp Asp
1               5                   10                  15

Lys Gly Gly Gly Gly Ser Leu Ser Asn Pro Ile Glu Ile Asp Phe Gln
            20                  25                  30
```

```
Thr Ser Gly Pro Ile Phe
        35

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu His Ser Ala Gly Gly Gly Gly Ser Asp Tyr Lys Asp Asp Asp Asp
1               5                   10                  15

Lys Gly Gly Gly Gly Ser Ile Glu Ile Asp Phe Gln Thr Ser Gly Pro
            20                  25                  30

Ile Phe

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu His Ser Ala Gly Gly Gly Gly Ser Asp Tyr Lys Asp Asp Asp Asp
1               5                   10                  15

Lys Gly Gly Gly Gly Ser Phe Gln Thr Ser Gly Pro Ile Phe
            20                  25                  30

<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu His Ser Ala Gly Gly Gly Gly Ser Asp Tyr Lys Asp Asp Asp Asp
1               5                   10                  15

Lys Gly Gly Gly Gly Ser Gly Pro Ile Phe
            20                  25

<210> SEQ ID NO 46
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Phe Ile Thr Val Lys Met Asp Thr Leu Asp Pro Arg Ser Phe Leu Leu
1               5                   10                  15

Arg Asn Pro Asn Asp Lys Tyr Glu Pro Phe Trp Glu Asp Glu Glu Lys
            20                  25                  30

Asn Glu Ser Gly Ser Asp Lys Thr His Thr
            35                  40
```

PREPARATION OF THERAPEUTIC EXOSOMES USING MEMBRANE PROTEINS

1. CROSS REFERENCE TO RELATED APPLICATIONS

This application is a continuation of U.S. application Ser. No. 16/112,547, filed Aug. 24, 2018, which claims the benefit of U.S. Provisional Application Nos. 62/550,543, filed Aug. 25, 2017, and 62/656,956, filed Apr. 12, 2018, each of which is hereby incorporated in its entirety by reference.

2. SEQUENCE LISTING

The instant application contains a Sequence Listing which has been submitted via EFS-Web and is hereby incorporated by reference in its entirety. Said ASCII copy, created on Dec. 20, 2018, is named 42224US_CRF_sequencelisting.txt, and is 175,129 bytes in size.

3. BACKGROUND

Exosomes are important mediators of intercellular communication. They are also important biomarkers in the diagnosis and prognosis of many diseases, such as cancer. As drug delivery vehicles, exosomes offer many advantages over traditional drug delivery methods as a new treatment modality in many therapeutic areas.

The use of exosomes for therapeutic purposes requires that exosomes be free or mostly free of impurities including but not limited to contaminant proteins, DNA, carbohydrates, and lipids. Current purification methods do not offer sufficient selectivity to remove significant amounts of these impurities so additional processes are desired to improve purity.

Furthermore, as exosomes become more frequently used in the treatment of human disease, they may struggle to meet clinical expectations because of heterogeneity in their physicochemical parameters that confer molecular targeting, immune evasion, and controlled drug release. This is mainly due to the heterogeneity and complexity of exosome properties (e.g., composition, size, shape, rigidity, surface charge, hydrophilicity, stability, and ligand type and density), payload properties (e.g., drug type, solubility, loading, potency, dosing, immune response, and release kinetics), and in vivo physiological barriers to exosome trafficking (e.g., immune surveillance, particle extravasation, tissue targeting, tissue penetration, and cellular uptake). Although a considerable amount of effort has been made, effective methods for obtaining discrete sub-populations of therapeutic exosomes with desired properties, e.g., exosomes containing therapeutic payloads and having appropriate targeting moieties, are not yet readily available.

Suitable methods for generating, isolating and purifying discrete sub-populations of exosomes are needed to better enable therapeutic use and other applications of exosome-based technologies.

4. SUMMARY

An aspect of the present invention relates to novel methods of preparing exosomes for therapeutic use. Specifically, the methods use surface markers that are newly identified to be enriched on the surface of exosomes. In particular, a group of proteins (e.g., prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4)) were identified to be highly enriched on the surface of exosomes.

The newly-identified proteins can be used in various embodiments of the present invention. One aspect of the present invention relates to generating a fusion protein by conjugating the newly-identified exosome protein and a therapeutic protein, and producing an engineered exosome containing the fusion protein on the surface. A native full-length or a biologically active fragment of the therapeutic protein can be transported to the surface of exosomes by being conjugated to the exosome-enriched proteins. The method using the newly-identified exosome proteins as provided herein are better at producing surface engineered exosomes than methods using some other exosome scaffold protein known in the art (e.g., Lamp2B, PDGFR, lactadherin CD9, CD63 and/or CD81, or fragments thereof). Without wishing to be bound by a theory, it is believed that the newly-identified proteins are better because several of the exosome scaffold proteins known in the art—i.e., tetraspannin proteins such as CD9, CD63 and CD81, have both of their C- and N-termini in the exosome lumen.

Another aspect of the present invention relates to purification of an exosome by affinity purification from a heterogeneous solution such as cell culture media or plasma using the exosome proteins that are common to all exosomes, or common to all exosomes derived from a single cell type. Some embodiments relate to isolation of a sub-population of exosomes from the total exosomes by using surface markers specific to a sub-population of exosomes.

Another aspect of the present invention relates to methods of removing exosomes from a sample when exosomes are a contaminating product. For example, natural or engineered viruses may be purified from contaminating exosomes. The exosome proteins described herein thus can be used to selectively remove exosomes from biological processes where other particles of similar size, shape, and/or charge are the desirable product.

Another aspect of the present invention relates to generation or use of a surface-engineered exosome designed for more efficient affinity purification, or for presentation of a targeting moiety or a therapeutically relevant protein on the surface. For example, the exosome surfaces can be modified to contain the native full-length exosome protein and/or a fragment or a modified protein of the native exosome protein on the surface at a higher density.

The present invention further relates to a producer cell or a method of generating the producer cell for producing such a surface-engineered exosome. An exogenous polynucleotide can be introduced transiently or stably into a producer cell to make the producer cell to generate a surface-engineered exosome.

Specifically, an aspect of the present invention relates to a method of isolating an exosome, comprising the steps of: (1) providing a sample comprising the exosome; (2) contacting the sample with a binding agent having affinity to a target protein, wherein the target protein comprises PTGFRN, BSG, IGSF2, IGSF3, IGSF8, ITGB1, ITGA4, SLC3A2, ATP transporter or a fragment or a variant thereof; and (3) isolating the exosome based on a binding between the target protein and the binding agent.

In some embodiments, the sample is obtained from a cell grown in vitro, optionally wherein the cell is an HEK293 cell, a Chinese hamster ovary (CHO) cell, or a mesenchymal stem cell (MSC). In some embodiments, the sample is obtained from a body fluid of a subject.

In some embodiments, the cell is genetically modified to express the target protein. In some embodiments, the cell comprises an expression plasmid encoding the target protein. In some embodiments, the cell is genetically modified to comprise an exogenous sequence expressing a tag having affinity to the binding agent, wherein the exogenous sequence is inserted into a genome of the cell. In some embodiments, the exogenous sequence is inserted in a genomic site located at 3' or 5' end of an endogenous sequence encoding PTGFRN, BSG, IGSF2, IGSF3, IGSF8, ITGB1, ITGA4, SLC3A2 or ATP transporter. In some embodiments, the endogenous sequence does not encode IGSF8. In some embodiments, the exogenous sequence is inserted in a genomic site located within an endogenous sequence encoding PTGFRN, BSG, IGSF3, IGSF8, ITGB1, ITGA4, SLC3A2 or ATP transporter.

In some embodiments, the target protein is a fusion protein comprising the tag, and PTGFRN, BSG, IGSF2, IGSF3, IGSF8, ITGB1, ITGA4, SLC3A2, ATP transporter or a fragment or a variant thereof. In some embodiments, the exosome comprises the target protein. In some embodiments, the target protein is not IGSF8 or a fragment or modification thereof. In some embodiments, the cell is genetically modified to have a reduced expression of ADAM10.

In some embodiments, the exosome comprises the target protein. In some embodiments, the target protein is selected from PTGFRN, BSG, IGSF2, IGSF3, ITGB1, ITGA4, SLC3A2 and ATP transporter. In some embodiments, the target protein comprises a fragment or a variant of PTGFRN, BSG, IGSF2, IGSF3, IGSF8, ITGB1, ITGA4, SLC3A2 or ATP transporter. In some embodiments, the target protein comprises a polypeptide of SEQ ID NO: 33. In some embodiments, the target protein is a fusion protein comprising PTGFRN, BSG, IGSF2, IGSF3, ITGB1, ITGA4, SLC3A2, ATP transporter or a fragment or a variant thereof, and an affinity tag, wherein the affinity tag has affinity to the binding agent. In some embodiments, the target protein does not comprise IGSF8 or a fragment or modification thereof.

In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane.

In some embodiments, the solid support forms a chromatography column. In some embodiments, the step of contacting the sample with the binding agent is performed by applying the sample to the chromatography column.

In some embodiments, the method further comprises the steps of: (1) contacting a subset of the sample with a different binding agent having affinity to a different target protein; and (2) isolating the exosome based on a binding between the different target protein and the different binding agent. In some embodiments, the different target protein comprises PTGFRN, BSG, IGSF2, IGSF3, IGSF8, ATP transporter or a fragment or a variant thereof. In some embodiments, the different target protein comprises a polypeptide of SEQ ID NO: 33.

Another aspect of the present invention relates to an exosome produced by the methods provided herein.

In yet another aspect, the present invention relates to a pharmaceutical composition comprising the exosome of the present invention and an excipient. In some embodiments, the pharmaceutical composition comprises a lower concentration of macromolecules than the sample comprising the exosome source, wherein the macromolecules are nucleic acids, contaminant proteins, lipids, carbohydrates, metabolites, or a combination thereof. In some embodiments, the pharmaceutical composition is substantially free of the macromolecules.

Another aspect of the present invention relates to an exosome comprising a target protein wherein at least a part of the target protein is expressed from an exogenous sequence, and the target protein comprises PTGFRN, BSG, IGSF2, IGSF3, IGSF8, ITGB1, ITGA4, SLC3A2, ATP transporter or a fragment or a variant thereof. In some embodiments, the target protein does not comprise IGSF8 or a fragment or a variant thereof. In some embodiments, the target protein comprises a polypeptide of SEQ ID NO: 33.

In some embodiments, the exosome is isolated based on a binding between the target protein and a binding agent.

In some embodiments, the exosome is produced from a cell genetically modified to comprise the exogenous sequence, optionally wherein the cell is an HEK293 cell, a Chinese hamster ovary (CHO) cell, or a mesenchymal stem cell (MSC). In some embodiments, the cell is genetically modified to have a reduced expression of ADAM10.

In some embodiments, the cell comprises a plasmid comprising the exogenous sequence.

In some embodiments, the cell comprises the exogenous sequence inserted into a genome of the cell. In some embodiments, the exogenous sequence is inserted into a genomic site located 3' or 5' end of a genomic sequence encoding PTGFRN, BSG, IGSF2, IGSF3, IGSF8, ITGB1, ITGA4, SLC3A2 or ATP transporter. In some embodiments, the exogenous sequence is inserted into a genomic sequence encoding PTGFRN, BSG, IGSF2, IGSF3, IGSF8, ITGB1, ITGA4, SLC3A2 or ATP transporter. In some embodiments, the exogenous sequence does not encode IGSF8.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and an affinity tag, wherein the affinity tag has affinity to the binding agent. In some embodiments, the target protein does not comprise IGSF8 or a fragment thereof.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and a therapeutic peptide. In some embodiments, the target protein does not comprise IGSF8 or a fragment thereof.

The therapeutic peptide can be selected from a group consisting of a natural peptide, a recombinant peptide, a synthetic peptide, or a linker to a therapeutic compound. The therapeutic compound can be selected from the group consisting of nucleotides, amino acids, lipids, carbohydrates, and small molecules.

The therapeutic peptide can be an antibody or a fragment or a variant thereof. The therapeutic peptide can be an enzyme, a ligand, a receptor, or a fragment or a variant thereof. The therapeutic peptide can be an antimicrobial peptide or a fragment or a variant thereof.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and a targeting moiety. The targeting moiety can be specific to an organ, a tissue, or a cell. In some embodiments, the target protein does not comprise IGSF8 or a fragment thereof.

In some embodiments, the exosome further comprises a second, different target protein, wherein the different target protein comprises PTGFRN, BSG, IGSF2, IGSF3, IGSF8, ITGB1, ITGA4, SLC3A2, ATP transporter, or a fragment or a variant thereof. In some embodiments, the exosome is isolated based on a binding between the different target protein and a different binding agent. In some embodiments, the target protein does not comprise IGSF8 or a fragment thereof.

In one aspect, the present invention relates to a pharmaceutical composition comprising the exosome of the present invention and an excipient.

In some embodiments, the pharmaceutical compositions are substantially free of macromolecules, wherein the macromolecules are selected from nucleic acids, contaminant proteins, lipids, carbohydrates, metabolites, and a combination thereof.

In one aspect, the present invention is directed to a cell for producing the exosome presented herein.

Specifically, some embodiments relate to a cell for producing exosomes, comprising an exogenous sequence inserted into a genomic sequence encoding PTGFRN, BSG, IGSF2, IGSF3, IGSF8, ITGB1, ITGA4, SLC3A2, or ATP transporter, wherein the exogenous sequence and the genomic sequence encodes a fusion protein. In some embodiments, the genomic sequence does not encode IGSF8.

The exogenous sequence can encode an affinity tag.

The exogenous sequence can encode a therapeutic peptide. The therapeutic peptide can be selected from a group consisting of a natural peptide, a recombinant peptide, a synthetic peptide, or a linker to a therapeutic compound. The therapeutic compound can be selected from the group consisting of nucleotides, amino acids, lipids, carbohydrates, and small molecules. The therapeutic peptide can be an antibody or a fragment or a variant thereof. The therapeutic peptide can be an enzyme, a ligand, a receptor, or a fragment or a variant thereof. The therapeutic peptide can be an antimicrobial peptide or a fragment or a variant thereof.

The exogenous sequence can encode a targeting moiety. The targeting moiety can be specific to an organ, a tissue, or a cell.

In some embodiments, the cell line is genetically modified to have a reduced expression of ADAM10.

In one aspect, the present invention provides an exosome produced from the cell line of the present invention. In some embodiments, the exosome includes the fusion protein on the surface at a higher density than a different fusion protein on the surface of a different exosome, wherein the different exosome is produced from a different cell line comprising the exogenous sequence inserted into a different genomic sequence encoding a conventional exosome protein, wherein the exogenous sequence and the different genomic sequence encodes the different fusion protein. In some embodiments, the conventional exosome protein is selected from the group consisting of CD9, CD63, CD81, PDGFR, GPI anchor proteins, LAMP2, LAMP2B, and a fragment thereof.

In another aspect, the present invention relates to a method of isolating a non-exosomal material, comprising the steps of: providing a sample comprising an exosome and the non-exosome material; contacting the sample with a binding agent having affinity to a target protein, wherein the target protein comprises PTGFRN, BSG, IGSF2, IGSF3, IGSF8, ITGB1, ITGA4, SLC3A2, ATP transporter or a fragment or a variant thereof, thereby inducing the exosome to bind to the binding agent; and isolating the non-exosome material.

In some embodiments, the non-exosomal material is virus or a protein. In some embodiments, the non-exosomal material is lentivirus, retrovirus, adeno-associated virus, or other enveloped or non-enveloped virus. In some embodiments, the non-exosomal material is a recombinant protein. In some embodiments, the isolated non-exosomal material is substantially free of exosomes.

In some embodiments, the target protein further comprises an affinity tag, wherein the affinity tag has affinity to the binding agent. In some embodiments, the target protein comprises a polypeptide of SEQ ID NO: 33. In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane. In some embodiments, the solid support forms a chromatography column. In some embodiments, the step of contacting the sample with the binding agent is performed by applying the sample to the chromatography column.

In some embodiments, the methods of purification described herein are used for purification of nanovesicles. In some embodiments, the compositions and methods described herein are directed to nanovesicles.

5. BRIEF DESCRIPTION OF THE DRAWINGS

The figures depict various embodiments of the present invention for purposes of illustration only. One skilled in the art will readily recognize from the following discussion that alternative embodiments of the structures and methods illustrated herein may be employed without departing from the principles of the invention described herein.

FIG. 1 provides an image of sample-containing Optiprep™ density gradient after ultracentrifugation. Marked with brackets are the top fraction containing exosomes ("Top"), the middle fraction containing cell debris ("Middle") and the bottom fraction containing high density aggregates and cellular debris ("Bottom").

Figure 2:
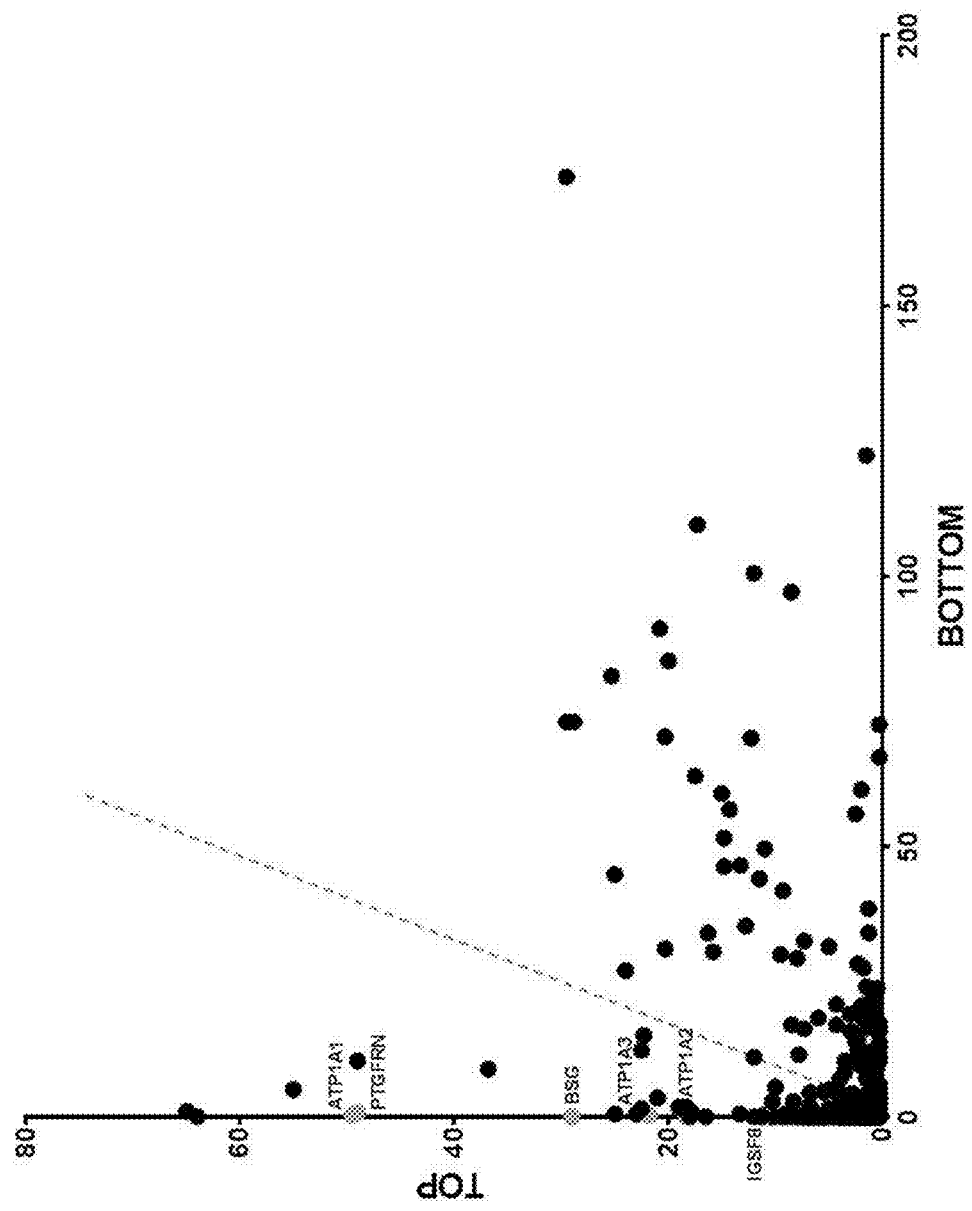

FIG. 2 is a dot-graph showing proteins identified from the top fraction (Y-axis) and proteins identified from the bottom fraction (X-axis) of Optiprep™ ultracentrifugation. Proteins plotted above the dotted line represent exosome-enriched proteins, while those below the dotted line represent proteins not specific to exosomes.

FIG. 3 provides a tryptic peptide coverage map of PTGFRN.

FIG. 4 provides a tryptic peptide coverage map of IGSF8.

FIG. 5 provides a tryptic peptide coverage map of Basigin (BSG).

Figures 6A, 6B:
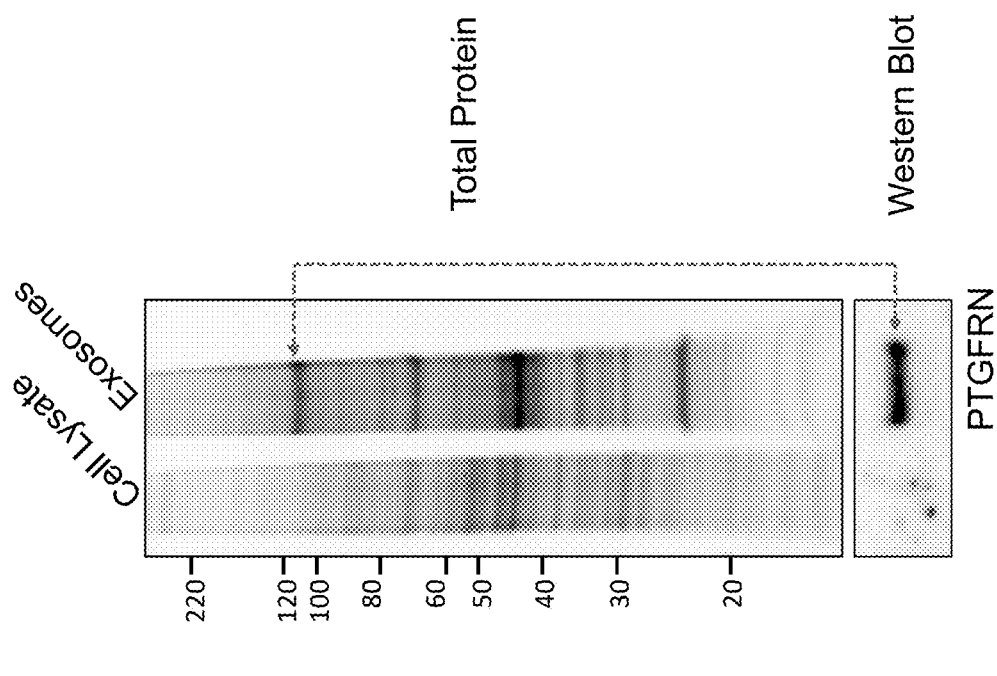

FIG. 6A shows a picture from protein blotting of total cell lysate (left) and purified exosome populations (right) collected from HEK293 cells. FIG. 6B shows a result of western blotting of the gel provided in FIG. 6A with an antibody against PTGFRN. The band detected on the right column corresponds to a band at ~110 kDa in FIG. 6A.

Figures 7A, 7B:
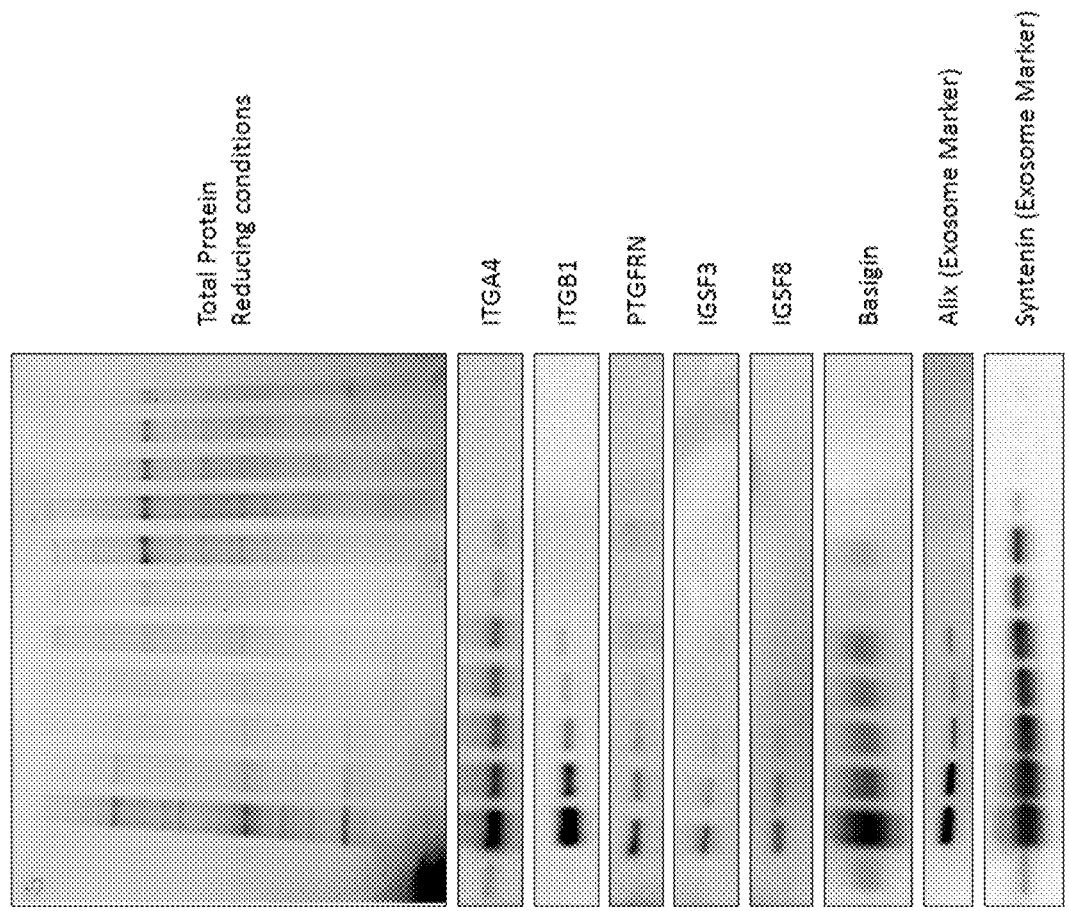

FIG. 7A shows protein blotting of twelve fractions collected from a purification using self-forming Optiprep™ gradients. FIG. 7B shows a result of western blotting of the gel presented in FIG. 7A with antibodies against ITGA4, ITGB1, PTGFRN, IGSF3, IGSF8, Basigin, Alix, or Syntenin. Each of the novel exosome surface proteins (ITGA4, ITGB1, PTGFRN, IGSF8, Basigin) is detected in the same fractions as the well-known exosome marker proteins (Alix, Syntenin).

Figure 8:
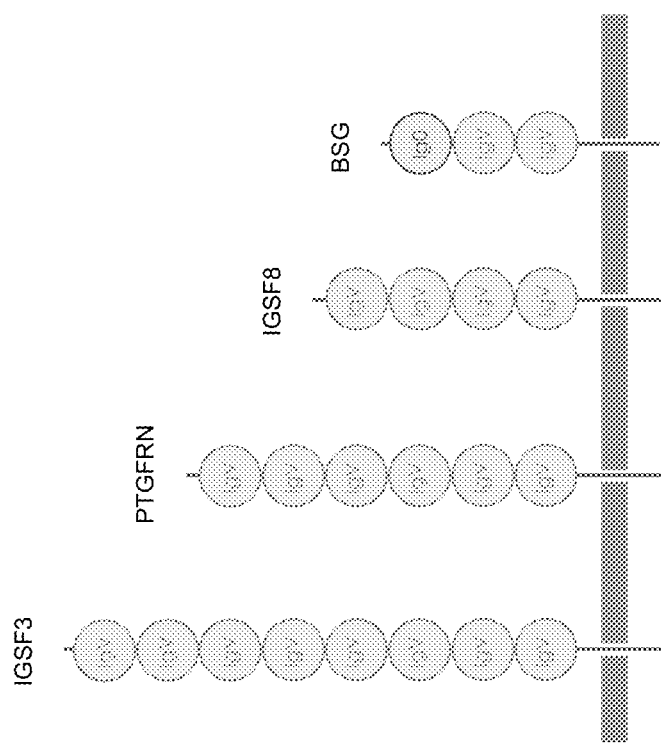

FIG. 8 illustrates exosome surface proteins (ITGA4, ITGB1, PTGFRN, IGSF8, BSG) that are used for various embodiments of the present invention, for example, for targeting a fusion protein on the surface of an exosome, or as a target for affinity purification of an exosome.

Figure 9B:
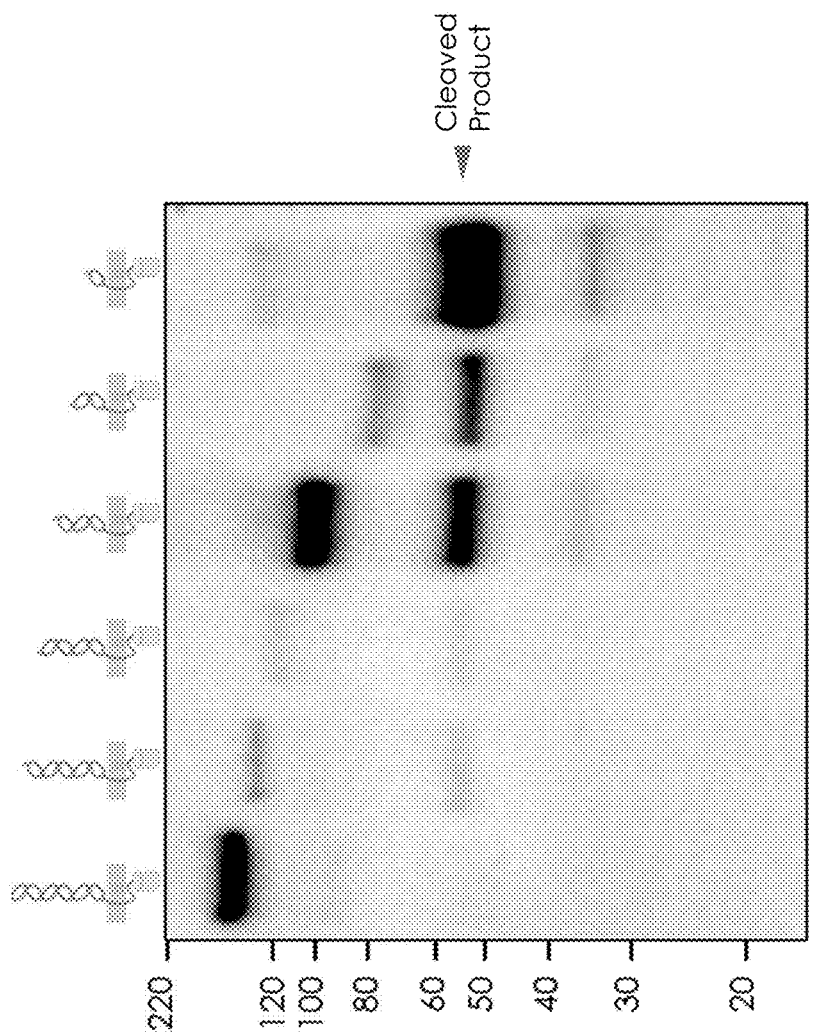
Figure 9A:
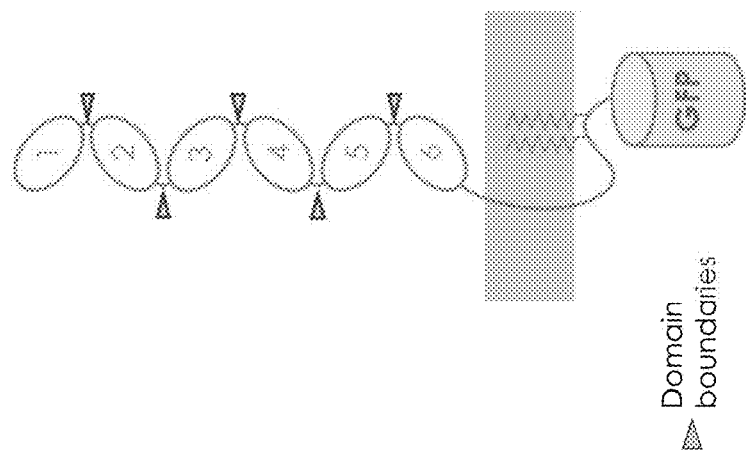

FIG. 9A illustrates the structure of PTGFRN with identification of boundaries of IgV domains (arrows) and GFP fused to the C terminus of PTGFRN. FIG. 9B provides a gel picture from western blotting exosomes isolated from a cell culture overexpressing various GFP-PTGFRN fusion proteins. GFP-PTGFRN fusion proteins were detected using an antibody against GFP.

Figure 10:
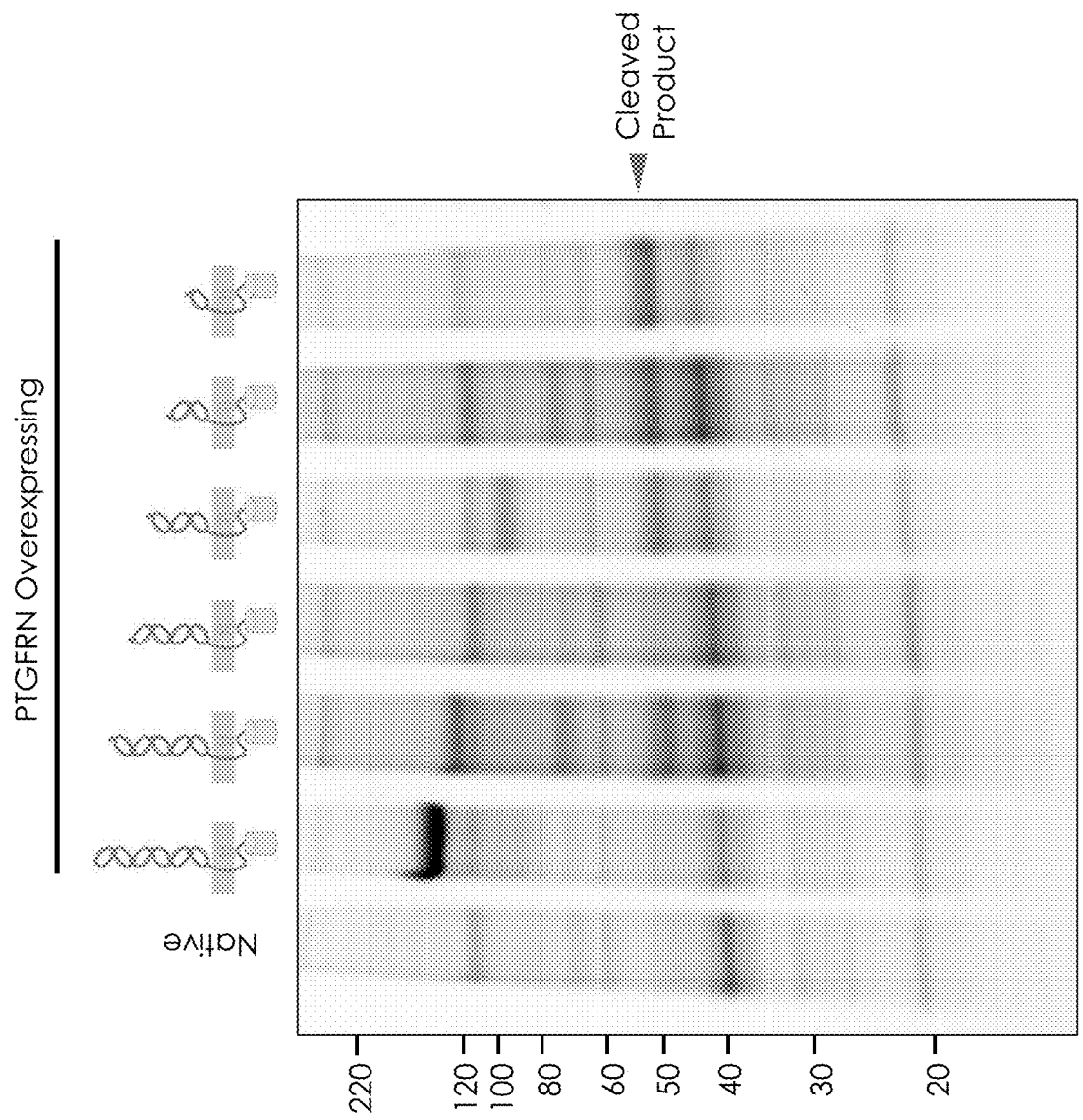

FIG. 10 provides a gel picture running total proteins of the purified exosomes isolated from cells overexpressing various GFP-PTGFRN fusion proteins.

Figure 11B:
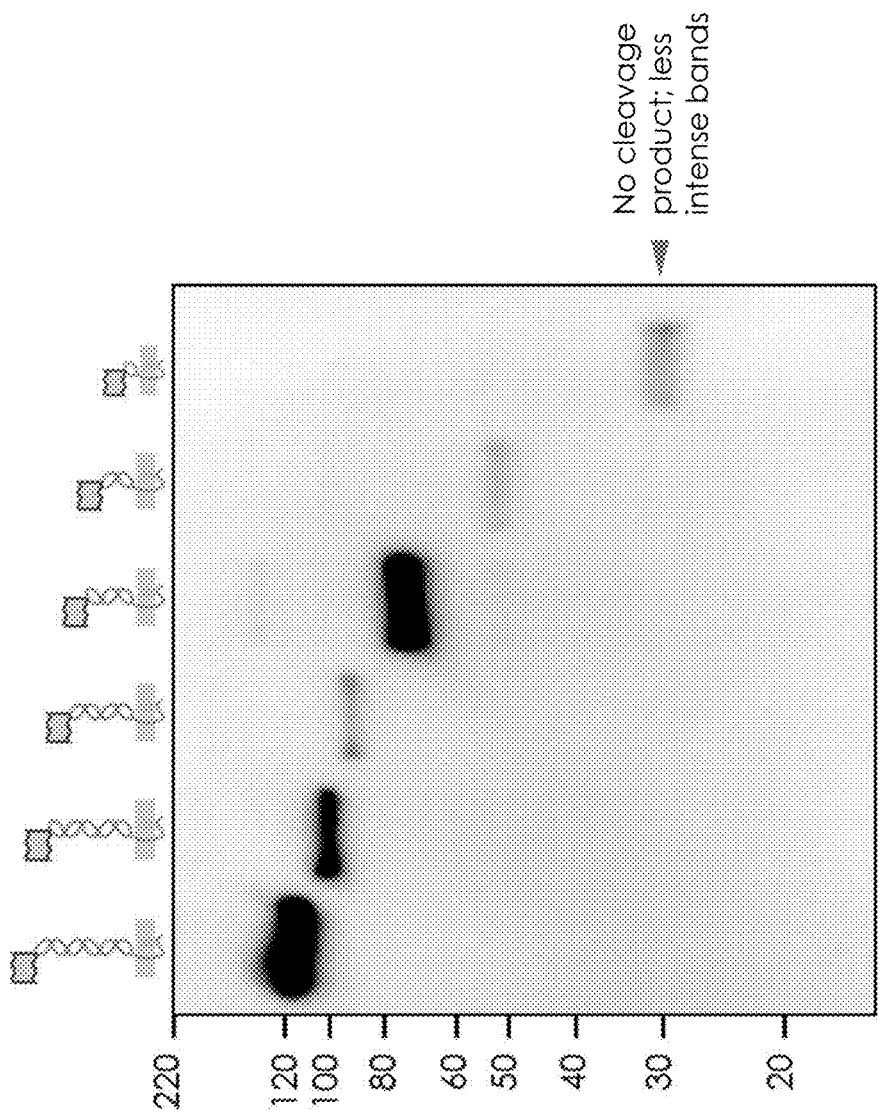
Figure 11A:
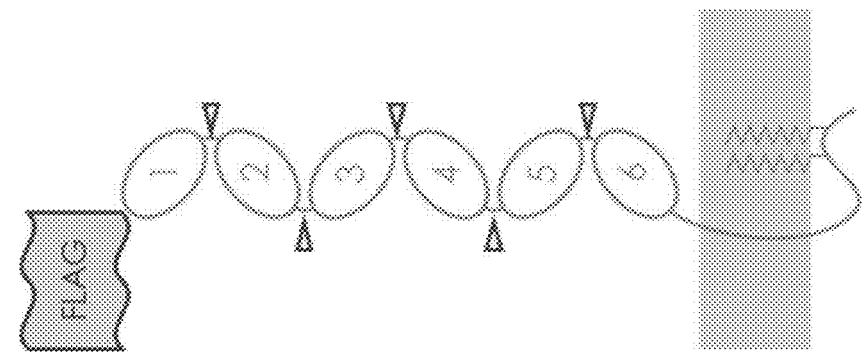

FIG. 11A illustrates the structure of PTGFRN with identification of boundaries of IgV domains (arrows) and FLAG fused to the N terminus of PTGFRN. FIG. 11B provides a gel picture from western blotting exosomes isolated from a cell culture overexpressing various FLAG-PTGFRN fusion proteins. GFP-PTGFRN fusion proteins were detected using an antibody against FLAG tag.

Figure 12C:
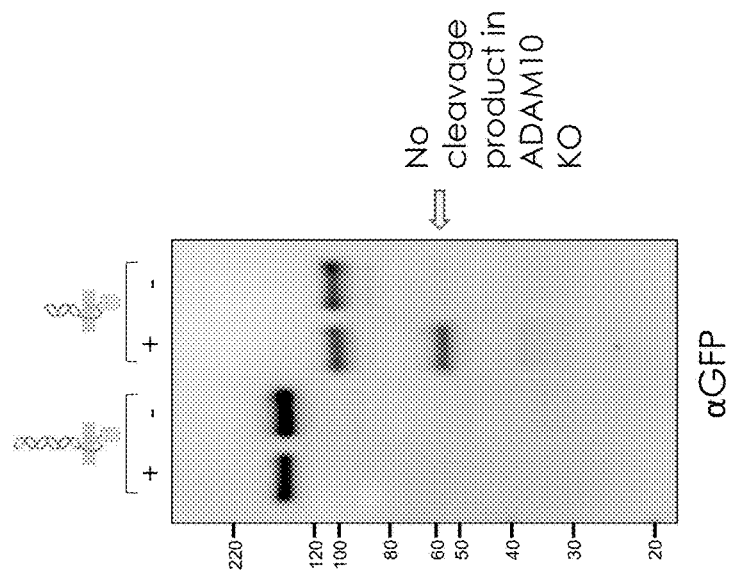
Figure 12B:
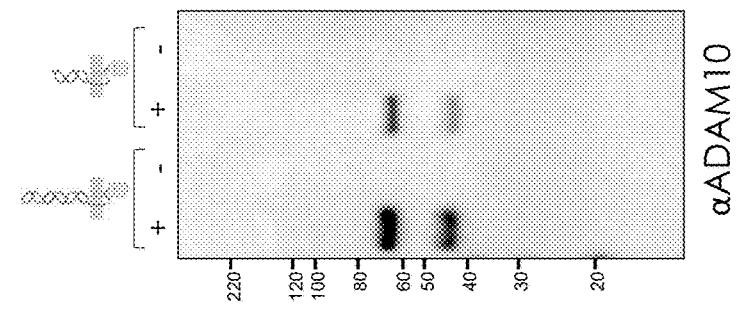
Figure 12A:
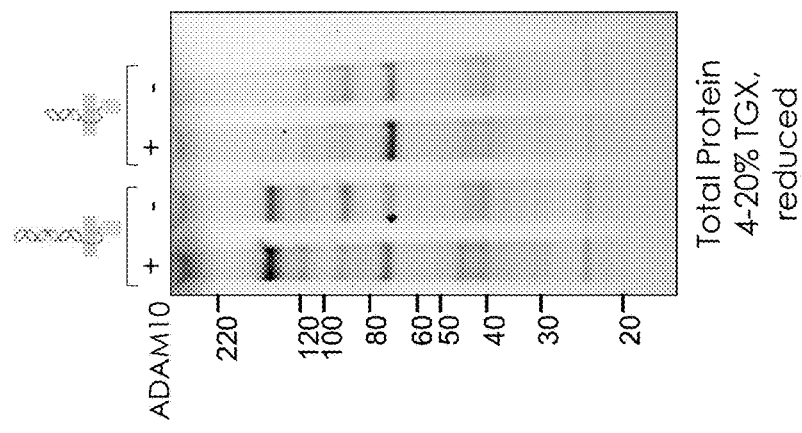

FIG. 12A provides a gel picture running total proteins of the purified exosomes isolated from wild type cells (ADAM10+) or ADAM10 knockout cells (ADAM10−), each cells expressing a GFP fusion protein containing full-length PTGFRN (PTGFRN-GFP) or a truncated PTGFRN (PTGFRN_IgV3-GFP). FIG. 12B provides a gel picture from western blotting the samples of FIG. 12A using an antibody against ADAM10. FIG. 12C provides a gel picture from western blotting the samples of FIG. 12A using an antibody against GFP.

Figure 13:
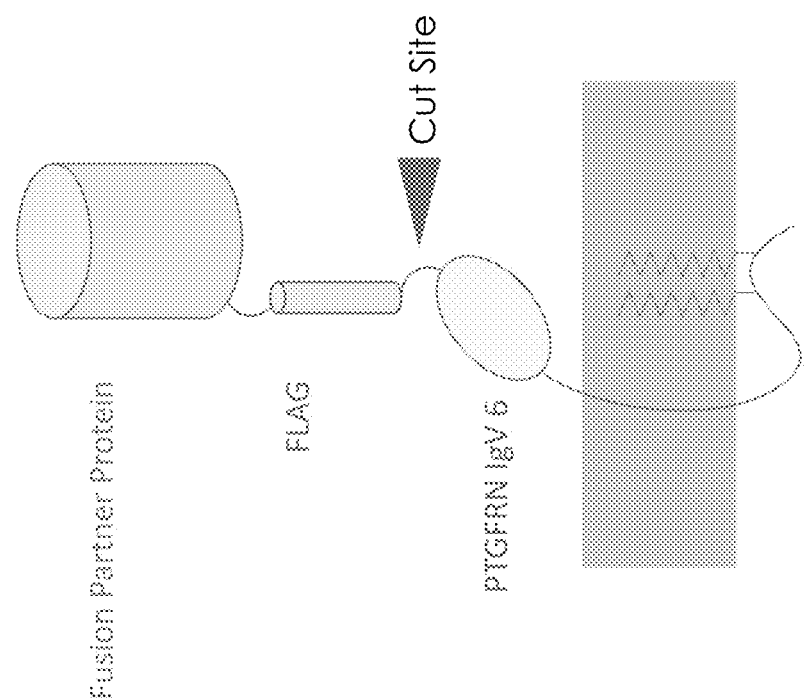

FIG. 13 illustrates the structure of a fusion protein containing PTGFRN lacking five of the six IgV domains (PTGFRN_IgV6), FLAG tag, and a fusion partner protein.

FIG. 14A provides sequences of PTGFRN_IgV6 (#451) and serial truncation mutants of PTGFRN_IgV6 lacking four (#452), eight (#453), or twelve (#454) additional amino acids. FIG. 14B provides a gel picture running total proteins of the purified exosomes isolated from cells overexpressing a fusion protein #451, 452, 453 or 454. FIG. 14C provides a gel picture from western blotting the sample of FIG. 14B using an antibody against FLAG.

Figure 15:
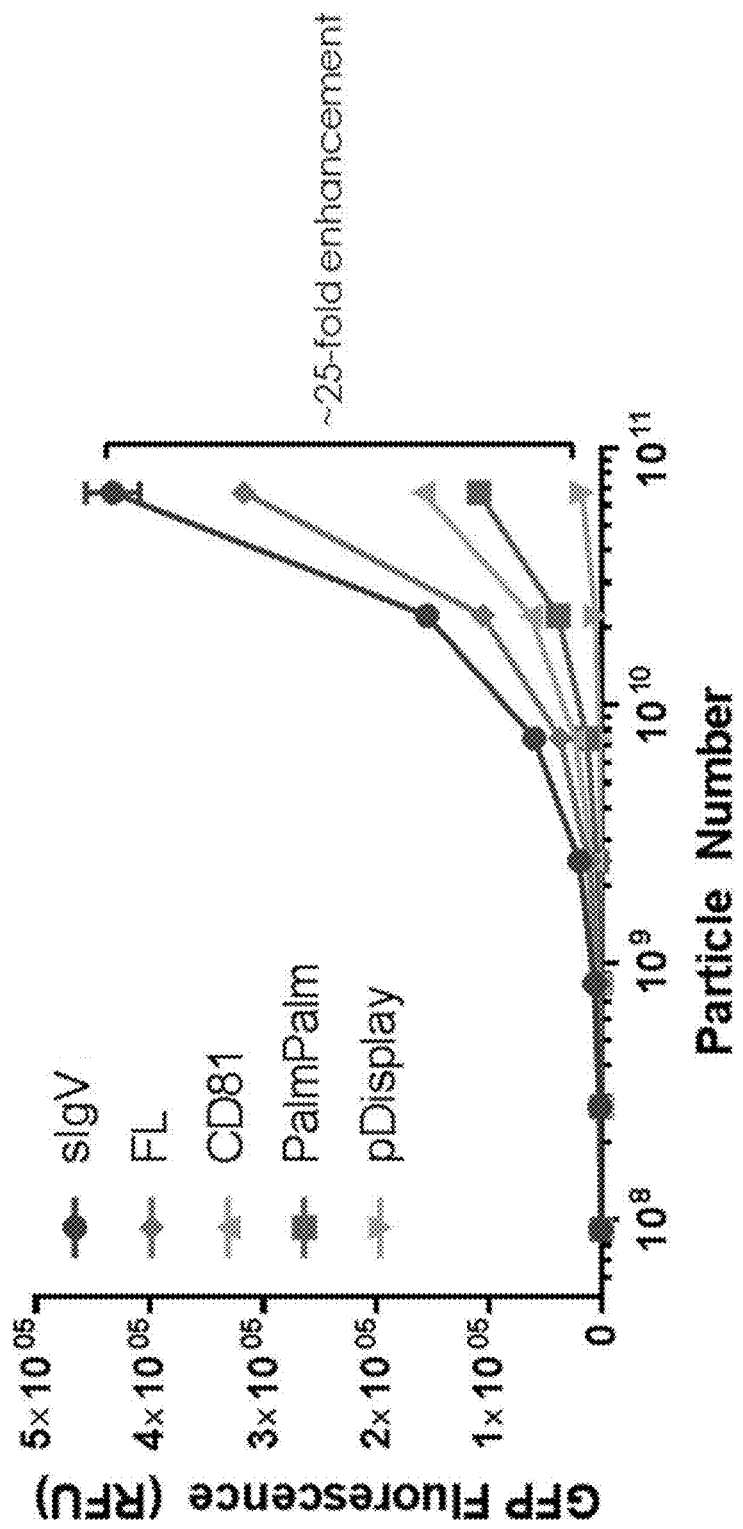

FIG. 15 provides GFP fluorescence signals detected from exosomes isolated from cells overexpressing various GFP fusion proteins—the GFP fusion proteins contain GFP fused to the luminal side of the frequently used pDisplay scaffold (PDGF receptor), PalmPalm (palmitoylation sequence), CD81, or either full length PTGFRN (FL) or PTGFRN_454 (sIgV).

Figure 16B:
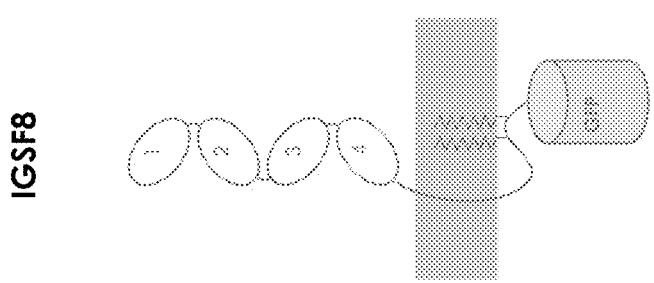
Figure 16A:
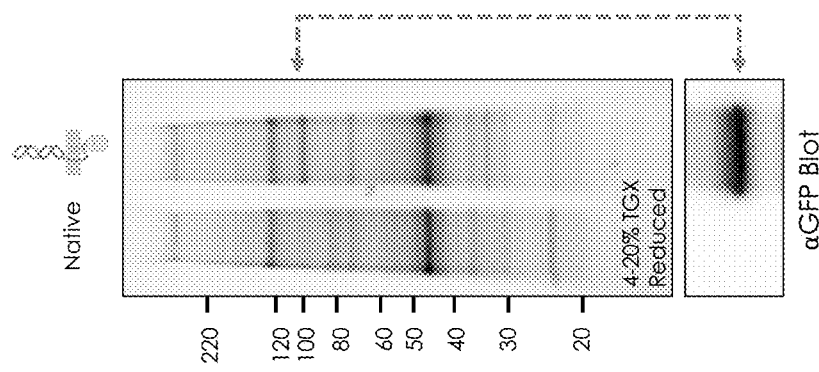

FIG. 16A illustrates the structure of a fusion protein containing IGSF8 and GFP fused to the C terminus of IGSF8. FIG. 16B provides a gel picture running total proteins from exosomes isolated from untransfected HEK293 cells (native) or HEK cells stably transfected with a construct encoding an IGFS8-GFP fusion protein.

FIG. 16B also provides on the bottom a gel picture from western blotting the sample with an antibody against GFP.

Figure 17:
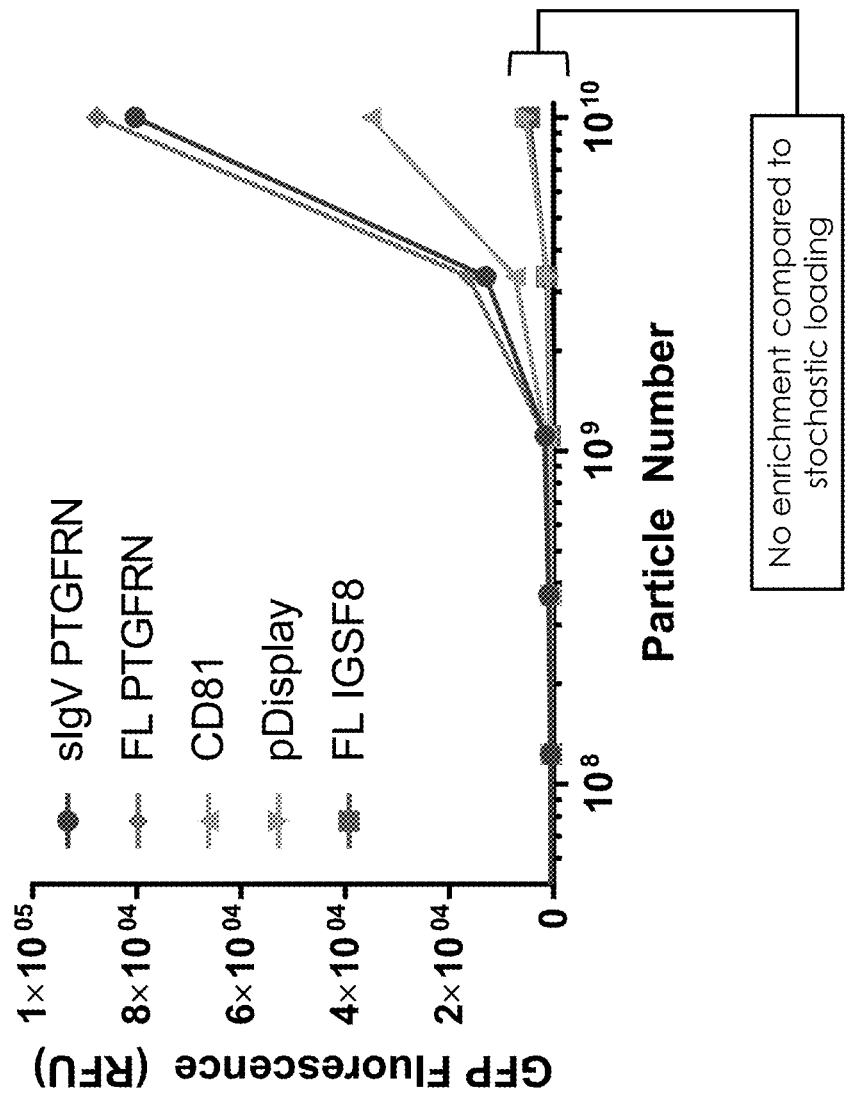

FIG. 17 provides GFP fluorescence signals detected from exosomes isolated from cells overexpressing various GFP fusion proteins—the GFP fusion proteins contain GFP fused to the luminal side of the frequently used pDisplay scaffold (PDGF receptor), CD81, full length IGSF8, or either full length PTGFRN (FL) or PTGFRN_454 (sIgV).

Figure 18:
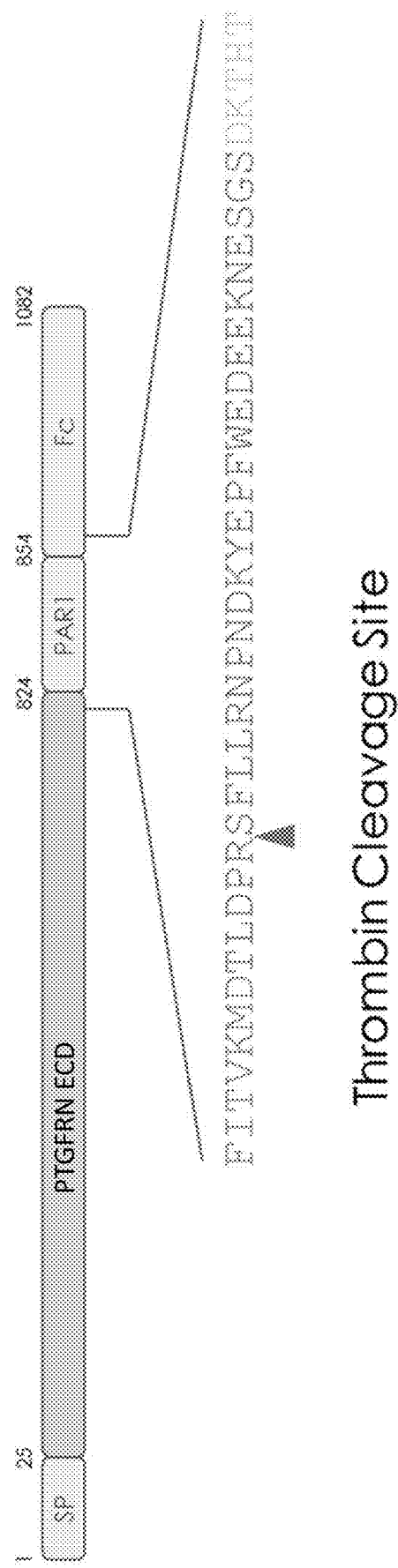

FIG. 18 provides a structure of a fusion protein containing the extracellular domain (ECD) of PTGFRN, the endogenous signal peptide at the N terminus (SP), a PAR1 cleavage site, and Fc domain at the C-terminus.

Figures 19A, 19B:
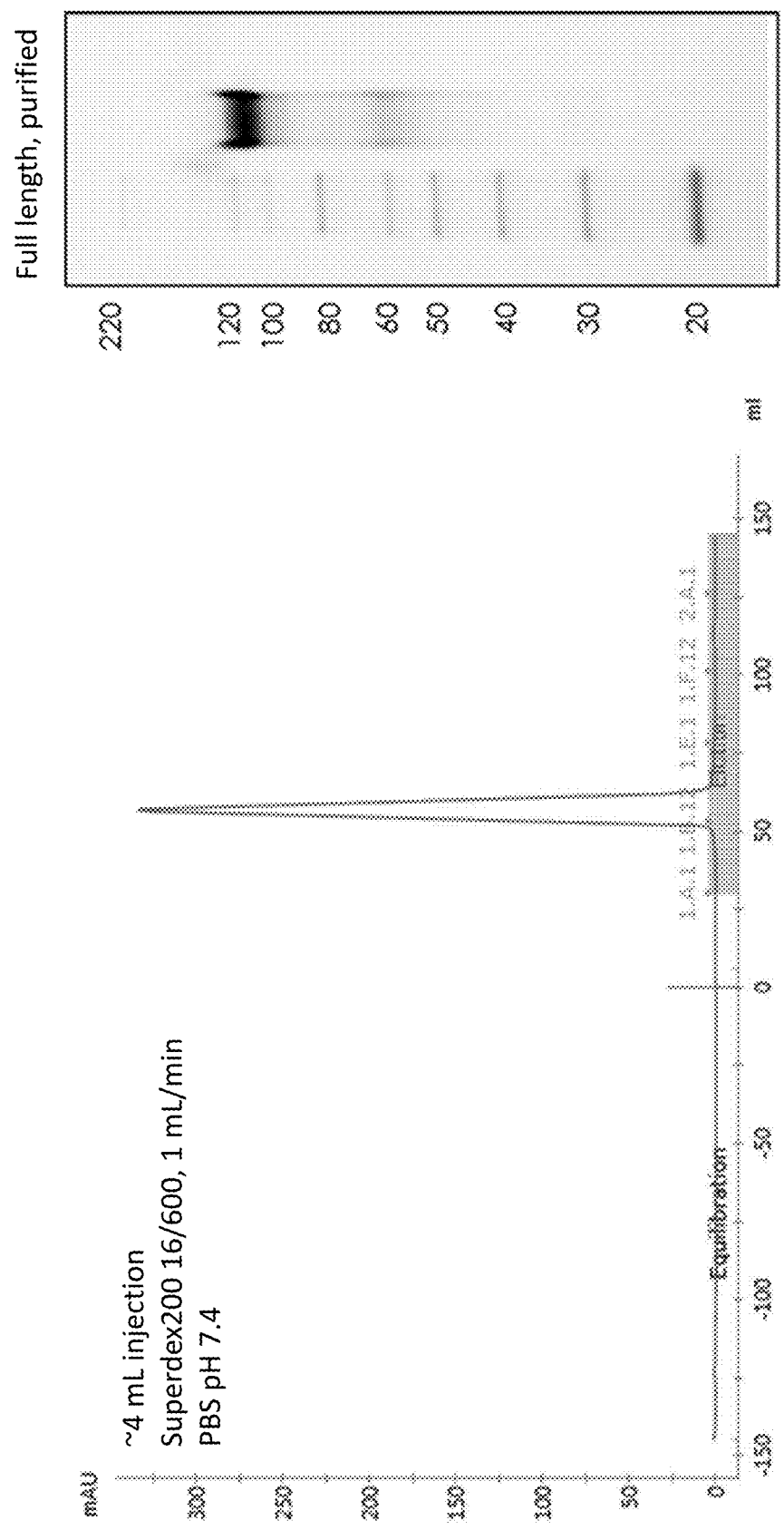

FIG. 19A provides a gel filtration chromatography result of purified ECD of PTGFRN in PBS pH 7.4 using a Superdex 200 column (Millpore Sigma) at 280 nm UV fluorescence. FIG. 19B provides an SDS-PAGE gel picture from gel filtration chromatography of eluate containing purified ECD of PTGFRN.

Figure 20A:
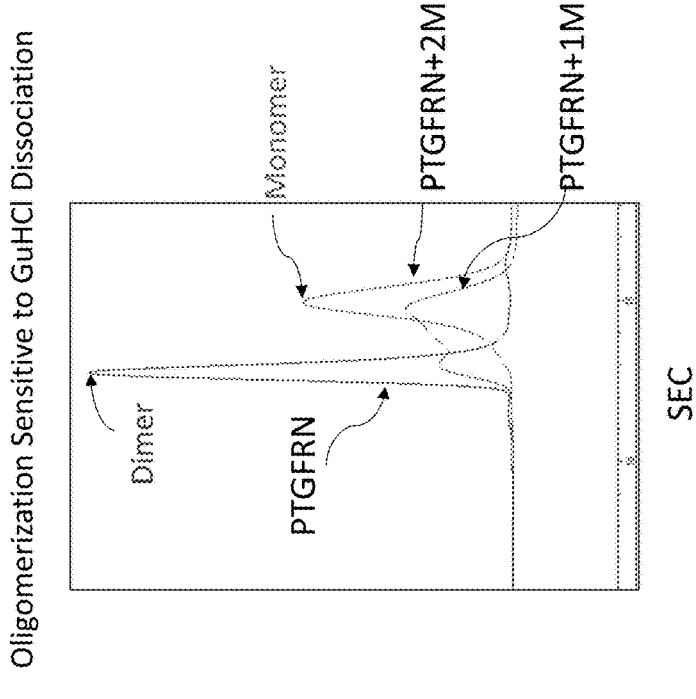
Figure 20B:
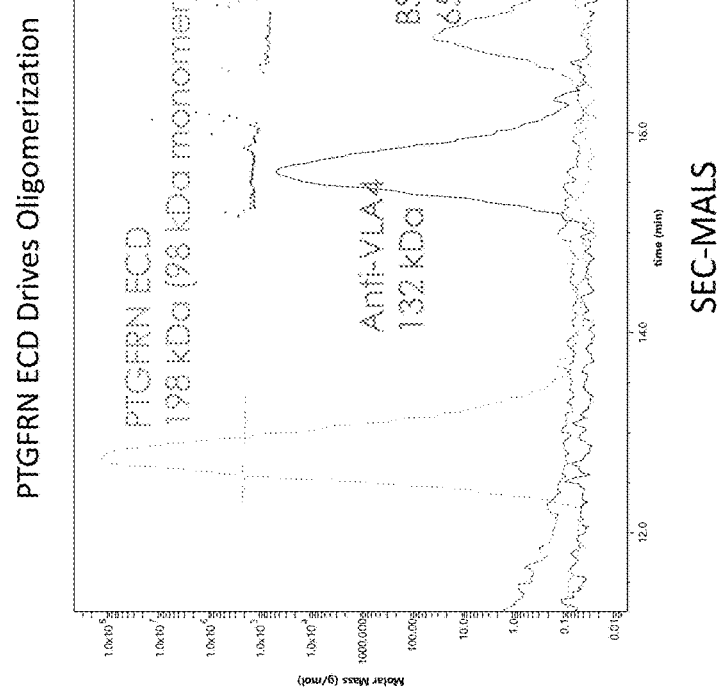

FIG. 20A provides size exclusion chromatography/multiangle light scattering (SEC-MALS) results of PTGFRN ECD, anti-VLA4 antibody, and BSA. FIG. 20B provides size exclusion chromatography (SEC) results of PTGFRN ECD in the absence of guanidium chloride (GuHCl), or in the presence of 1M, or 2M guanidinium chloride (GuHCl). Peaks representing a monomer or a dimer of PTGFRN are indicated.

FIG. 21 provides top three hits identified as PTGFRN ectodomain binding partners from a binding assay at pH 7.4 (top), and top five hits identified from the binding assay at pH 5.6 (bottom).

Figure 22:
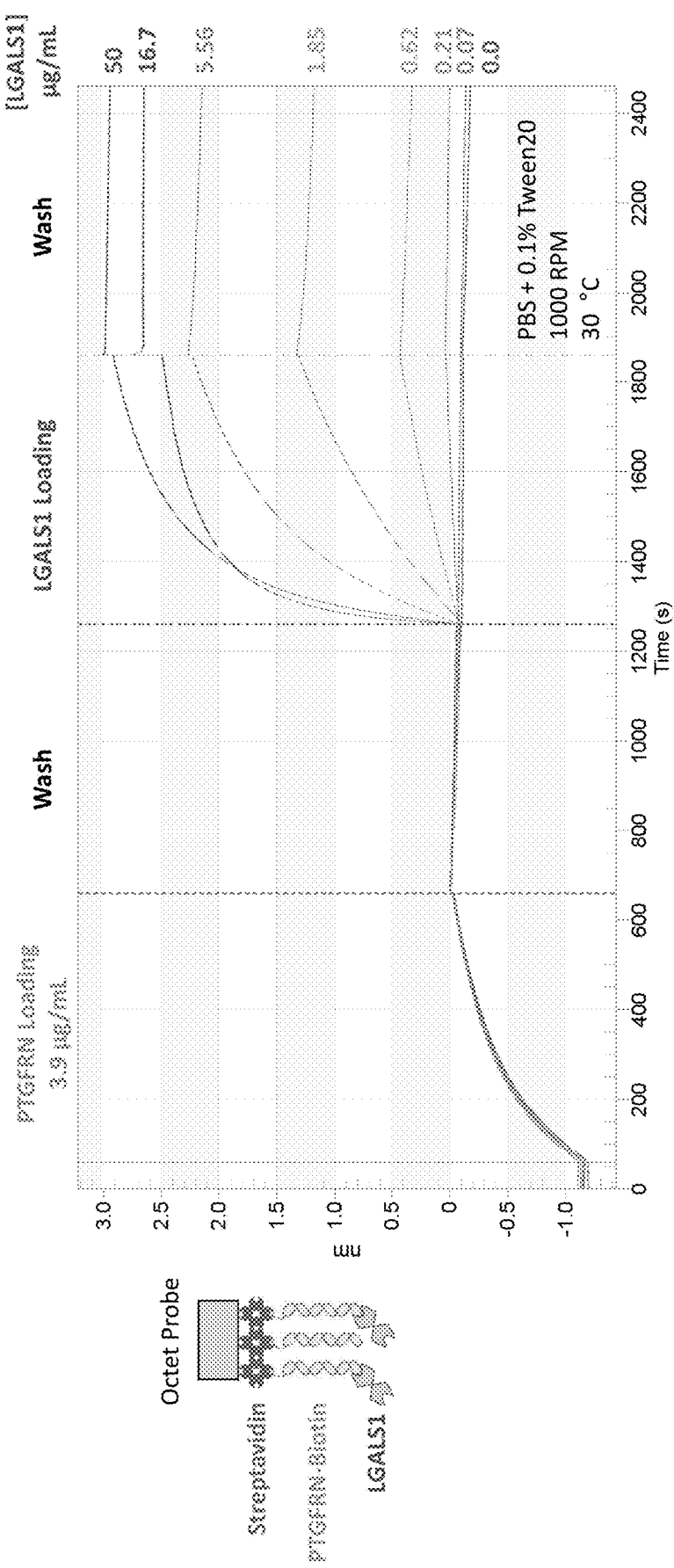

FIG. 22 provides bio-layer interferometry (BLI) results for studying the interaction between PTGFRN and LGALS1 in the presence of increasing concentrations of LGALS1.

Figure 23:
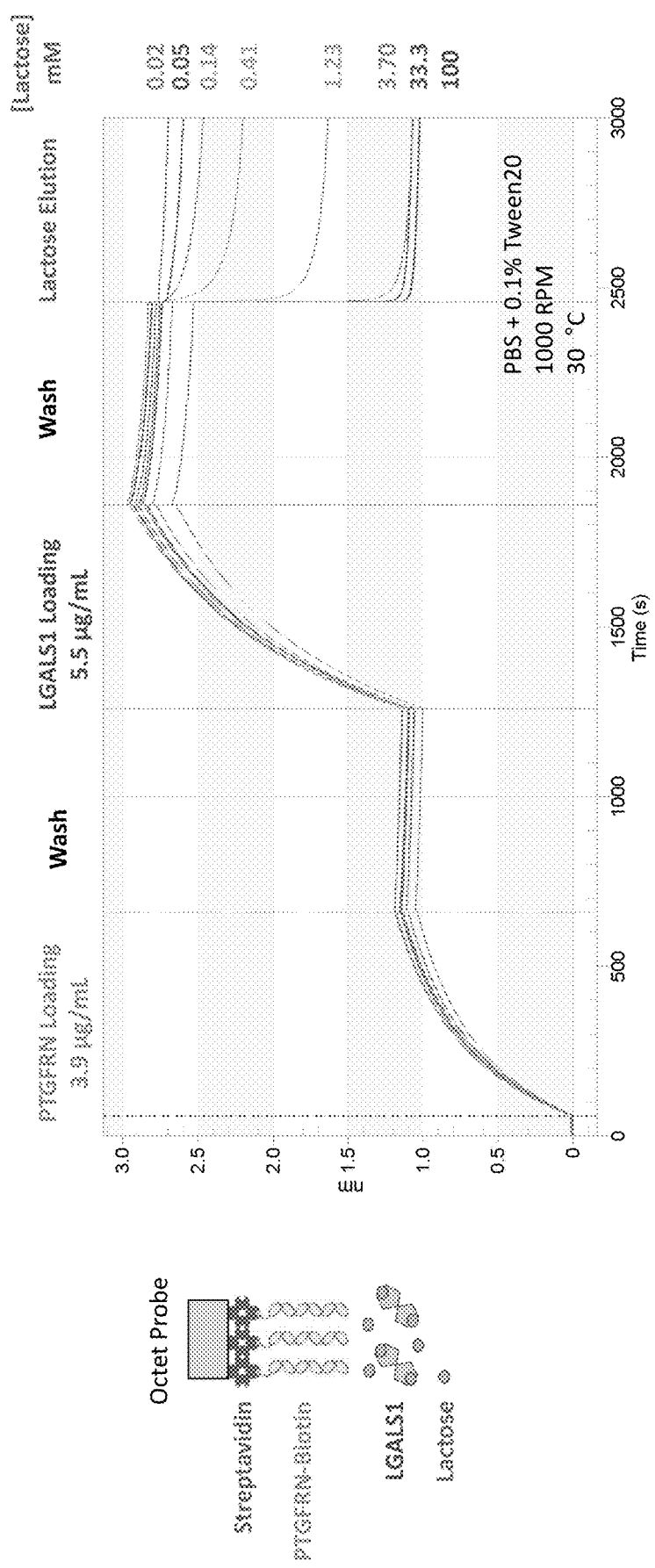

FIG. 23 provides bio-layer interferometry (BLI) results for studying the interaction between PTGFRN and LGALS1 in the presence of increasing concentrations of Lactose.

Figure 24:
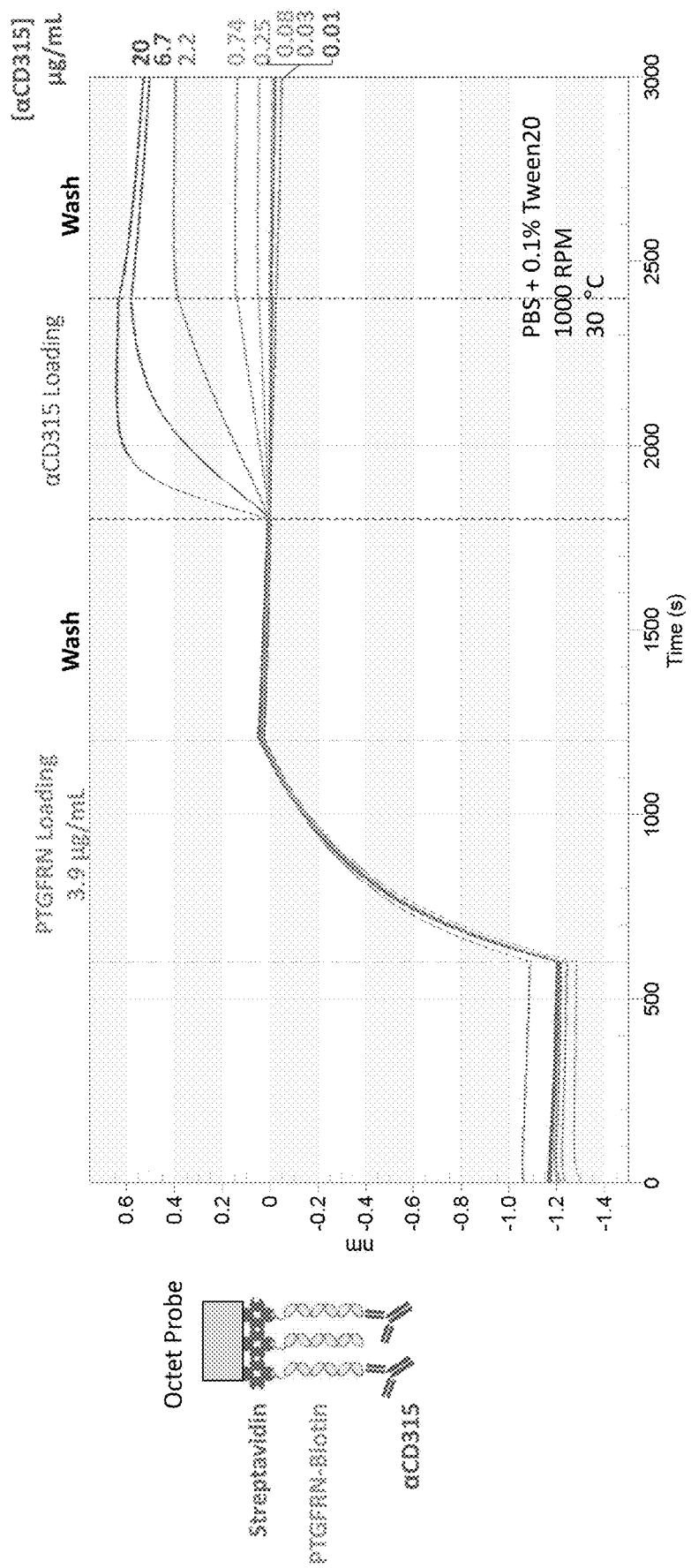

FIG. 24 provides bio-layer interferometry (BLI) results for studying the interaction between PTGFRN and anti-CD315 antibody in the presence of increasing concentrations of anti-CD315 antibody.

Figure 25:
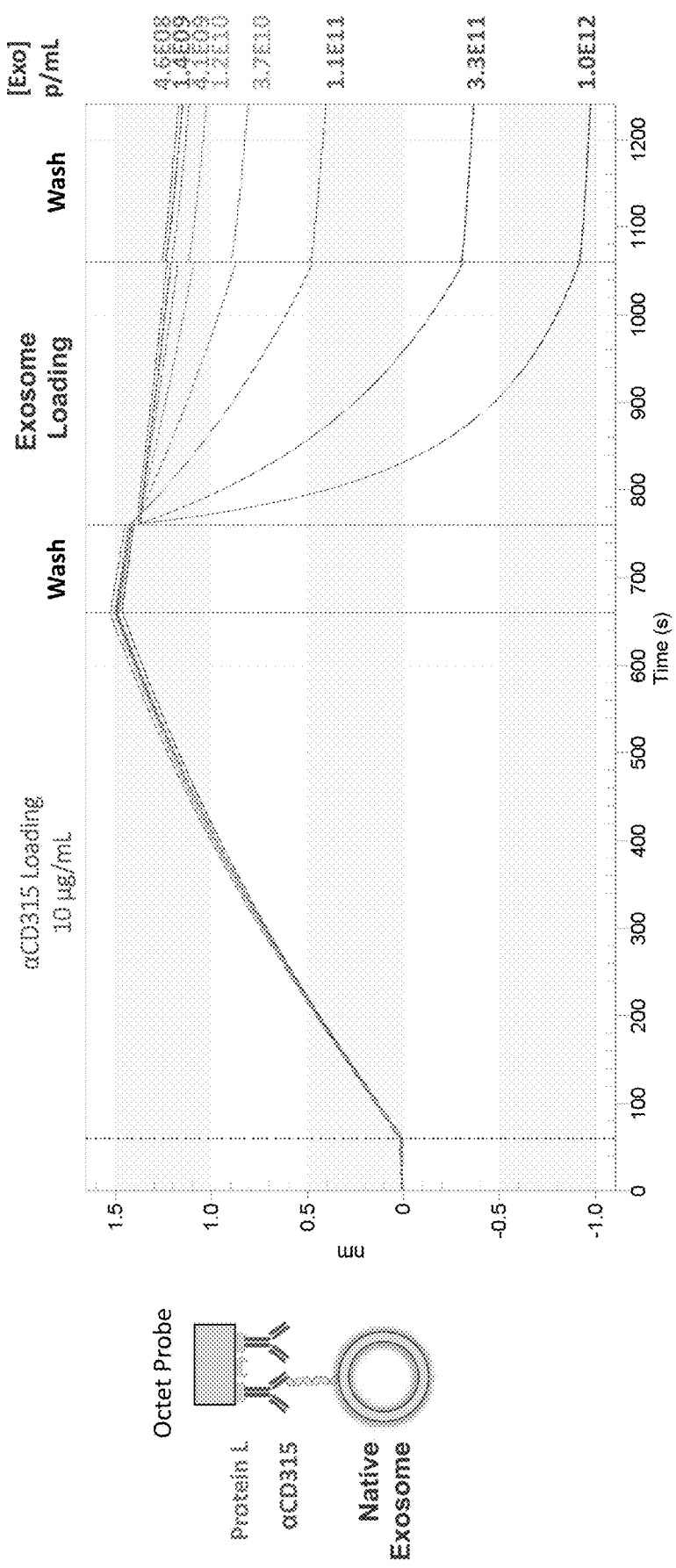

FIG. 25 provides bio-layer interferometry (BLI) results for studying the interaction between anti-CD315 antibody and native exosomes in the presence of increasing concentrations of native exosomes isolated from HEK293.

Figure 26:
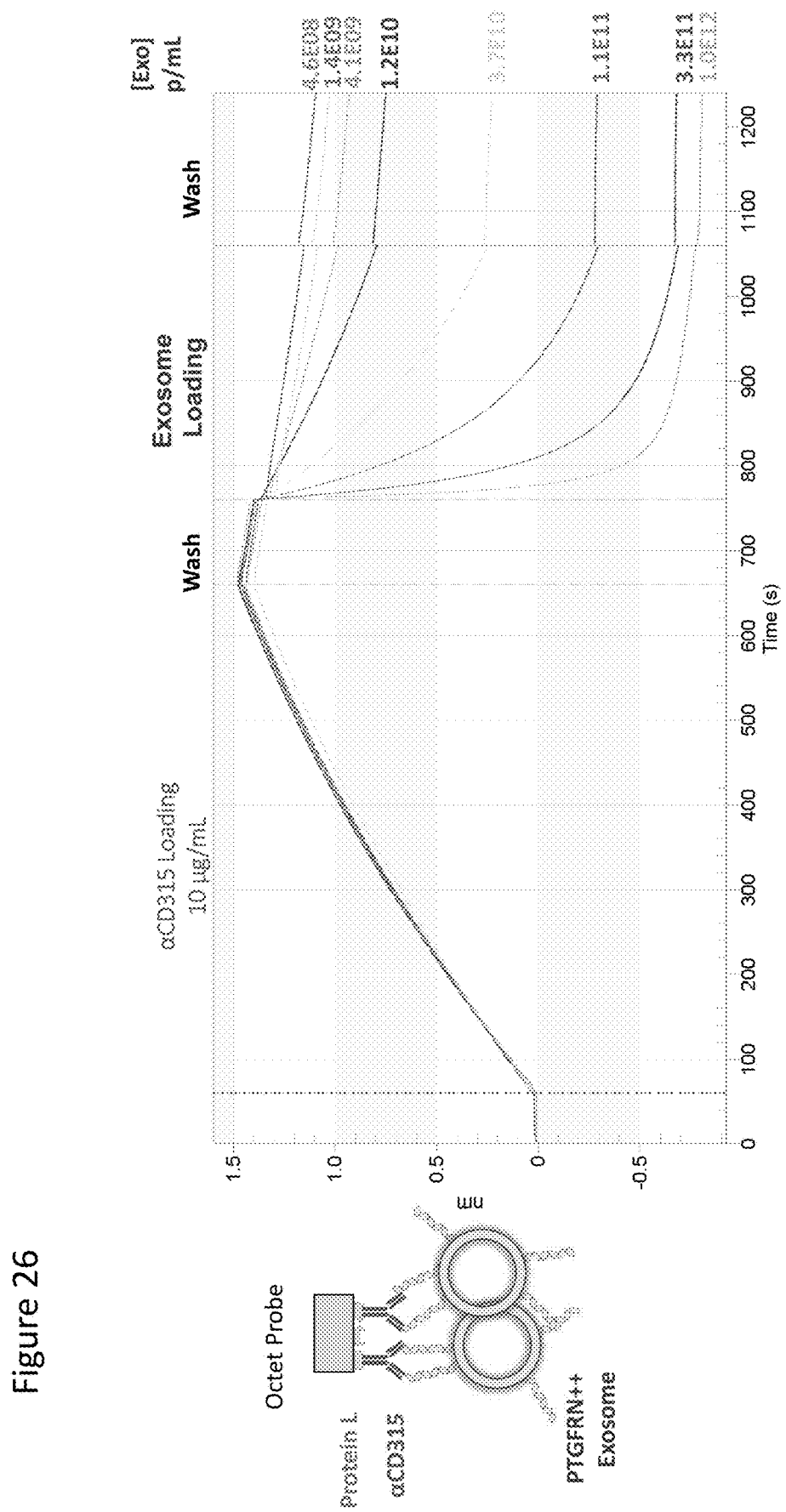

FIG. 26 provides bio-layer interferometry (BLI) results for studying the interaction between anti-CD315 antibody and exosomes modified to overexpress PTGFRN (PTGFRN++ exosomes) in the presence of increasing concentrations of the modified exosomes.

Figure 27:
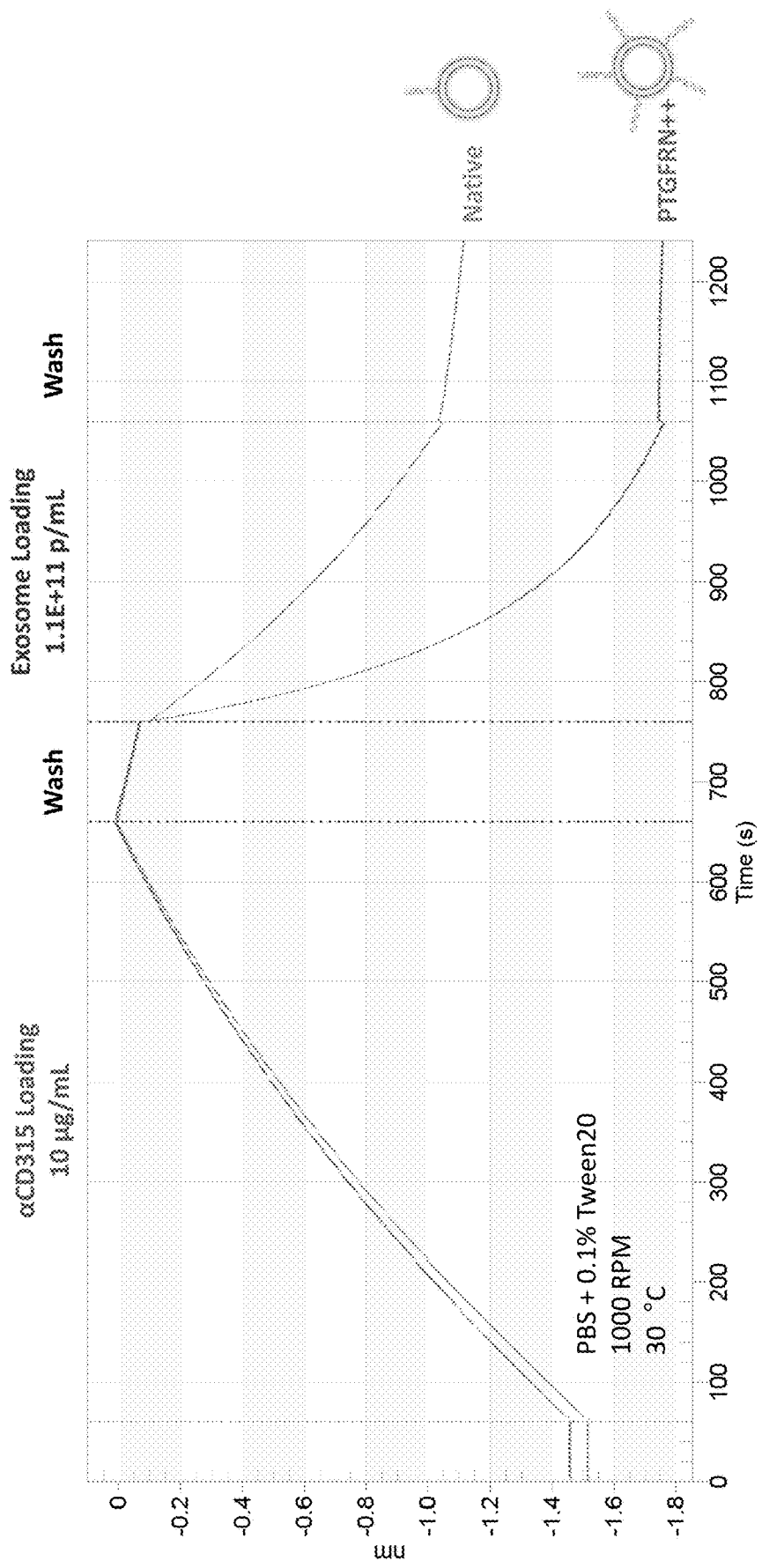

FIG. 27 provides bio-layer interferometry (BLI) results for comparing the interaction between anti-CD315 antibody and native exosomes, or between anti-CD315 antibody and modified exosomes overexpressing PTGFRN (PTGFRN++).

Figure 28:
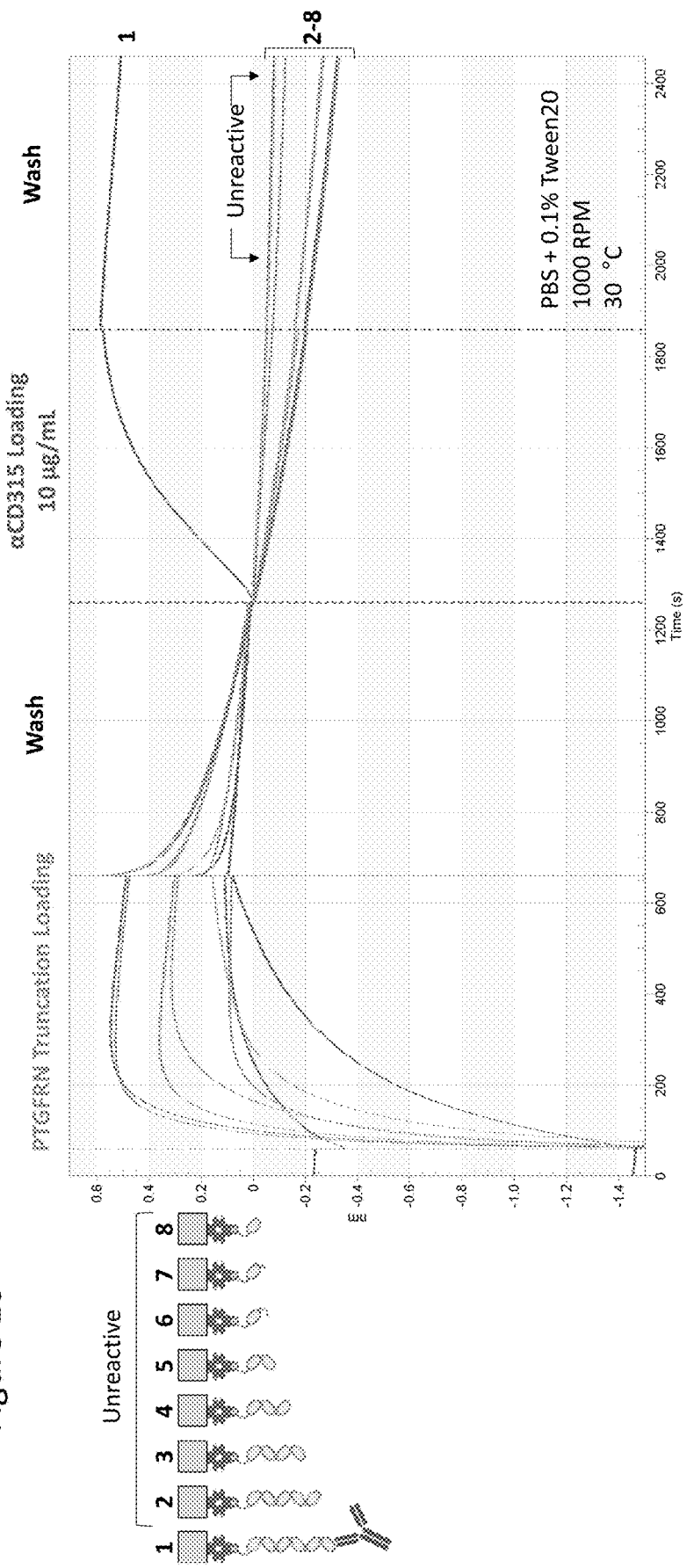

FIG. 28 provides bio-layer interferometry (BLI) results for studying the interaction between anti-CD315 antibody and full-length PTGFRN or between anti-CD315 antibody and a series of truncated mutants of PTGFRN.

Figure 29B:
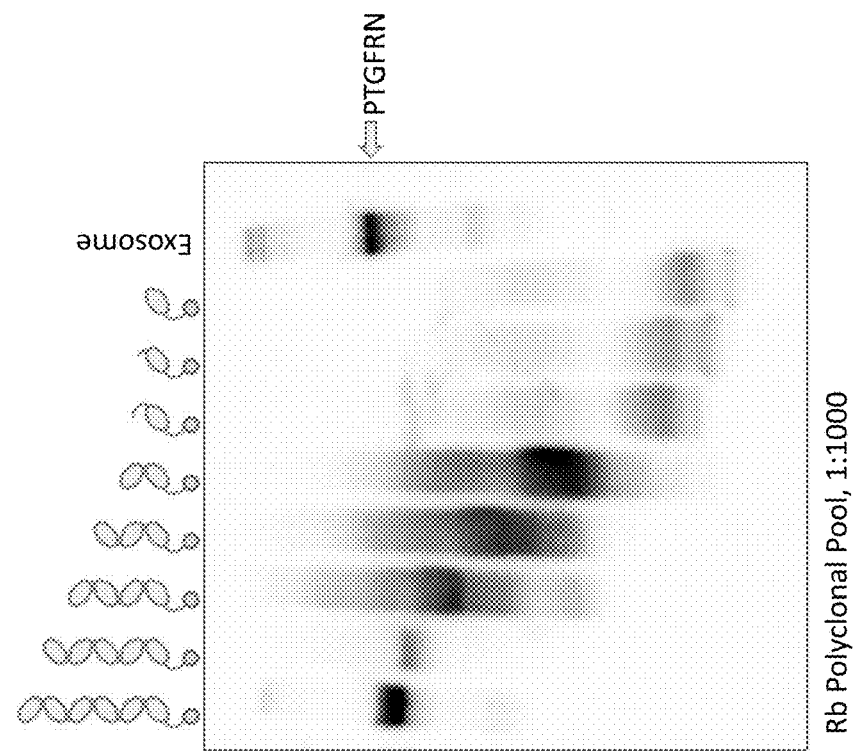
Figure 29A:
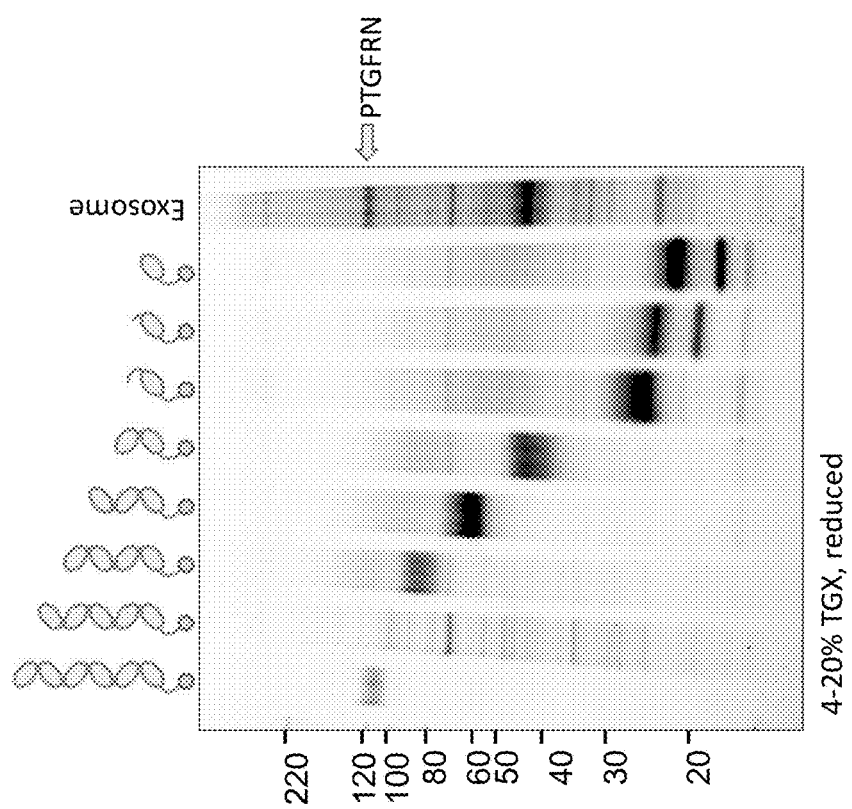

FIG. 29A provides a gel picture running in vivo biotinylated proteins including truncated mutants of recombinant PTGFRN isolated from transfected HEK cells, and purified exosomes from HEK293 cells. FIG. 29B provides a gel picture from western blotting the sample of FIG. 29A using pooled polyclonal PTGFRN antibodies.

Figure 30:
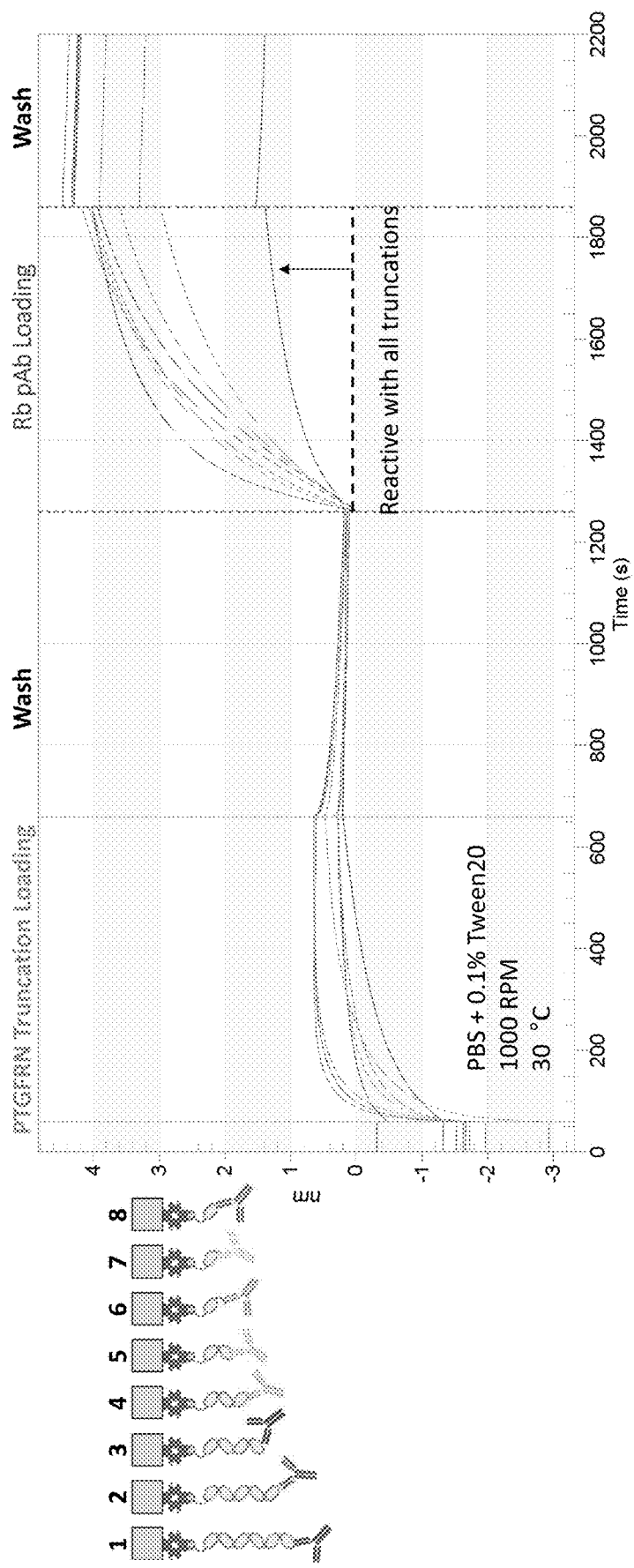

FIG. 30 provides bio-layer interferometry (BLI) results for studying the interaction between polyclonal PTGFRN antibodies and various truncation mutants of PTGFRN.

FIG. 31 provides the number of peptide spectrum matches (PSMs) of surface proteins (PTGFRN, IGSF8, IGSF3, BSG, SLC3A2, ITGB1, CD81, and CD9) for exosomes purified from various cell lines of different origins (HEK293SF, kidney; HT1080, connective tissue; K562, bone marrow; MDA-MB-231, breast; Raji, lymphoblast; mesenchymal stem cell (MSC), bone marrow).

Figure 32B:
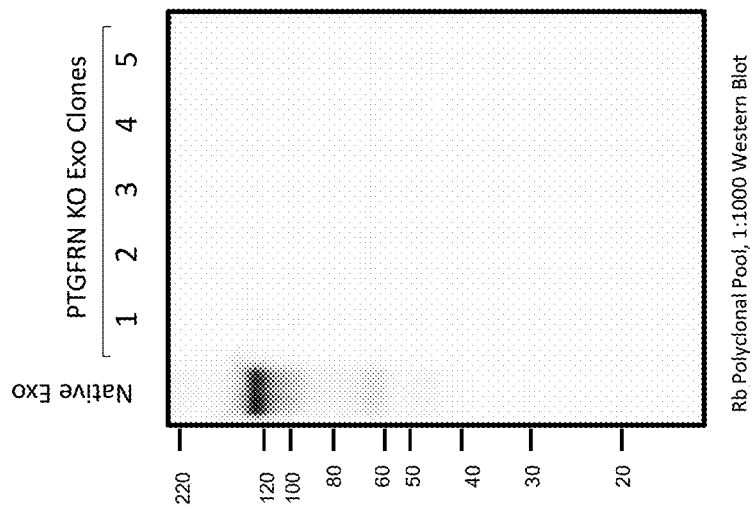
Figure 32A:
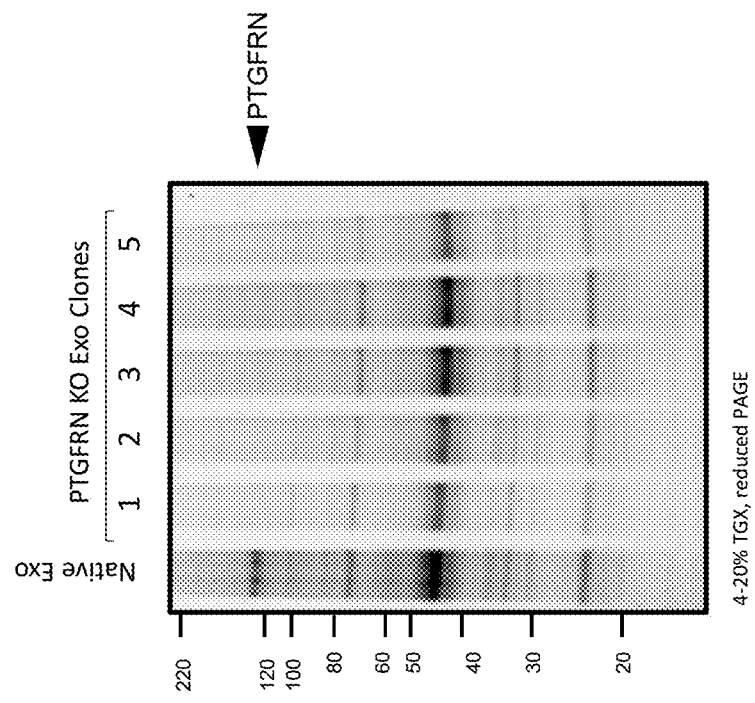

FIG. 32A provides a gel picture running native and PTGFRN knockout (KO) exosomes. FIG. 32B provides a gel picture from western blotting the samples of FIG. 32A using pooled polyclonal PTGFRN antibodies.

Figure 33:
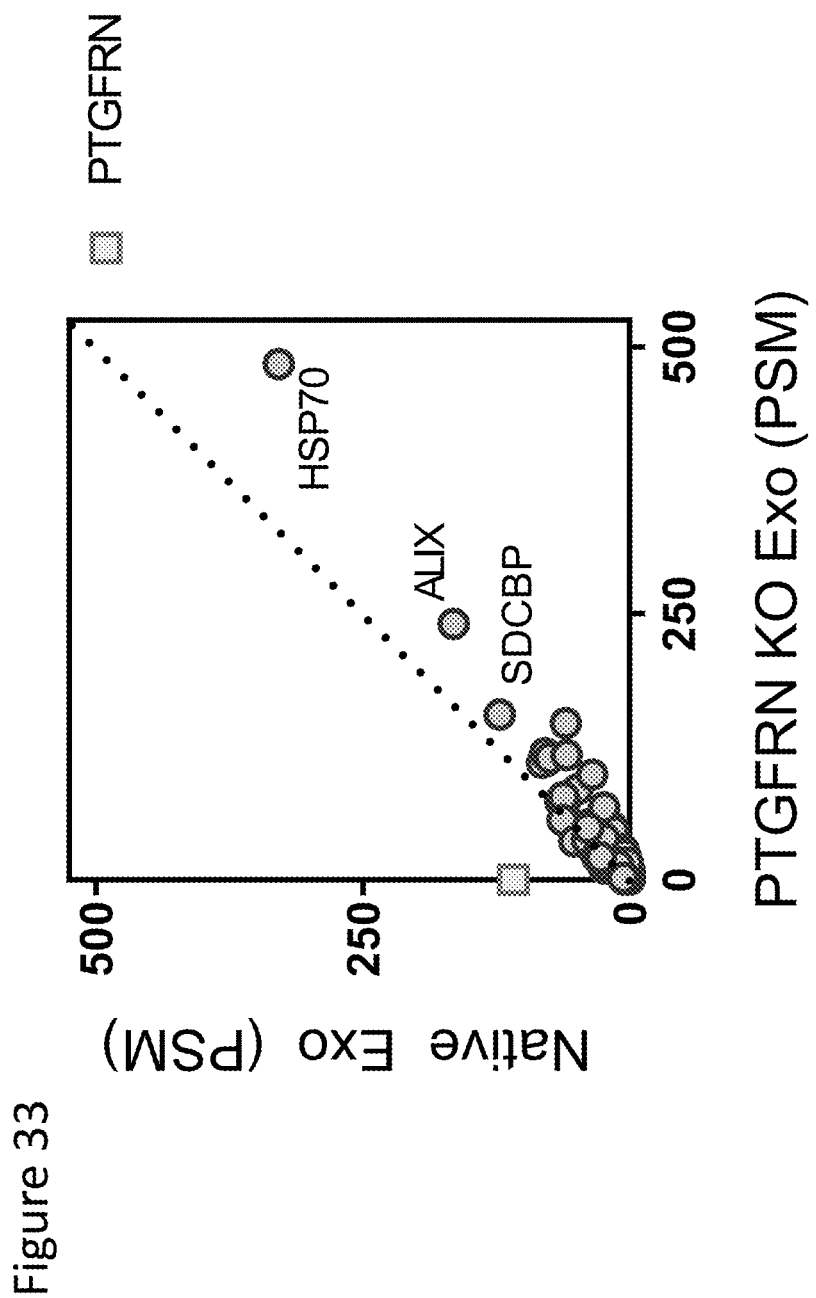

FIG. 33 provides a scatter plot of peptide spectrum matches (PSMs) from purified native (y-axis) and PTGRN KO (x-axis) exosomes.

Figure 34:
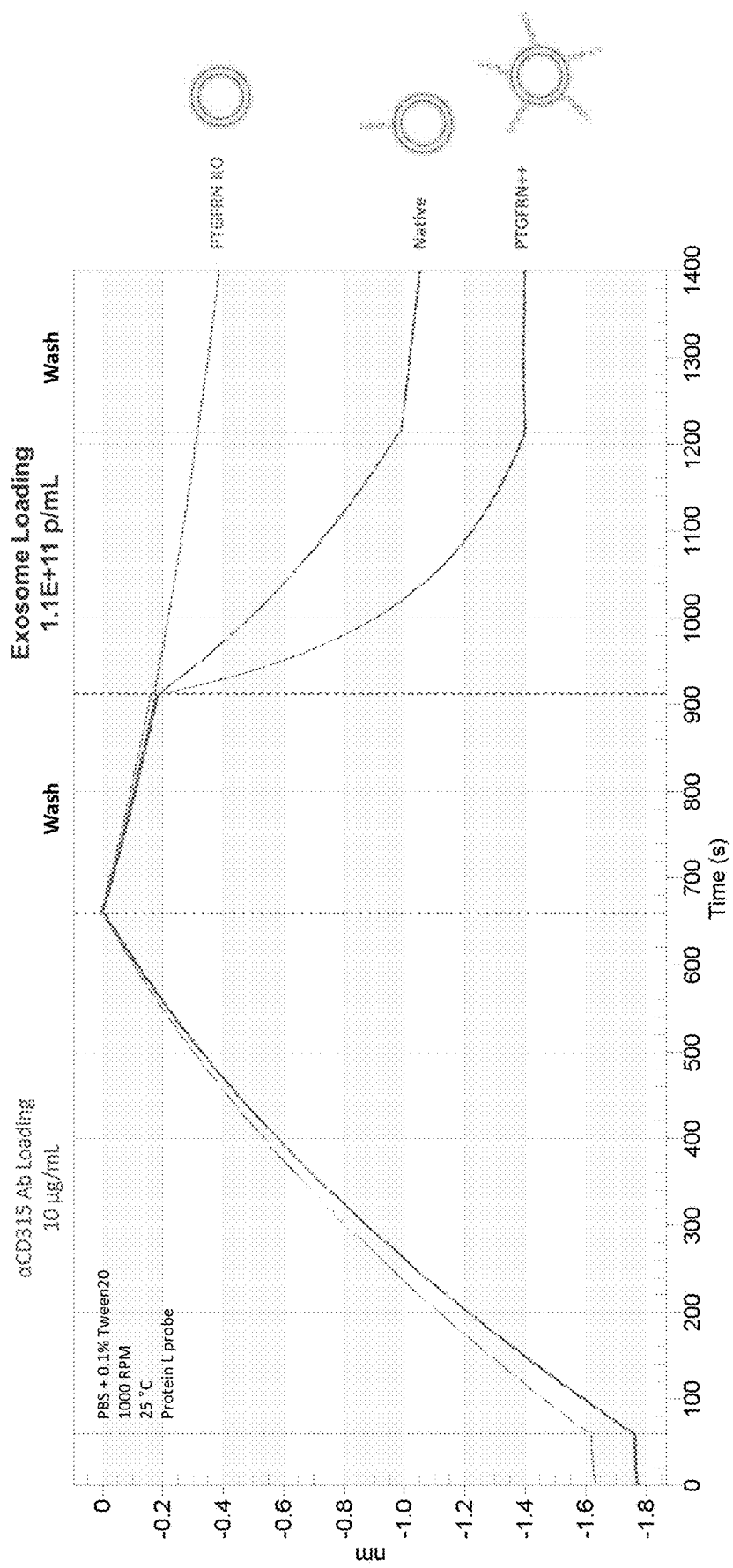

FIG. 34 provides BLI results for studying the interaction between a monoclonal anti-CD315 antibody and either native, PTGFRN++, and PTGFRN KO exosomes.

FIG. 35A provides a picture of a polyacrylamide gel from an in vitro exosome purification of native and PTGFRN knockout (KO) exosomes using an immobilized monoclonal anti-PTGFRN antibody. FIG. 35B provides a gel picture from western blotting the samples of FIG. 35A using an anti-PTGFRN antibody.

Figures 36A, 36B:
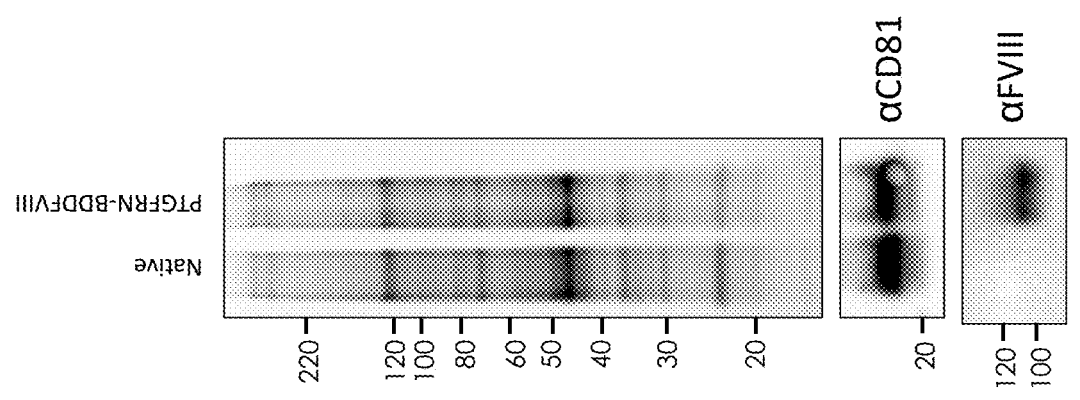

FIG. 36A provides a picture of a polyacrylamide gel running native exosomes or modified exosomes engineered to express PTGFRN-BDDFIII. FIG. 36 B provides a gel picture from western blotting the samples from FIG. 36A using CD81 antibodies (top) or FVIII antibodies (bottom).

Figures 37A, 37B:
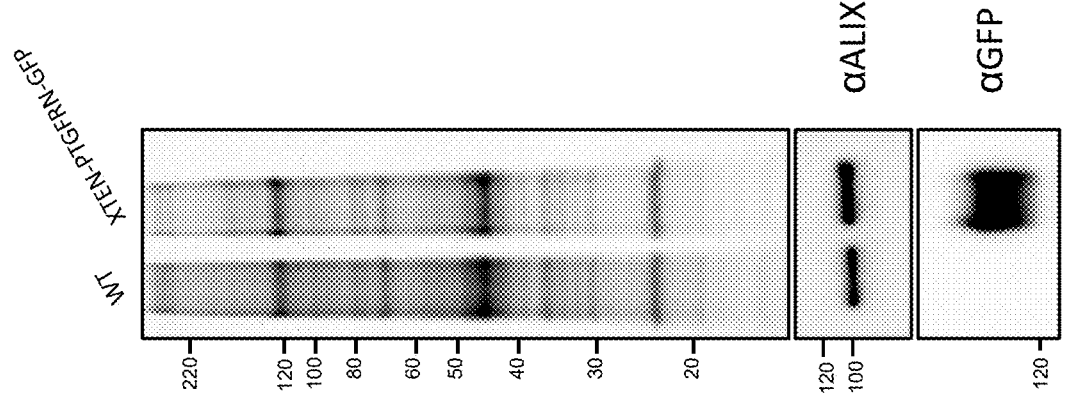

FIG. 37A provides a picture of a polyacrylamide gel running native exosomes or modified exosomes engineered to express XTEN-PTGFRN-GFP. FIG. 37B provides a gel picture from western blotting the samples from FIG. 37A using ALIX antibodies (top) or GFP antibodies (bottom).

Figure 38:
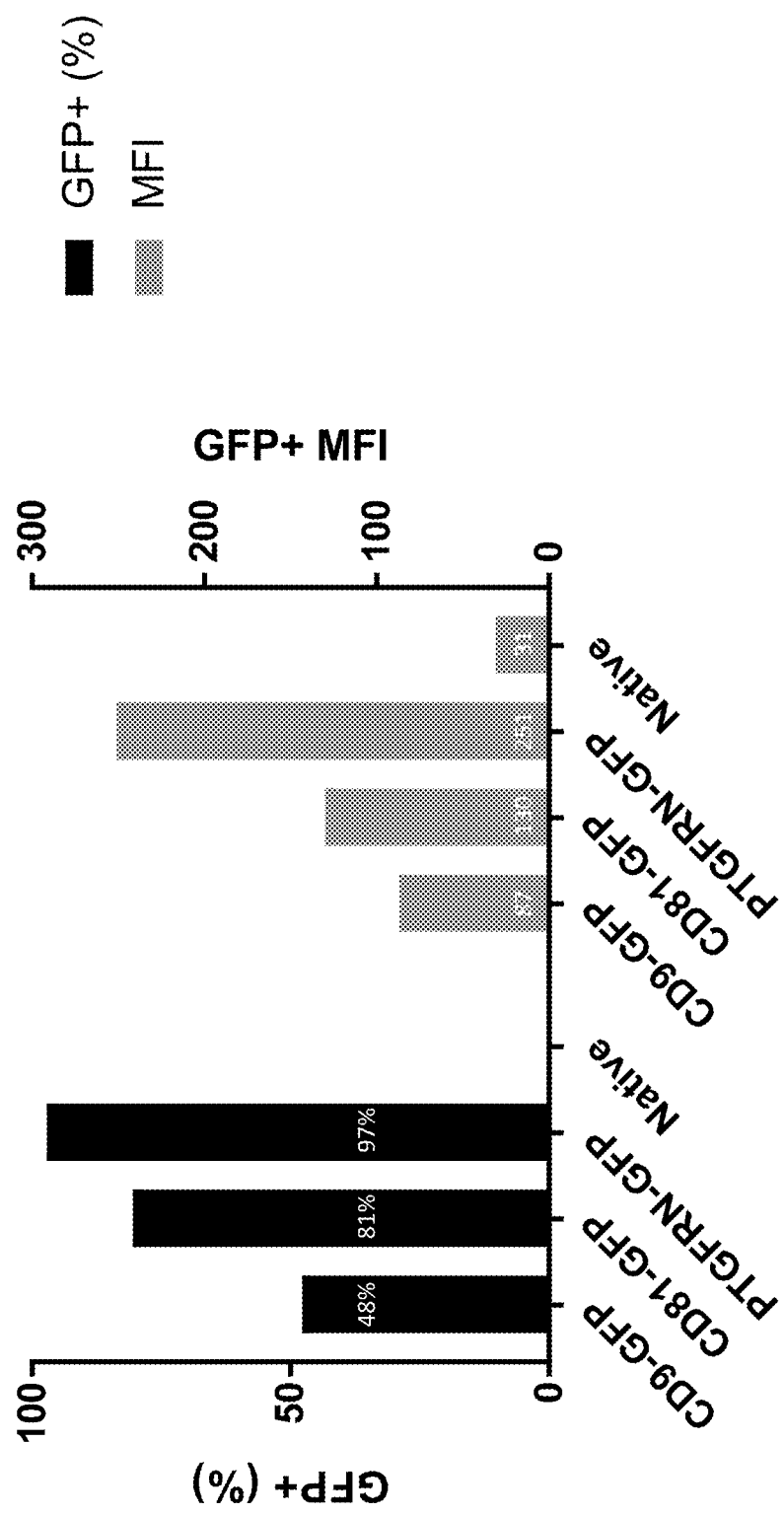

FIG. 38 is a graph providing percentages of GFP-positive particles (black bars, left y-axis) and mean fluorescent intensity (gray bars, right y-axis) in four different groups of exosomes—modified exosomes engineered to express (i) CD9-GFP, (ii) CD81-GFP, or (iii) PTGFRN-GFP, or (iv) unmodified, native exosomes.

Figure 39:
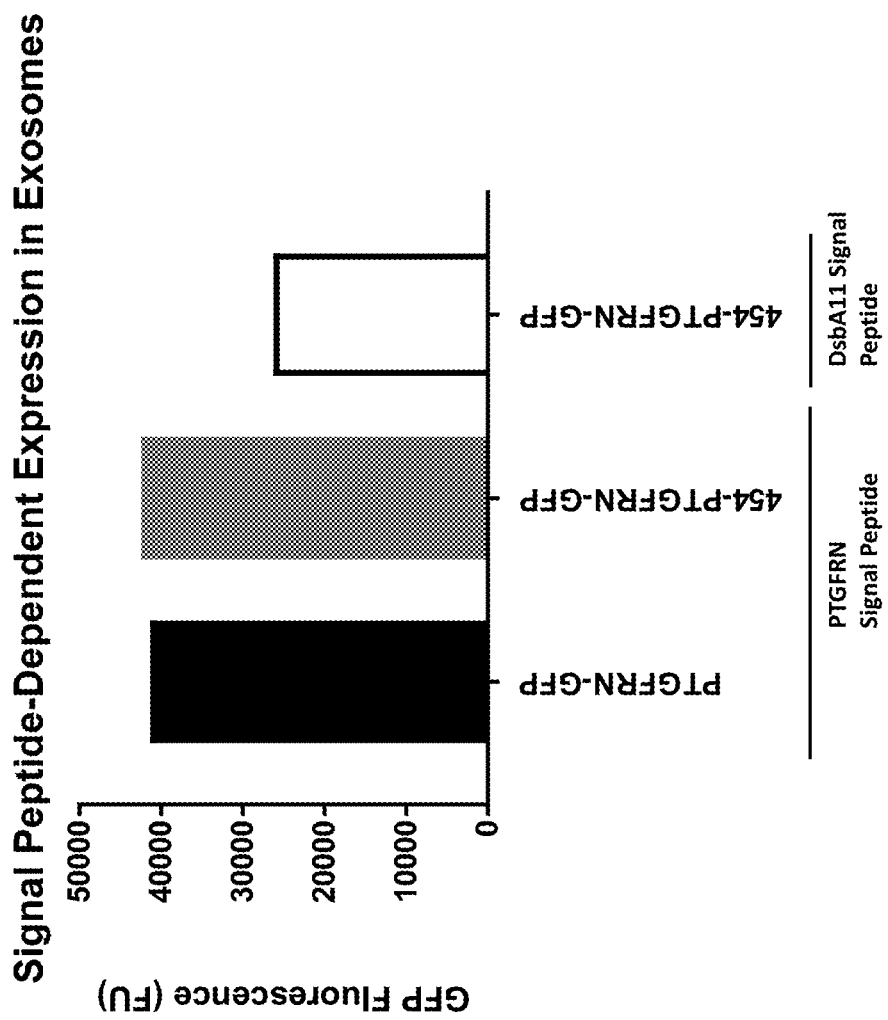

FIG. 39 provides GFP fluorescence intensity (FU) of modified exosomes expressing a GFP fusion protein containing a native PTGFRN (PTGFRN-GFP), a truncated PTGFRN (454-PTGFRN-GFP) with its own signal peptide or a truncated PTGFRN (454-PTGFRN-GFP) with a synthetic signal peptide from DsbA11.

Figure 40B:
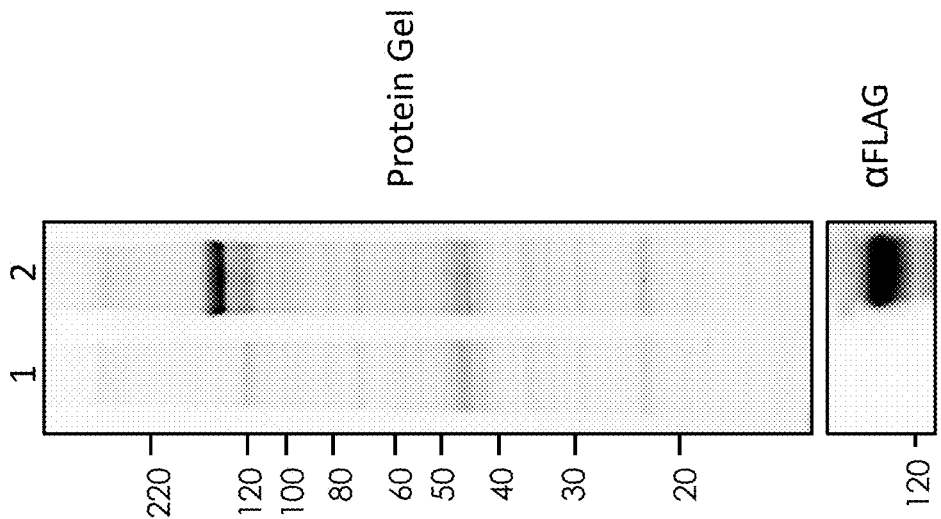
Figure 40A:
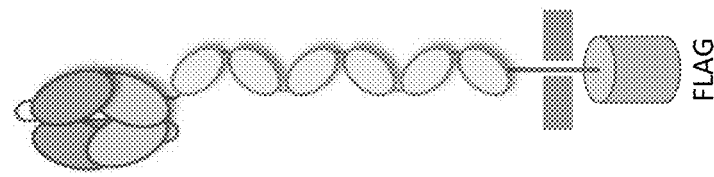

FIG. 40A shows a structure of a fusion protein consisting of a single chain Fab recognizing the lectin CLEC9A, a full-length PTGFRN, GFP, and a FLAG tag. FIG. 40B provides a gel picture from western blotting Optiprep™ purified exosomes using anti-ALIX antibodies (top) or GFP antibodies (bottom).

Figure 41:
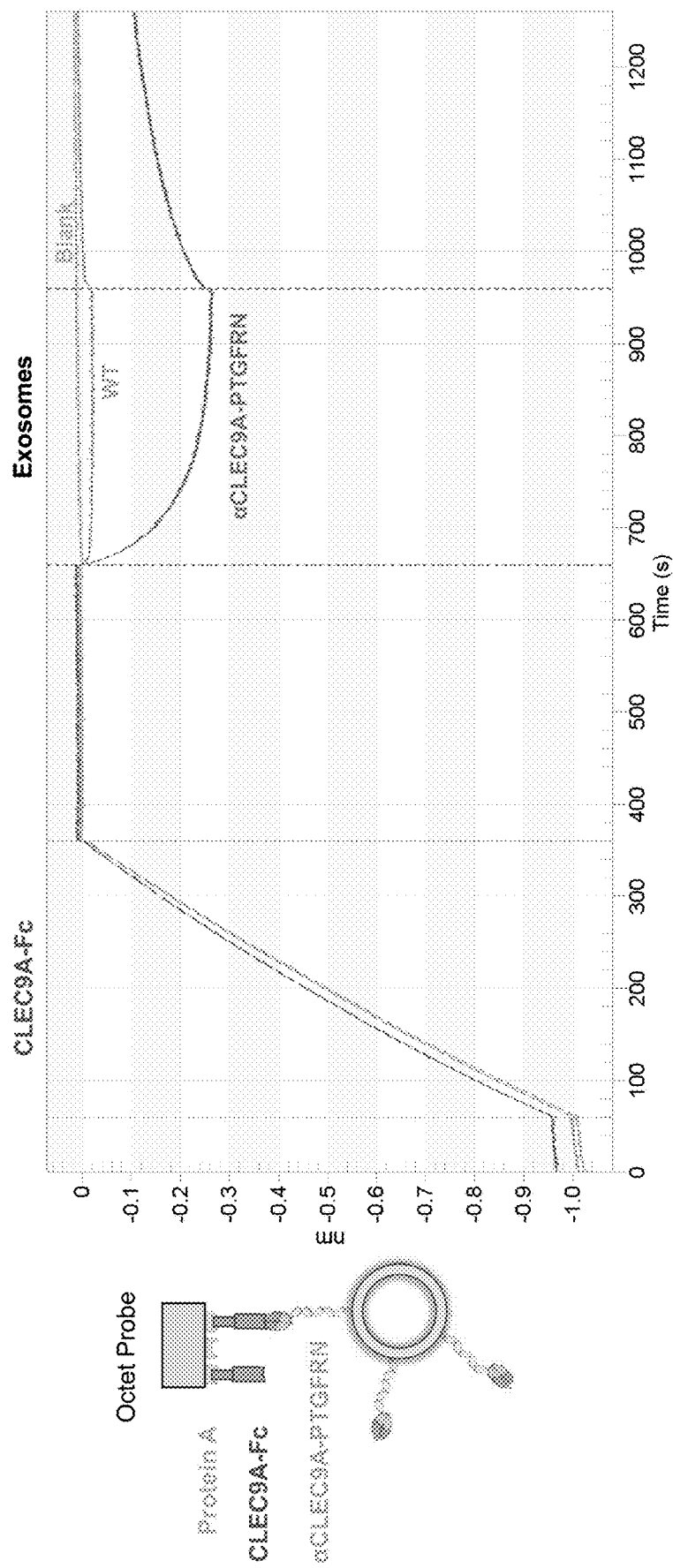

FIG. 41 provides BLI results for studying the interaction between CLEC9A-Fc and exosomes modified to express a fusion protein consisting of a single chain Fab recognizing the lectin CLEC9A, a full-length PTGFRN, GFP, and a FLAG tag ("αCLEC9A-PTGFRN").

Figure 42:
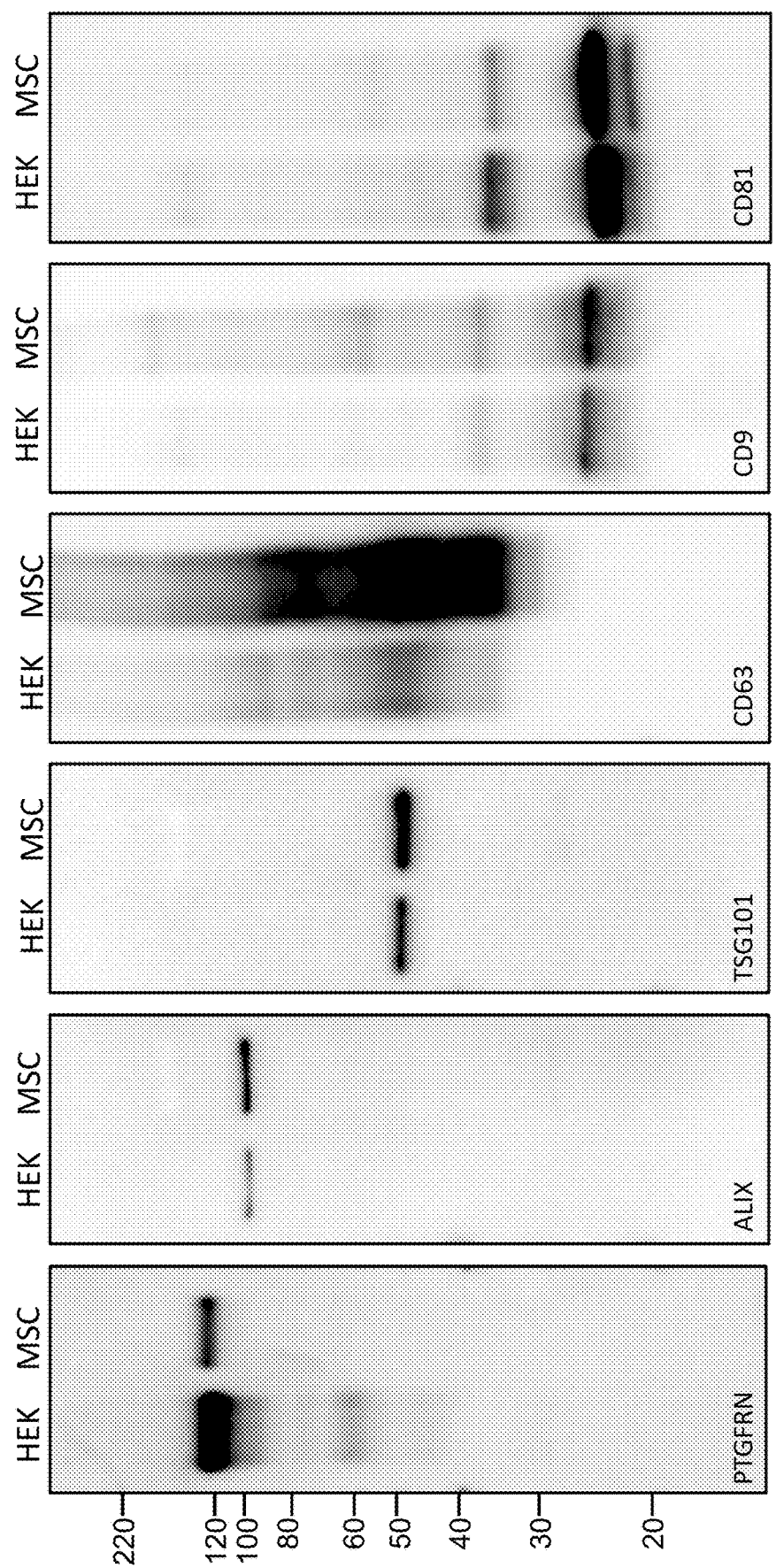

FIG. 42 provides gel pictures from western blotting exosomes purified from HEK293SF cells ("HEK") or MSCs ("MSC") with antibodies against PTGFRN, ALIX, TSG101, CD63, CD9, or CD81.

FIG. 43A provides a picture of a polyacrylamide gel running exosomes purified from untransfected HEK cells, HEK cells transfected with a plasmid expressing full-length PTGFRN fused to a FLAG tag ("the PTGFRN-FLAG plasmid"), untransfected CHO cells, or CHO cells transfected with the PTGFRN-FLAG plasmid. FIG. 43B provides a gel picture from western blotting the samples from FIG. 43A using an antibody against PTGRN. FIG. 43C provides a gel picture from western blotting the samples from FIG. 43A using an antibody against a FLAG tag.

Figure 44A:
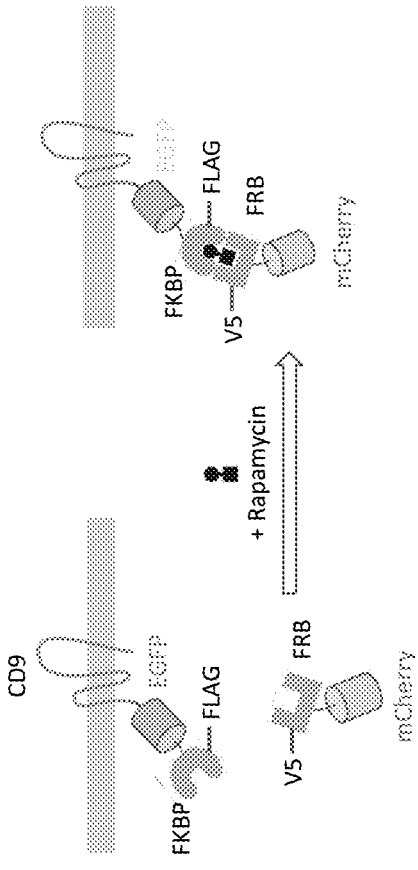
Figure 44B:
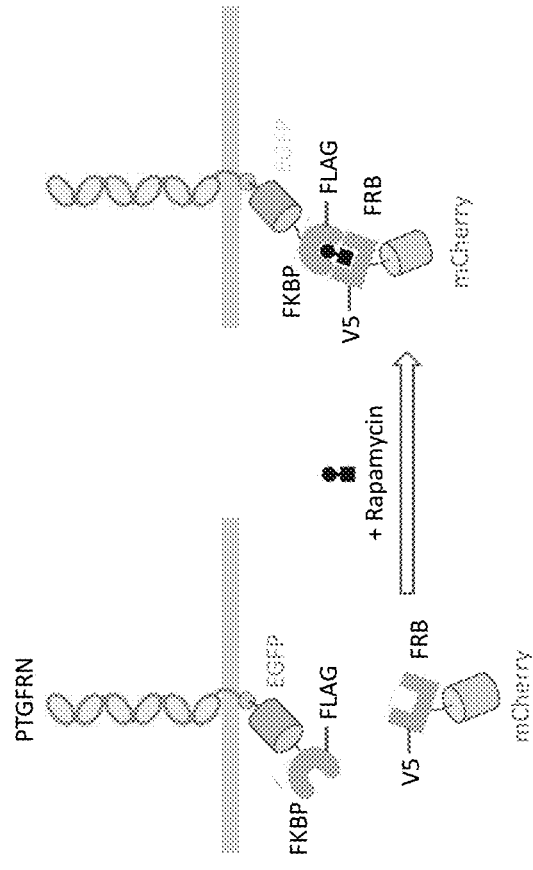

FIGS. 44A-B illustrates an experimental system for testing loading of a cargo protein in the exosome lumen using CD9 (FIG. 44A) or PTGFRN (FIG. 44B). FIG. 44A illustrates a cell expressing CD9 fused to GFP, a FLAG tag and FKBP, which can interact with mCherry fused to a V5 tag and FKBP in the presence of Rapamycin. FIG. 44B illustrates a cell expressing PTGFRN fused to GFP, a FLAG tag and FKBP, which can interact with mCherry fused to a V5 tag and FKBP in the presence of Rapamycin.

Figure 45B:
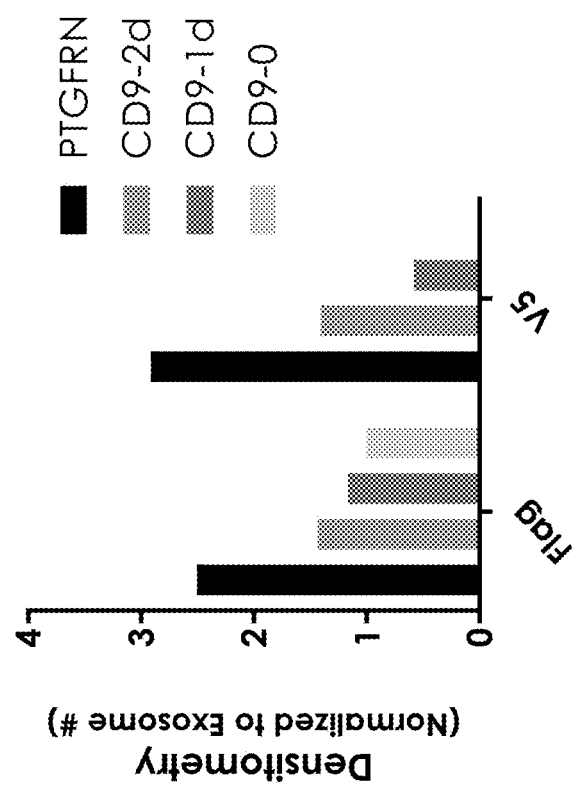
Figure 45A:
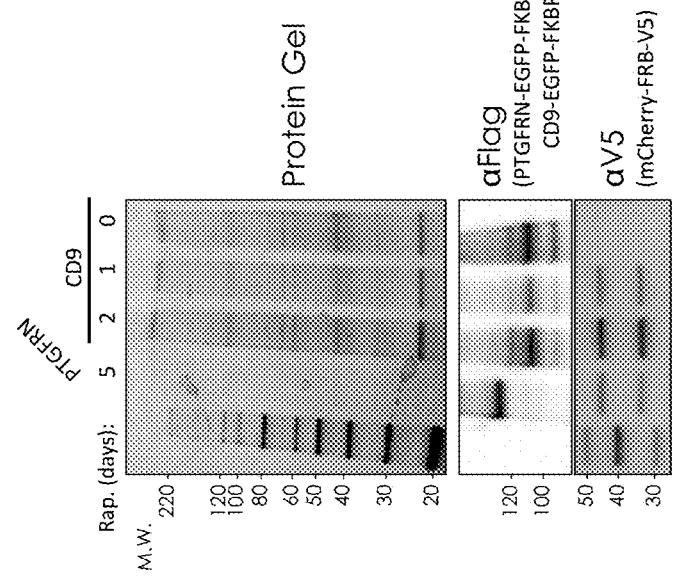

FIG. 45A provides a picture of a polyacrylamide gel running exosomes purified from the cell culture samples illustrated in FIG. 44A (CD9) or FIG. 44B (PTGFRN) (top). The figure also provides the Western blotting results using an antibody against FLAG (αFlag) or V5 (αV5) (bottom). FIG. 45B provides band intensities for FLAG and V5 from the Western blotting in FIG. 45A, measured by densitometry and normalized to the amount of collected exosomes.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

As used herein, the term "extracellular vesicle" or "EV" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. Said cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

As used herein the term "exosome" refers to a cell-derived small (between 20-300 nm in diameter, more preferably 40-200 nm in diameter) vesicle comprising a membrane that encloses an internal space, and which is generated from said cell by direct plasma membrane budding or by fusion of the late endosome with the plasma membrane. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof. An exosome is a species of extracellular vesicle. Generally, exosome production/biogenesis does not result in the destruction of the producer cell.

As used herein, the term "nanovesicle" refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to said manipulation, may be isolated from the producer cell based on its size, density, biochemical parameters, or a combination thereof. A nanovesicle is a species of extracellular vesicle.

As used herein the term "surface-engineered exosome" refers to an exosome with a membrane modified in its composition. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering.

As used herein the term "a modification" of a protein refers to a protein having at least 15% identify to the non-mutant amino acid sequence of the protein. A modification of a protein includes a fragment or a variant of the protein. A modification of a protein can further include chemical, or physical modification to a fragment or a variant of the protein.

As used herein the term "a fragment" of a protein refers to a protein that is N- and/or C-terminally deleted in comparison to the naturally occurring protein. Preferably, a fragment of PTGFRN, BSG, IGSF2, IGSF3, IGSF8, ITGB1, ITGA4, SLC3A2, or ATP transporter retains the ability to be specifically targeted to exosomes. Such a fragment is also referred to as "functional fragment". Whether a fragment is a functional fragment in that sense can be assessed by any art known methods to determine the protein content of exosomes including Western Blots, FACS analysis and fusions of the fragments with autofluorescent proteins like, e.g. GFP. In a particular embodiment the fragment of PTGFRN, BSG, IGSF2, IGSF3, IGSF8, ITGB1, ITGA4, SLC3A2, ATP transporter retains at least 50%, 60%, 70%, 80%, 90% or 100% of the ability of the naturally occurring PTGFRN, BSG, IGSF2, IGSF3, IGSF8, ITGB1, ITGA4, SLC3A2, or ATP transporter to be specifically targeted to exosomes.

As used herein the term "variant" of a protein refers to a protein that shares a certain amino acid sequence identity with another protein upon alignment by a method known in the art. A variant of a protein can include a substitution, insertion, deletion, frameshift or rearrangement in another protein. In a particular embodiment, the variant is a variant having at least 70% identity to PTGFRN, BSG, IGSF2, IGSF3, IGSF8, ITGB1, ITGA4, SLC3A2, ATP transporter or a fragment of PTGFRN, BSG, IGSF2, IGSF3, IGSF8, ITGB1, ITGA4, SLC3A2, or ATP transporter. In some embodiments variants or variants of fragments of PTGFRN share at least 70%, 80%, 85%, 90%, 95% or 99% sequence identity with PTGFRN according to SEQ ID NO: 1 or with a functional fragment thereof. In some embodiments variants or variants of fragments of BSG share at least 70%, 80%, 85%, 90%, 95% or 99% sequence identity with BSG according to SEQ ID NO: 9 or with a functional fragment thereof. In some embodiments variants or variants of fragments of IGSF2 share at least 70%, 80%, 85%, 90%, 95% or 99% sequence identity with IGSF2 according to SEQ ID NO: 34 or with a functional fragment thereof. In some embodiments variants or variants of fragments of IGSF3 share at least 70%, 80%, 85%, 90%, 95% or 99% sequence identity with IGSF3 according to SEQ ID NO: 20 or with a functional fragment thereof. In some embodiments variants or variants of fragments of IGSF8 share at least 70%, 80%, 85%, 90%, 95% or 99% sequence identity with IGSF8 according to SEQ ID NO: 14 or with a functional fragment thereof. In some embodiments variants or variants of fragments of ITGB1 share at least 70%, 80%, 85%, 90%, 95% or 99% sequence identity with ITGB1 according to SEQ ID NO: 21 or with a functional fragment thereof. In some embodiments variants or variants of fragments of ITGA4 share at least 70%, 80%, 85%, 90%, 95% or 99% sequence identity with ITGA4 according to SEQ ID NO: 22 or with a functional fragment thereof. In some embodiments variants or variants of fragments of SLC3A2 share at least 70%, 80%, 85%, 90%, 95% or 99% sequence identity with SLC3A2 according to SEQ ID NO: 23 or with a functional fragment thereof. In some embodiments variants or variants of fragments of ATP1A1 share at least 70%, 80%, 85%, 90%, 95% or 99% sequence identity with ATP1A1 according to SEQ ID NO: 24 or with a functional fragment thereof. In some embodiments variants or variants of fragments of ATP1A2 share at least 70%, 80%, 85%, 90%, 95% or 99% sequence identity with ATP1A2 according to SEQ ID NO: 25 or with a functional fragment thereof. In some embodiments variants or variants of fragments of ATP1A3 share at least 70%, 80%, 85%, 90%, 95% or 99% sequence identity with ATP1A3 according to SEQ ID NO: 26 or with a functional fragment thereof. In some embodiments variants or variants of fragments of ATP1A4 share at least 70%, 80%, 85%, 90%, 95% or 99% sequence identity with ATP1A4 according to SEQ ID NO: 27 or with a functional fragment thereof. In some embodiments variants or variants of fragments of ATP1B3 share at least 70%, 80%, 85%, 90%, 95% or 99% sequence identity with ATP1B3 according to SEQ ID NO: 28 or with a functional fragment thereof. In some embodiments variants or variants of fragments of ATP2B1 share at least 70%, 80%, 85%, 90%, 95% or 99% sequence identity with ATP2B1 according to SEQ ID NO: 29 or with a functional fragment thereof. In some embodiments variants or variants of fragments of ATP2B2 share at least 70%, 80%, 85%, 90%, 95% or 99% sequence identity with ATP2B2 according to SEQ ID NO: 30 or with a functional fragment thereof. In some embodiments variants or variants of fragments of ATP2B3 share at least 70%, 80%, 85%, 90%, 95% or 99% sequence identity with ATP2B3 according to SEQ ID NO: 31 or with a functional fragment thereof. In some embodiments variants or variants of fragments of ATP2B4 share at least 70%, 80%, 85%, 90%, 95% or 99% sequence identity with ATP2B4 according to SEQ ID NO: 32 or with a functional fragment thereof. In each of above cases, it is preferred that the variant or variant of a fragment retains the ability to be specifically targeted to exosomes.

Methods of alignment of sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol.

Biol. 24: 307-31 (1988); Higgins and Sharp, Gene 73: 237-44 (1988); Higgins and Sharp, CABIOS 5: 151-3 (1989) Corpet et al., Nuc. Acids Res. 16: 10881-90 (1988); Huang et al., Comp. Appl. BioSci. 8: 155-65 (1992); and Pearson et al., Meth. Mol. Biol. 24: 307-31 (1994). The NCBI Basic Local Alignment Search Tool (BLAST) [Altschul 20 et al., J. Mol. Biol. 215: 403-10 (1990) J is available from several sources, including the National Center for Biological Information (NBCl, Bethesda, Md.) and on the Internet, for use in connection with the sequence analysis programs blastp, blasm, blastx, tblastn and tblastx. BLAST and a description of how to determine sequence identify using the program can be accessed at the official website of NCBI (National Center for Biotechnology Information) under NIH (National Institute of Health).

Recitation of any protein provided herein encompasses a functional variant of the protein. The term "functional variant" of a protein refers to a variant of the protein that retains the ability to be specifically targeted to exosomes.

As used herein the term "producer cell" refers to a cell used for generating an exosome. A producer cell can be a cell cultured in vitro, or a cell in vivo. A producer cell includes, but is not limited to, a cell known to be effective in generating exosomes, e.g., HEK293 cells, Chinese hamster ovary (CHO) cells, and mesenchymal stem cells (MSCs).

As used herein the term "target protein" refers to a protein that can be targeted to the surface of an exosome. The target protein can be a non-mutant protein that is naturally targeted to an exosome membrane, or a fragment or a variant of the non-mutant protein. The target protein can be a fusion protein containing a flag tag, a therapeutic peptide, a targeting moiety, or other peptide attached to the non-mutant protein or a variant or a fragment of the non-mutant protein. The target protein can comprise a transmembrane protein, an integral protein, a peripheral protein, or a soluble protein attached to the membrane by a linker.

As used herein the term "contaminant protein" refers to a protein that is not associated with an exosome. For example, a contaminant protein includes a protein, not enclosed in the exosome and not attached to or incorporated into the membrane of the exosome.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired exosome preparation. In some embodiments, isolating or purifying as used herein is the process of removing, partially removing (e.g., a fraction) of the exosomes from a sample containing producer cells. In some embodiments, an isolated exosome composition has no detectable undesired activity or, alternatively, the level or amount of the undesired activity is at or below an acceptable level or amount. In other embodiments, an isolated exosome composition has an amount and/or concentration of desired exosomes at or above an acceptable amount and/or concentration. In other embodiments, the isolated exosome composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated exosome preparations are substantially free of residual biological products. In some embodiments, the isolated exosome preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the exosome composition contains no detectable producer cells and that only exosomes are detectable.

The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins).

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, the term "substantially free" means that the sample comprising exosomes comprise less than 10% of macromolecules by mass/volume (m/v) percentage concentration. Some fractions may contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in exosomes, including but is not limited to CD9, CD63, CD81, PDGFR, GPI anchor proteins, lactadherin LAMP2, and LAMP2B, a fragment thereof, or a peptide that binds thereto.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

6.3. Exosome Proteins

An aspect of the present invention relates to identification, use and modification of exosome proteins, which are highly enriched on exosome membranes. Such exosome proteins can be identified by analyzing highly purified exosomes with mass spectrometry or other methods known in the art.

The exosome proteins include various membrane proteins, such as transmembrane proteins, integral proteins and peripheral proteins, enriched on the exosome membranes. They include various CD proteins, transporters, integrins, lectins and cadherins. Specifically, the proteins include, but are not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9), immunoglobulin superfamily member 2 (IGSF2).

One or more exosome proteins identified herein can be selectively used depending on a producer cell, production condition, purification methods, or intended application of the exosomes. For example, exome proteins enriched on a specific population of exosomes can be used to purify the specific population of exosomes. Exosome proteins enriched on the surface of certain exosomes with a specific size range, a targeting moiety, a charge density, a payload, etc. can be identified and used in some embodiments of the present invention. In some embodiments, more than one exosome proteins can be used concurrently or subsequently for generation, purification, and isolation of therapeutic exosomes.

6.4. Surface-Engineered Exosomes

Another aspect of the present invention relates to generation and use of surface-engineered exosomes. Surface-engineered exosomes have a membrane modified in its compositions. For example, their membrane compositions can be modified by changing the protein, lipid or glycan content of the membrane.

In some embodiments, the surface-engineered exosomes are generated by chemical and/or physical methods, such as PEG-induced fusion and/or ultrasonic fusion.

In other embodiments, the surface-engineered exosomes are generated by genetic engineering. Exosomes produced from a genetically-modified producer cell or a progeny of the genetically-modified cell can contain modified membrane compositions. In some embodiments, surface-engineered exosomes have the exosome protein at a higher or lower density or include a variant or a fragment of the exosome protein.

For example, surface-engineered exosomes can be produced from a cell transformed with an exogenous sequence encoding the exosome protein or a variant or a fragment of the exosome protein. Exosomes including proteins expressed from the exogenous sequence can include modified membrane protein compositions.

Various modifications or fragments of the exosome protein can be used for the embodiments of the present invention. For example, proteins modified to have enhanced affinity to a binding agent can be used for generating surface-engineered exosomes that can be purified using the binding agent. Proteins modified to be more effectively targeted to exosomes and/or membranes can be used. Proteins modified to comprise a minimal fragment required for specific and effective targeting to exosome membranes can be also used.

Fusion proteins can be also used, for example, exosome proteins or their fragments fused to an affinity tag (e.g., His tag, GST tag, glutathione-S-transferase, S-peptide, HA, Myc, FLAG™ (Sigma-Aldrich Co.), MBP, SUMO, and Protein A) can be used for purification or removal of the surface-engineered exosomes with a binding agent specific to the affinity tag.

Fusion proteins having a therapeutic activity can be also used for generating surface-engineered exosomes. For example, the fusion protein can comprise PTGFRN, BSG, IGSF2, IGSF3, IGSF8, ITGB1, ITGA4, SLC3A2, ATP transporter, or a fragment or a variant thereof, and a therapeutic peptide. The therapeutic peptide is selected from the group consisting of a natural peptide, a recombinant peptide, a synthetic peptide, or a linker to a therapeutic compound. The therapeutic compound can be nucleotides, amino acids, lipids, carbohydrates, or small molecules. The therapeutic peptide can be an antibody, an enzyme, a ligand, a receptor, an antimicrobial peptide or a fragment or a variant thereof. In some embodiments, the therapeutic peptide is a nucleic acid binding protein. The nucleic acid binding protein can be Dicer, an Argonaute protein, TRBP, or MS2 bacteriophage coat protein. In some embodiments, the nucleic acid binding protein additionally comprises one or more RNA or DNA molecules. The one or more RNA can be a miRNA, siRNA, guide RNA, lincRNA, mRNA, antisense RNA, dsRNA, or combinations thereof.

In some embodiments, the therapeutic peptide is a part of a protein-protein interaction system. In some embodiments, the protein-protein interaction system comprises an FRB-FKBP interaction system, e.g., the FRB-FKBP interaction system as described in Banaszynski et al., J Am Chem Soc. 2005 Apr. 6; 127(13):4715-21.

The fusion proteins can be targeted to the surface of exosomes and provide a therapeutic activity to the exosome. In some embodiments, the fusion protein does not comprise IGSF8 or a fragment or modification thereof.

In some embodiments, fusion proteins having a targeting moiety are used. For example, fusion proteins can comprise PTGFRN, BSG, IGSF2, IGSF3, IGSF8, ITGB1, ITGA4, SLC3A2, ATP transporter, or a fragment or a variant thereof, and a targeting moiety. The targeting moiety can be used for targeting the exosome to a specific organ, tissue, or cell for a treatment using the exosome. In some embodiments, the targeting moiety is an antibody or antigen-binding fragment thereof. Antibodies and antigen-binding fragments thereof include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibodies and antigen-binding fragments thereof also includes bispecific antibodies and multispecific antibodies so long as they exhibit the desired biological activity or function.

In some embodiments, the fusion protein does not comprise IGSF8 or a fragment or modification thereof.

In some embodiments, the surface-engineered exosomes described herein demonstrate superior characteristics compared to surface-engineered exosomes known in the art. For example, surface-engineered exosomes produced by using the newly-identified exosome proteins provided herein contain modified proteins more highly enriched on their surface than exosomes in prior art, e.g., those produced using conventional exosome proteins. Moreover, the surface-engineered exosomes of the present invention can have greater, more specific, or more controlled biological activity compared to surface-engineered exosomes known in the art. For example, a surface engineered exosome comprising a therapeutic or biologically relevant exogenous sequence fused to an exosome surface protein or a fragment thereof described herein (e.g., PTGFRN or a fragment thereof) can have more of the desired engineered characteristics than fusion to scaffolds known in the art. Scaffold proteins known in the art include tetraspanin molecules (e.g., CD63, CD81, CD9 and others), lysosome-associated membrane protein 2 (LAMP2 and LAMP2B), platelet-derived growth factor receptor (PDGFR), GPI anchor proteins, lactadherin and fragments thereof, and peptides that have affinity to any of these proteins or fragments thereof. Previously, overexpression of exogenous proteins relied on stochastic or random disposition of the exogenous proteins onto the exosome for producing surface-engineered exosomes. This resulted in low-level, unpredictable density of the exogenous proteins on exosomes. Thus, the exosome surface proteins and fragments thereof described herein provide important advancements in novel exosome compositions and methods of making the same.

In some embodiments, the surface-engineered exosome comprising a fusion protein containing an exogenous sequence and an exosome surface protein newly-identified herein has a higher density of the fusion protein than similarly engineered exosomes comprising an exogenous sequence conjugated to a conventional exosome protein known in the art (e.g., CD9, CD63, CD81, PDGFR, GPI anchor proteins, lactadherin LAMP2, and LAMP2B, a fragment thereof, or a peptide that binds thereto). In some embodiments, said fusion protein containing an exosome protein newly-identified herein is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein. In some embodiments, said fusion protein containing an exosome protein newly-identified herein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on the exosome surface than fusion proteins on other exosome surfaces similarly modified using a conventional exosome protein.

In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD9. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD63. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD81. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using PDGFR. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using GPI anchor proteins. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using lactadherin. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using LAMP2. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using LAMP2B. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a fragment of a conventional exosome protein. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a variant of a conventional exosome protein.

In particular embodiments a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of BSG, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of IGSF2, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63).

In particular embodiments a fusion protein of IGSF3, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of IGSF8, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ITGB1, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ITGA4, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of SLC3A2, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ATP transporter, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In some embodiments, said fusion protein containing an exosome protein newly-identified herein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on the exosome surface than fusion proteins on other exosome surfaces similarly modified using a conventional exosome protein.

Fusion proteins provided herein can comprise PTGFRN, BSG, IGSF2, IGSF3, IGSF8, ITGB1, ITGA4, SLC3A2, ATP transporter, or a fragment or a variant thereof, and an additional peptide. The additional peptide can be attached to either the N terminus or the C terminus of the exosome protein or a fragment or a variant thereof. The additional peptide can be located inside (in the luminal side) or outside of the exosome attached to the exosome protein.

In some embodiments, fusion proteins provided herein comprise PTGFRN, BSG, IGSF2, IGSF3, IGSF8, ITGB1, ITGA4, SLC3A2, ATP transporter, or a fragment or a variant thereof, and two additional peptides. Both of the two additional peptides can be attached to either the N terminus or the C terminus of the exosome protein or a fragment or a variant thereof. In some embodiments, one of the two additional peptides is attached to the N terminus and the other of the two additional peptides is attached to the C terminus of the exosome protein or a fragment or a variant thereof. The additional peptides can be located inside (in the luminal side) or outside of the exosome attached to the exosome protein, or both.

6.5. Producer Cell for Production of Surface-Engineered Exosomes

Exosomes of the present invention can be produced from a cell grown in vitro or a body fluid of a subject. When exosomes are produced from in vitro cell culture, various producer cells, e.g., HEK293 cells, Chinese hamster ovary (CHO) cells, or mesenchymal stem cells (MSCs), can be used for the present invention.

The producer cell can be genetically modified to comprise one or more exogenous sequences to produce surface-engineered exosomes. The genetically-modified producer cell can contain the exogenous sequence introduced by transient or stable transformation. The exogenous sequence can be introduced to the producer cell as a plasmid. The exogenous sequences can be stably integrated into a genomic sequence of the producer cell, at a targeted site or in a random site. In some embodiments, a stable cell line is generated for production of surface-engineered exosomes.

The exogenous sequences can be inserted into a genomic sequence of the producer cell, located within, upstream (5'-end) or downstream (3'-end) of an endogenous sequence encoding the exosome protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present invention.

The exogenous sequences can comprise a sequence encoding the exosome protein or a variant or a fragment of the exosome protein. An extra copy of the sequence encoding the exosome protein can be introduced to produce a surface-engineered exosome having the exosome protein at a higher density. An exogenous sequence encoding a variant or a fragment of the exosome protein can be introduced to produce a surface-engineered exosome containing the modification or the fragment of the exosome protein. An exogenous sequence encoding an affinity tag can be introduced to produce a surface-engineered exosome containing a fusion protein comprising the affinity tag attached to the exosome protein.

In some embodiments, a surface-engineered exosome has a higher density of the exosome protein than native exosomes isolated from the same or similar producer cell types. In some embodiments, said exosome protein is present at 2-, 4-, 8-, 16-, 32-, 64-, 100-, 200-, 400-, 800-, 1,000-fold or to a higher density on said surface-engineered exosome than said native exosome. In some embodiments, said exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than said native exosome. In some embodiments, a fusion protein comprising the exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified exosome protein on said native exosome. In some embodiments, a fragment or a variant of the exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified exosome protein on said native exosome.

In particular embodiments, PTGFRN, a fragment or a variant of PTGFRN, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified PTGFRN on said native exosome. In particular embodiments, BSG, a fragment or a variant of BSG, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified BSG on said native exosome. In particular embodiments, IGSF2, a fragment or a variant of IGSF2, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified IGSF2 on said native exosome. In particular embodiments, IGSF3, a fragment or a variant of IGSF3, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified IGSF3 on said native exosome. In particular embodiments, ITGB1, a fragment or a variant of ITGB1, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ITGB1 on said native exosome. In particular embodiments, ITGA4, a fragment or a variant of ITGA4, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ITGA4 on said native exosome. In particular embodiments, SLC3A2, a fragment or a variant of SLC3A2, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified SLC3A2 on said native exosome. In particular embodiments, ATP transporter, a fragment or a variant of ATP transporter, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ATP transporter on said native exosome.

In some embodiments, the producer cell is further modified to comprise an additional exogenous sequence. For example, an additional exogenous sequence can be introduced to modulate endogenous gene expression, or produce an exosome including a certain polypeptide as a payload. In some embodiments, the producer cell is modified to comprise two exogenous sequences, one encoding the exosome protein or a variant or a fragment of the exosome protein, and the other encoding a payload. In some embodiments, the producer cell can be further modified to comprise an additional exogenous sequence conferring additional functionalities to exosomes, for example, specific targeting capabilities, delivery functions, enzymatic functions, increased or decreased half-life in vivo, etc. In some embodiments, the producer cell is modified to comprise two exogenous sequences, one encoding the exosome protein or a variant or a fragment of the exosome protein, and the other encoding a protein conferring the additional functionalities to exosomes.

In some embodiments, the producer cell is modified to comprise two exogenous sequences, each of the two exogenous sequences encoding a fusion protein on the exosome surface. In some embodiments, a surface-engineered exosome from the producer cell has a higher density of an exosome protein compared to native exosomes isolated from an unmodified cell of the same or similar cell type. In some embodiments, surface-engineered exosome contain an exosome protein at a density 2-, 4-, 8-, 16-, 32-, 64-, 100-, 200-, 400-, 800-, 1,000-fold or higher than a native exosome isolated from an unmodified cell of the same or similar cell type. In some embodiments, the producer cell is further modified to comprise one, two, three, four, five, six, seven, eight, nine, or ten or more additional exogenous sequences.

More specifically, surface-engineered exosomes can be produced from a cell transformed with a sequence encoding one or more exosome surface proteins or a variant thereof including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). Any of the one or more exosome surface proteins described herein can be expressed in the producer cell from a plasmid, an exogenous sequence inserted into the genome or other exogenous nucleic acid such as a synthetic messenger RNA (mRNA).

In some embodiments, the one or more exosome surface protein is expressed in a cell transformed with an exogenous sequence encoding its full length, endogenous form. In some embodiments, such an exogenous sequence encodes PTGFRN protein of SEQ ID NO: 1. In some embodiments, such an exogenous sequence encodes BSG protein of SEQ ID NO: 9. In some embodiments, such an exogenous sequence encodes IGSF8 protein of SEQ ID NO: 14. In some embodiments, such an exogenous sequence encodes IGSF3 protein of SEQ ID NO: 20. In some embodiments, such an exogenous sequence encodes ITGB1 protein of SEQ ID NO: 21. In some embodiments, such an exogenous sequence encodes ITGA4 protein of SEQ ID NO: 22. In some embodiments, such an exogenous sequence encodes SLC3A2 protein of SEQ ID NO: 23. In some embodiments, such an exogenous sequence encodes ATP1A1 protein of SEQ ID NO: 24. In some embodiments, such an exogenous sequence encodes ATP1A2 protein of SEQ ID NO: 25. In some embodiments, such an exogenous sequence encodes ATP1A3 protein of SEQ ID NO: 26. In some embodiments, such an exogenous sequence encodes ATP1A4 protein of SEQ ID NO: 27. In some embodiments, such an exogenous sequence encodes ATP1B3 protein of SEQ ID NO: 28. In some embodiments, such an exogenous sequence encodes ATP2B1 protein of SEQ ID NO: 29. In some embodiments, such an exogenous sequence encodes ATP2B2 protein of SEQ ID NO: 30. In some embodiments, such an exogenous sequence encodes ATP2B3 protein of SEQ ID NO: 31. In some embodiments, such an exogenous sequence encodes ATP2B4 protein of SEQ ID NO: 32. In some embodiments, such an exogenous sequence encodes IGSF2 protein of SEQ ID NO: 34

Surface-engineered exosomes can be produced from a cell transformed with a sequence encoding a fragment of one or more exosome surface proteins including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). In some embodiments, the sequence encodes a fragment of the exosome surface protein lacking at least 5, 10, 50, 100, 200, 300, 400, 500, 600, 700, or 800 amino acids from the N-terminus of the native protein. In some embodiments, the sequence encodes a fragment of the exosome surface protein lacking at least 5, 10, 50, 100, 200, 300, 400, 500, 600, 700, or 800 amino acids from the C-terminus of the native protein. In some embodiments, the sequence encodes a fragment of the exosome surface protein lacking at least 5, 10, 50, 100, 200, 300, 400, 500, 600, 700, or 800 amino acids from both the N-terminus and C-terminus of the native protein. In some embodiments, the sequence encodes a fragment of the exosome surface protein lacking one or more functional or structural domains of the native protein.

In some embodiments, the fragment of the exosome surface protein is fused to one or more heterologous proteins. In some embodiments, the one or more heterologous proteins are fused to the N-terminus of the fragment. In some embodiments, the one or more heterologous proteins are fused to the C-terminus of the fragment. In some embodiments, the one or more heterologous proteins are fused to the N-terminus and the C-terminus of the fragment. In some embodiments, the one or more heterologous proteins are mammalian proteins. In some embodiments, the one or more heterologous proteins are human proteins.

Surface engineered exosomes can be produced from a cell transformed with a sequence encoding fragments of PTGFRN. In some embodiments, the fragments of PTGFRN lack one or more functional or structural domains, such as IgV. For example, the fragment of PTGFRN can comprise a polypeptide of SEQ ID NO: 2-7, or 33. In some embodiments, the fragments of PTGFRN are fused to one or more heterologous proteins. The one or more heterologous proteins can be fused to the N-terminus of said PTGFRN fragments. The one or more heterologous proteins can be fused to the C-terminus of said PTGFRN fragments. In some embodiments, the one or more heterologous proteins are fused to both the N-terminus and the C-terminus of said PTGFRN fragments. In some embodiments, the heterologous protein is a mammalian protein. In some embodiments, the heterologous protein is a human protein. In some embodiments, said heterologous protein fused to said PTGFRN fragment additionally contains a signal sequence peptide. The signal sequence peptide can be a polypeptide of SEQ ID NO: 8.

Surface engineered exosomes can be produced from a cell transformed with a sequence encoding fragments of Basigin. In some embodiments, the fragments of Basigin lack one or more functional or structural domains, such as IgV. For example, the fragments of Basigin can comprise a polypeptide of SEQ ID NO: 10-12. In some embodiments, the fragments of Basigin are fused to one or more heterologous proteins. In some embodiments, the one or more heterologous proteins are fused to the N-terminus of said Basigin fragments. In some embodiments, the one or more heterologous proteins are fused to the C-terminus of said Basigin fragments. In some embodiments, the one or more heterologous proteins are fused to both the N-terminus and the C-terminus of said Basigin fragments. In some embodiments, the heterologous protein is a mammalian protein. In some embodiments, the heterologous protein is a human protein. In some embodiments, said heterologous protein fused to said Basigin fragment additionally contains a signal sequence peptide. The signal sequence peptide can be a polypeptide of SEQ ID NO: 13.

Surface engineered exosomes can be produced from a cell transformed with a sequence encoding fragments of IGSF8. In some embodiments, the fragments of IGSF8 lack one or more functional or structural domains, such as IgV. For example, the fragments of IGSF8 can comprise a polypeptide of SEQ ID NO: 15-18. In some embodiments, the fragments of IGSF8 are fused to one or more heterologous proteins. In some embodiments, the one or more heterologous proteins are fused to the N-terminus of said IGSF8 fragments. In some embodiments, the one or more heterologous proteins are fused to the C-terminus of said IGSF8 fragments. In some embodiments, the one or more heterologous proteins are fused to both the N-terminus and the C-terminus of said IGSF8 fragments. In some embodiments, the heterologous protein is a mammalian protein. In some embodiments, the heterologous protein is a human protein. In some embodiments, said heterologous protein fused to said IGSF8 fragment additionally contains a signal sequence peptide. The signal sequence peptide can be a polypeptide of SEQ ID NO: 19.

Surface engineered exosomes can be produced from a cell transformed with a sequence encoding fragments of IGSF2. In some embodiments, the fragments of IGSF2 lack one or more functional or structural domains, such as IgV. In some embodiments, the fragments of IGSF2 are fused to one or more heterologous proteins. In some embodiments, the one or more heterologous proteins are fused to the N-terminus of said IGSF2 fragments. In some embodiments, the one or more heterologous proteins are fused to the C-terminus of said IGSF2 fragments. In some embodiments, the one or more heterologous proteins are fused to both the N-terminus and the C-terminus of said IGSF2 fragments. In some embodiments, the heterologous protein is a mammalian protein. In some embodiments, the heterologous protein is a human protein. In some embodiments, said heterologous protein fused to said IGSF2 fragment additionally contains a signal sequence peptide. The signal sequence peptide can be a polypeptide of SEQ ID NO: 35.

In some embodiments surface-engineered exosomes comprise a polypeptide of a sequence identical or similar to a full-length or a fragment of a native exosome surface protein including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). In some embodiments, said peptide is 50% identical to a full-length or a fragment of a native exosome surface protein, e.g., 50% identical to SEQ ID NO: 1-34. In some embodiments, said polypeptide is 60% identical to a full-length or a fragment of a native exosome surface protein, e.g., 60% identical to SEQ ID NO: 1-34. In some embodiments, said polypeptide is 70% identical to a full-length or a fragment of a native exosome surface protein, e.g., 70% identical to SEQ ID NO: 1-34. In some embodiments, said polypeptide is 80% identical to a full-length or a fragment of a native exosome surface protein, e.g., 80% identical to SEQ ID NO: 1-34. In some embodiments, said polypeptide is 90% identical to a full-length or a fragment of a native exosome surface protein, e.g., 90% identical to SEQ ID NO: 1-34. In some embodiments, said polypeptide is 95% identical to a full-length or a fragment of a native exosome surface protein, e.g., 95% identical to SEQ ID NO: 1-34. In some embodiments, said polypeptide is 99% identical to a full-length or a fragment of a native exosome surface protein, e.g., 99% identical to SEQ ID NO: 1-34. In some embodiments, said polypeptide is 99.9% identical to a full-length or a fragment of a native exosome surface protein, e.g., 99.9% identical to SEQ ID NO: 1-34.

6.6. Affinity Purification

Some embodiments of the present invention relate to isolation, purification and sub-fractionation of exosomes using a specific binding interaction between a protein enriched on the exosome membrane and an immobilized binding agent. These methods generally comprise the steps of (1) applying or loading a sample comprising exosomes, (2) optionally washing away unbound sample components using appropriate buffers that maintain the binding interaction between the target proteins of exosomes and binding agents, and (3) eluting (dissociating and recovering) the exosomes from the immobilized binding agents by altering the buffer conditions so that the binding interaction no longer occurs.

Some embodiments relate to a method of removing exosomes from a sample using a specific binding interaction between a protein enriched on the exosome membrane and an immobilized binding agent. In the cases, exosomes bound to the binding agent are not eluted from the binding agent and a fraction which does not bind to the binding agent can be collected. The method can be used to purify a sample comprising exosomes and a non-exosomal material such as viruses (e.g., lentivirus, retrovirus, adeno-associated virus, or any other enveloped or non-enveloped virus) or a recombinant protein (e.g., antibodies, enzymes or other polypeptides), wherein the exosomes are contaminating particles. The bound exosomes can be retained bound to the binding agent and the non-exosomal material is collected, substantially free of exosomes.

The target protein, used for this isolation, purification, sub-fractionation or removal process, can be an endogenous protein produced from the genome of a producer cell, a protein introduced to the producer cell by a genetic modification, or a protein modified by chemical, physical or other biological methods. In some cases, the protein is a non-mutant protein or a mutant protein, e.g., a variant or a fragment of an endogenous protein. In some cases, the protein is a fusion protein.

Various binding agents having affinity to the target protein can be used for the embodiments of the present invention. For example, proteins, peptides, and small molecules with specific affinities to the target protein can be used as a binding agent. In some embodiments, binding agents are obtained from organic or inorganic sources. Examples of binding agents from organic sources include serum proteins, lectins or antibodies. Examples of binding agents from inorganic sources include boronic acids, metal chelates, and triazine dyes.

The binding agents can be chemically immobilized or coupled to a solid support so that exosomes having specific affinity to the binding agent become bound. Various forms of solid support can be used, e.g., a porous agarose bead, a microtiter plate, a magnetic bead, or a membrane. In some embodiments, the solid support forms a chromatography column and can be used for affinity chromatography of exosomes.

In some cases, isolation, purification, sub-fractionation and removal of exosomes are done by column chromatography using a column where the binding agents and the solid support are packed. In some embodiments, a sample containing exosomes run through the column to allow setting, a wash buffer run through the column, and the elution buffer subsequently applied to the column and collected. These steps can be done at ambient pressure or with application of additional pressure.

In some cases, isolation, purification, sub-fractionation and removal of exosomes are done using a batch treatment. For example, a sample is added to the binding agent attached to a solid support in a vessel, mixing, separating the solid support, removing the liquid phase, washing, centrifuging, adding the elution buffer, re-centrifuging and removing the elute.

In some cases, a hybrid method can be employed. For example, a sample is added to the binding agent attached to a solid support in a vessel, the solid support bound to the exosomes is subsequently packed onto a column, and washing and elution are done on the column.

In some cases, isolation, purification, sub-fractionation and removal of exosomes are done using a binding agent attached to microtiter plates, magnetic beads, or membranes. In the cases, a sample is added to the binding agent attached to a solid support, followed by the steps of mixing, separating the solid support, removing the liquid phase, washing, removing the washing buffer, adding the elution buffer, and removing the elute.

The binding between the binding agent and a target protein on the exosome is done in various physiological conditions optimal for specific interactions between the binding agent and the target protein on the exosome. Elution of the bound exosomes can be achieved by changing salt concentrations, pH, pI, charge and ionic strength directly or through a gradient.

In some embodiments, a sample isolated, purified or sub-fractionated with one binding agent is subsequently processed with a different binding agent.

In some embodiments, more than one columns are used in series, where each of the multiple columns contains a different binding agent specific to a different target protein.

In some embodiments, a single column contains multiple binding agents, each specific to a different target protein.

In some cases, the binding agent and solid support are reused by introduction of a periodic sanitization step. For example, they can be sanitized with a combination of propylene glycol, isopropanol, high ionic strength, and/or sodium hydroxide.

6.6.1. Sample Preparation

The methods described herein can be used to purify, isolate, sub-fractionate or remove exosomes from various samples comprising exosomes. In some embodiments, the sample is a clarified harvest material containing exosomes.

In some cases, the sample comprises exosomes partially purified by a purification method well known in the art. For example, ultrafiltration/diafiltration, hydroxyl apatite chromatography, hydrophobic interaction chromatography, deep filtration, or ion exchange bind/elute chromatography can be used to partially purify exosomes before applying to a binding agent for affinity purification.

In some cases, the partially purified material is further processed to have certain physiological conditions (e.g., pH, temperature, salt concentration, salt type, polarity) for desired interaction with the binding agent. A sample can be prepared by dilution or concentration to obtain certain exosome concentrations, or by adding excipients to change structure of exosomes. In some cases, the partially purified material is applied to the binding agent without any manipulation.

6.6.2. Binding

The methods described herein requires specific interaction between a target protein of an exosome and a binding agent. High-throughput screening can be performed to identify buffer conditions ideal for the specific binding—through altering salt concentration, pH, and/or reducing polarity with an organic modifier, ethylene glycol, propylene glycol, or urea. The interaction between a target protein and a binding agent can also change depending on sample conditions (e.g., sample amount loaded per volume of chromatographic resin, concentration of exosomes, concentration of impurities), loading buffers (e.g., pH, salt concentrations, salt types, polarity), and other physical conditions (e.g., temperature). Furthermore, adding excipients that alter the structure of the exosomes can also change their interactions. In addition, residence time can be adjusted based on differential adsorption rates between impurities and exosomes. Thus, various purification conditions described herein can be tested to identify ideal conditions for the step.

Similar approaches can be used to improve purity and yield, and aid in enriching, depleting, or isolating sub-populations of exosomes. These properties, along with maximizing load challenge and applying more stringent elution conditions, could be employed to further enhance the concentration of exosomes.

6.6.2.1. Elution

Elution of exosomes can be achieved through altering salt concentration, pH, and/or polarity with an organic modifier, ethylene glycol, propylene glycol, or urea.

Selective elution of exosomes can be achieved by increasing the concentration of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate sodium phosphate, ferrous chloride, calcium citrate, magnesium phosphate, and ferric chloride), or a combination thereof, in the elution buffer, through the use of an increasing gradient (step or linear) of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, at a fixed pH.

Substantial exosome purity can be achieved by flowing through impurities during the column loading phase, eluting impurities during selective excipient washes and selectively eluting product during elution while leaving additional impurities bound to the column. Absorbance measured from column eluates can indicate purify of exosomes obtained by the methods.

Elution can be also achieved by modulating the pH range, salts, organic solvents, small molecules, detergents, zwitterions, amino acids, polymers, temperature, and any combination of the above. Similar elution agents can be used to improve purity, improve yield, and isolate sub-populations of exosomes.

Elution can be also done with multiple elution buffers having different properties, such as pH, salts, organic solvents, small molecules, detergents, zwitterions, amino acids, polymers, temperature, and any combination of the above. A plurality of eluted fractions can be collected, wherein exosomes collected in each fraction has different properties. For example, exosomes collected in one fraction has a higher purity, a smaller or larger average size, a preferred composition, etc. than exosomes in other fractions.

Elution buffers with different properties can be applied as a continuous flow, while a plurality of eluted fractions are collected. Eluted fractions can be collected during isocratic elution or gradient elution. Once at least one eluted fraction is collected, a composition of the eluted fraction can be analyzed. For example, the concentration of exosomes, a host cell protein, a contaminant protein, DNA, carbohydrates, or lipids can be measured in each eluted fraction. Other properties of exosomes in each eluted fraction can be also measured. The properties include an average size, an average charge density, and other physiological properties related to bio-distribution, cellular uptake, half-life, pharmacodynamics, potency, dosing, immune response, loading efficiency, stability, or reactivity to other compounds.

6.6.2.2. Washing

Optionally, purity of exosomes can be further improved by washing samples prior to elution. In some embodiments, excipient can be a washing buffer. The excipient can be a solution having specific pH ranges, salts, organic solvents, small molecules, detergents, zwitterions, amino acids, polymers, and any combination of the above.

More specifically, the excipient can comprise arginine, lysine, glycine, histidine, calcium, sodium, lithium, potassium, iodide, magnesium, iron, zinc, manganese, urea, propylene glycol, aluminum, ammonium, guanidinium polyethylene glycol, EDTA, EGTA, a detergent, chloride, sulfate, carboxylic acids, sialic acids, phosphate, acetate, glycine, borate, formate, perchlorate, bromine, nitrate, dithiothreitol, beta mercaptoethanol, or tri-n-butyl phosphate.

The excipient can also comprise a detergent, selected from the group consisting of cetyl trimethylammonium chloride, octoxynol-9, TRITON™ X-100 (i.e., polyethylene glycol p-(1,1,3,3-tetramethylbutyl)-phenyl ether) and TRITON™ CG-110 available from Sigma-Aldrich; sodium dodecyl sulfate; sodium lauryl sulfate; deoxycholic acid; Polysorbate 80 (i.e., Polyoxyethylene (20) sorbitan monooleate); Polysorbate 20 (i.e., Polyoxyethylene (20) sorbitan monolaurate); alcohol ethoxylate; alkyl polyethylene glycol ether; decyl glucoside; octoglucosides; SafeCare; ECOSURF™ EH9, ECOSURF™ EH6, ECOSURF™ EH3, ECOSURF™ SA7, and ECOSURF™ SA9 available from DOW Chemical; LUTENSOL™ M5, LUTENSOL™ XL, LUTENSOL™ XP and APG™ 325 N available from BASF; TOMADOL™ 900 available from AIR PRODUCTS; NATSURF™ 265 available from CRODA; SAFECARE"1000 available from Bestchem, TERGITOL" L64 available from DOW; caprylic acid; CHEMBETAINE™ LEC available from Lubrizol; and Mackol DG.

6.6.3. Other Methods for Improving Outcome

The amount of exosomes that can be loaded per volume of chromatographic resin can be improved by modulating the feed material, for example, by increasing the concentration of exosomes, decreasing the concentration of impurities, altering the pH, decreasing the salt concentrations, decreasing the ionic strength, or altering the specific sub-populations of exosomes. Owing to mass transfer constraints and slow adsorption and desorption of exosomes on the resin, the amount of exosomes that can be loaded per volume of chromatographic resin can be increased by slowing the flow rate during column loading, employing longer columns to increase the residence time.

6.7. Applications

6.7.1. Purification of Exosomes

The use of exosomes for medical purposes requires that the exosomes be free or mostly free of impurities including but not limited to macromolecules, such as nucleic acids, contaminant proteins, lipids, carbohydrates, metabolites, small molecules, metals, or a combination thereof. The present invention provides a method of purifying exosomes from contaminating macromolecules. In some embodiments, purified exosomes are substantially free of contaminating macromolecules.

6.7.2. Sub-Fractionation of Exosomes

Embodiments of the present invention further provide methods for sub-fractionating populations of exosomes based on their membrane protein, size, charge density, ligand type (e.g., tetraspanins) and heparin or other sulfated carbohydrate binding sites. The choice of affinity tag, loading and elution buffer compositions and protocols can result in elution of different sub-populations of exosomes.

For example, embodiments of the present invention provide methods of purifying a population of exosomes with a smaller or larger size. The size of exosomes can be determined by methods available in the field. For example, the size can be measured by nanoparticle tracking analysis, multi-angle light scattering, single angle light scattering, size exclusion chromatography, analytical ultracentrifugation, field flow fractionation, laser diffraction, tunable resistive pulse sensing, or dynamic light scattering.

Embodiments of the present invention further relate to methods of sub-fractionating exosomes based on their charge density. The charge density of exosomes can be determined by potentiometric titration, anion exchange, cation exchange, isoelectric focusing, zeta potential, capillary electrophoresis, capillary zone electrophoresis, gel electrophoresis.

Embodiments of the present invention also relate to sub-fractionating exosomes based on other physiological properties, such as bio-distribution, cellular uptake, half-life, pharmacodynamics, potency, dosing, immune response, loading efficiency, stability, or reactivity to other compounds. The method enables isolation of a population of exosomes that are appropriate for a specific application.

6.8. Characterization of Exosomes

In some embodiments, the methods described herein further comprise the step of characterizing exosomes contained in each collected fraction. In some embodiments, contents of the exosomes can be extracted for study and characterization. In some embodiments, exosomes are isolated and characterized by metrics including, but not limited to, size, shape, morphology, or molecular compositions such as nucleic acids, proteins, metabolites, and lipids.

6.8.1. Measurement of the Contents of Exosomes

Exosomes can include proteins, peptides, RNA, DNA, and lipids. Total RNA can be extracted using acid-phenol: chloroform extraction. RNA can then be purified using a glass-fiber filter under conditions that recover small-RNA containing total RNA, or that separate small RNA species less than 200 nucleotides in length from longer RNA species such as mRNA. Because the RNA is eluted in a small volume, no alcohol precipitation step may be required for isolation of the RNA.

Exome compositions may be assessed by methods known in the art including, but not limited to, transcriptomics, sequencing, proteomics, mass spectrometry, or HP-LC.

The composition of nucleotides associated with isolated exosomes (including RNAs and DNAs) can be measured using a variety of techniques that are well known to those of skill in the art (e.g., quantitative or semi-quantitative RT-PCR, Northern blot analysis, solution hybridization detection). In a particular embodiment, the level of at least one RNA is measured by reverse transcribing RNA from the exosome composition to provide a set of target oligodeoxynucleotides, hybridizing the target oligodeoxynucleotides to one or more RNA-specific probe oligonucleotides (e.g., a microarray that comprises RNA-specific probe oligonucleotides) to provide a hybridization profile for the exosome composition, and comparing the exosome composition hybridization profile to a hybridization profile generated from a control sample. An alteration in the signal of at least one RNA in the test sample relative to the control sample is indicative of the RNA composition.

Also, a microarray can be prepared from gene-specific oligonucleotide probes generated from known RNA sequences. The array can contain two different oligonucleotide probes for each RNA, one containing the active, mature sequence and the other being specific for the precursor of the RNA (for example miRNA and pre-miRNAs). The array can also contain controls, such as one or more mouse sequences differing from human orthologs by only a few bases, which can serve as controls for hybridization stringency conditions. tRNAs and other RNAs (e.g., rRNAs, mRNAs) from both species can also be printed on the microchip, providing an internal, relatively stable, positive control for specific hybridization. One or more appropriate controls for non-specific hybridization can also be included on the microchip. For this purpose, sequences are selected based upon the absence of any homology with any known RNAs.

The microarray can be fabricated using techniques known in the art. For example, probe oligonucleotides of an appropriate length, e.g., 40 nucleotides, are 5'-amine modified at position C6 and printed on activated slides using commercially available microarray systems, e.g., the GeneMachine OmniGrid.™ 100 Microarrayer and Amersham CodeLink.™ Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6.times. SSPE/30% formamide at 25° C. for 18 hours, followed by washing in 0.75.times. TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary RNAs, in the exosome preparation. According to one embodiment, the labeled cDNA oligomer is a biotin-labeled cDNA, prepared from a biotin-labeled primer. The microarray is then processed by direct detection of the biotin containing transcripts using, e.g., Streptavidin-Alexa647 conjugate, and scanned utilizing conventional scanning methods. Image intensities of each spot on the array are proportional to the abundance of the corresponding RNA in the exosome.

Data mining work is completed by bioinformatics, including scanning chips, signal acquisition, image processing, normalization, statistic treatment and data comparison as well as pathway analysis. As such, microarray can profile hundreds and thousands of polynucleotides simultaneously with high throughput performance. Microarray profiling analysis of mRNA expression has successfully provided valuable data for gene expression studies in basic research. And the technique has been further put into practice in the pharmaceutical industry and in clinical diagnosis. With increasing amounts of miRNA data becoming available, and with accumulating evidence of the importance of miRNA in gene regulation, microarray becomes a useful technique for high through-put miRNA studies. The analysis of miRNA levels utilizing polynucleotide probes can be carried out in a variety of physical formats as well. For example, the use of microtiter plates or automation can be used to facilitate the processing of large numbers of test samples.

6.8.2. Measurement of the Size of Exosomes

In some embodiments, the methods described herein comprise measuring the size of exosomes and/or populations of exosomes included in the purified fractions. In some embodiments, exosome size is measured as the longest measurable dimension. Generally, the longest general dimension of an exosome is also referred to as its diameter.

Exosome size can be measured using various methods known in the art, for example, nanoparticle tracking analysis, multi-angle light scattering, single angle light scattering, size exclusion chromatography, analytical ultracentrifugation, field flow fractionation, laser diffraction, tunable resistive pulse sensing, or dynamic light scattering.

Exosome size can be measured using dynamic light scattering (DLS) and/or multiangle light scattering (MALS). Methods of using DLS and/or MALS to measure the size of exosomes are known to those of skill in the art, and include the nanoparticle tracking assay (NTA, e.g., using a Malvern Nanosight NS300 nanoparticle tracking device). In a specific embodiment, the exosome size is determined using a Malvern NanoSight NS300. In some embodiments, the exosomes described herein have a longest dimension of about 20-1000 nm as measured by NTA (e.g., using a Malvern NanosightNS300). In other embodiments, the exosomes described herein have a longest dimension of about 40-1000 nm as measured by NTA (e.g., using a Malvern NanosightNS300). In other embodiments, the exosome populations described herein comprise a population, wherein 90% of said exosomes have a longest dimension of about 20-1000 nm as measured by NTA (e.g., using a Malvern Nanosight NS300). In other embodiments, the exosome populations described herein comprise a population, wherein 95% of said exosomes have a longest dimension of about 20-1000 nm as measured by NTA (e.g., using a Malvern Nanosight NS300). In other embodiments, the exosome populations described herein comprise a population, wherein 99% of said exosomes have a longest dimension of about 20-1000 nm as measured by NTA (e.g., using a Malvern Nanosight NS300). In other embodiments, the exosome populations described herein comprise a population, wherein 90% of said exosomes have a longest dimension of about 40-1000 nm as measured by NTA (e.g., using a Malvern Nanosight NS300). In other embodiments, the exosome populations described herein comprise a population, wherein 95% of said exosomes have a longest dimension of about 40-1000 nm as measured by NTA (e.g., using a Malvern Nanosight NS300). In other embodiments, the exosome populations described herein comprise a population, wherein 99% of said exosomes have a longest dimension of about 40-1000 nm as measured by NTA (e.g., using a Malvern Nanosight NS300).

Exosome size can be measured using tunable resistive pulse sensing (TRPS). In a specific embodiment, exosome size as measured by TRPS is determined using an iZON qNANO Gold. In some embodiments, the exosomes described herein have a longest dimension of about 20-1000 nm as measured by TRPS (e.g., using an iZON qNano Gold). In other embodiments, the exosomes described herein have a longest dimension of about 40-1000 nm as measured by TRPS (e.g., an iZON qNano Gold). In other embodiments, the exosome populations described herein comprise a population, wherein 90% of said exosomes have a longest dimension of about 20-1000 nm as measured by TRPS (e.g., using an iZON qNano Gold). In other embodiments, the exosome populations described herein comprise a population, wherein 95% of said exosomes have a longest dimension of about 20-1000 nm as measured by TRPS (e.g., using an iZON qNano Gold). In other embodiments, the exosome populations described herein comprise a population, wherein 99% of said exosomes have a longest dimension of about 20-1000 nm as measured by TRPS (e.g., using an iZON qNano Gold). In other embodiments, the exosome populations described herein comprise a population, wherein 90% of said exosomes have a longest dimension of about 40-1000 nm as measured by TRPS (e.g., using an iZON qNano Gold). In other embodiments, the exosome populations described herein comprise a population, wherein 95% of said exosomes have a longest dimension of about 40-1000 nm as measured by TRPS (e.g., using an iZON qNano Gold). In other embodiments, the exosome populations described herein comprise a population, wherein 99% of said exosomes have a longest dimension of about 40-1000 nm as measured by TRPS (e.g., using an iZON qNano Gold).

Exosome size can be measured using electron microscopy. In some embodiments, the method of electron microscopy used to measure exosome size is transmission electron microscopy. In a specific embodiment, the transmission electron microscope used to measure exosome size is a Tecnai™ G2 Spirit BioTWIN. Methods of measuring exosome size using an electron microscope are well-known to those of skill in the art, and any such method can be appropriate for measuring exosome size. In some embodiments, the exosomes described herein have a longest dimension of about 20-1000 nm as measured by a scanning electron microscope (e.g., a Tecnai™ G2 Spirit BioTWIN scanning electron microscope). In other embodiments, the exosomes described herein have a longest dimension of about 40-1000 nm as measured by a scanning electron microscope (e.g., a Tecnai™ G2 Spirit BioTWIN scanning electron microscope). In other embodiments, the exosome populations described herein comprise a population, wherein 90% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population, wherein 95% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population, wherein 99% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population wherein 90% of said exosomes have a longest dimension of about 40-1000 nm as measured by a scanning electron microscope (e.g., a Tecnai™ G2 Spirit BioTWIN scanning electron microscope). In other embodiments, the exosome populations described herein comprise a population wherein 95% of said exosomes have a longest dimension of about 40-1000 nm as measured by a scanning electron microscope (e.g., a Tecnai™ G2 Spirit BioTWIN scanning electron microscope). In other embodiments, the exosome populations described herein comprise a population wherein 99% of said exosomes have a longest dimension of about 40-1000 nm as measured by a scanning electron microscope (e.g., a Tecnai™ G2 Spirit BioTWIN scanning electron microscope).

6.8.3. Measurement of the Charge Density of Exosomes

In some embodiments, the methods described herein comprise measuring the charge density of exosomes and/or populations of exosomes included in the purified fractions. In some embodiments, the charge density is measured by potentiometric titration, anion exchange, cation exchange, isoelectric focusing, zeta potential, capillary electrophoresis, capillary zone electrophoresis, or gel electrophoresis.

6.8.4. Measurement of Density of Exosome Proteins

In some embodiments, the methods described herein comprise measuring the density of exosome proteins on the exosome surface. The surface density can be calculated or presented as the mass per unit area, the number of proteins per area, number of molecules or intensity of molecule signal per exosome, molar amount of the protein, etc. The surface density can be experimentally measured by methods known in the art, for example, by using bio-layer interferometry (BLI), FACS, Western blotting, fluorescence (e.g., GFP-fusion protein) detection, nano-flow cytometry, ELISA, alphaLISA, and/or densitometry by measuring bands on a protein gel.

6.9. Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); AL. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pa.: Mack Publishing Company, 2005); Carey and Sundberg Advanced Organic Chemistry 3rd Ed. (Plenum Press) Vols A and B (1992).

6.9.1. Example 1: Identification of Exosome Proteins

6.9.1.1. Collection of Exosomes

Exosomes were collected from the supernatant of high density suspension cultures of HEK293 SF cells after 9 days. The supernatant was filtered and fractionated by anion exchange chromatography and eluted in a step gradient of sodium chloride. The peak fraction with the highest protein concentration contained exosomes and contaminating cellular components. The peak fraction was isolated and further fractionated on an Optiprep™ (60% iodixanol w/v) density gradient by ultracentrifugation.

The exosome fraction was concentrated by ultracentrifugation in a 38.5 mL Ultra-Clear (344058) tube for a SW 32 Ti rotor at 133,900×g for 3 hours at 4° C. The pelleted material was resuspended in 1 mL PBS and 3 mL of Optiprep™, bringing the final iodixanol concentration to 45%. For the Optiprep™ gradient, a 4-tier sterile gradient was prepared with 4 mL of 45% iodixanol containing the resuspended material, 3 mL 30% iodixanol, 2 mL 22.5% iodixanol, 2 mL 17.5% iodixanol, and 1 mL PBS in a 12 mL Ultra-Clear (344059) tube for a SW 41 Ti rotor. The Optiprep™ gradient was ultracentrifuged at 150,000×g for 16 hours at 4° C. to separate the exosome fraction. Ultracentrifugation resulted in a Top Fraction known to contain exosomes, a Middle Fraction containing cell debris of moderate density, and a Bottom Fraction containing high density aggregates and cellular debris (FIG. 1). The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 µL) and stored at 4° C.

6.9.1.2. Sample Preparation for LC-MS/MS Analysis

To determine proteins specific to exosomes, the Top Fraction and Bottom Fraction of the Optiprep™ gradient were analyzed by liquid chromatography-tandem mass spectrometry. All samples were received in either phosphate-buffered saline (PBS) buffer or PBS and 5% sucrose. Prior to analysis, the total protein concentration of each sample was determined by bicinchoninic acid (BCA) assay, after which each sample was appropriately diluted to 125 µg/mL in PBS buffer. Next, 50.0 µL of each sample was added to a separate 1.5 mL microcentrifuge tube containing an equal volume of exosome lysis buffer (60 mM Tris, 400 mM GdmCl, 100 mM EDTA, 20 mM TCEP, 1.0% Triton X-100) followed by the transfer of 2.0 µL 1.0% Triton X-100 solution. All samples were then incubated at 55° C. for 60 minutes.

Protein precipitation was performed by adding 1250 µL of ethanol at −20° C. To improve efficiency, samples were vigorously vortexed for approximately 10 minutes and then incubated at −20° C. for 60 minutes. After incubation, samples were sonicated in a water bath for 5 minutes. Precipitated material was pelleted by centrifuging for 5 minutes at 15,000 g at 4° C. The supernatant was decanted, and the pelleted material was thoroughly dried using nitrogen gas. Pellets were resuspended in 30.0 µL digestion buffer (30 mM Tris, 1.0 M GdmCl, 100 mM EDTA, 50 mM TCEP, pH 8.5) which also reduced disulfide bonds. Free cysteine residues were alkylated by adding 5.0 µL alkylation solution (375 mM iodoacetamide, 50 mM Tris, pH 8.5) and incubating the resulting solution at room temperature in the dark for at least 30 minutes.

After incubation, each sample was diluted using 30.0 µL 50 mM Tris pH 8.5, and proteolytic digestion was initiated by adding 2.0 µg trypsin. All samples were mixed and then incubated overnight at 37° C. After the incubation, trypsin activity was ceased by adding 5.0 µL 10% formic acid. Prior to analysis by LC-MS/MS, each sample was desalted using Pierce C18 spin columns. At the end of this process, each sample was dried down and reconstituted in 50.0 µL of water with 0.1% formic acid and transferred to an HPLC vial for analysis.

6.9.1.3. LC-MS/MS Analysis

Samples were injected into an UltiMate 3000 RSCLnano (Thermo Fisher Scientific) low flow chromatography system, and tryptic peptides were loaded onto an Acclaim PepMap 100 C18 trapping column (75 µm×2 cm, 3 µm particle size, 100 Å pore size, Thermo Fisher Scientific) using loading mobile phase (MPL: water, 0.1% formic acid) at a flowrate of 1.000 µL/min. Peptides were eluted and separated with a gradient of mobile phase A (MPA: water, 0.1% formic acid) and mobile phase B (MPB: acetonitrile, 0.1% formic acid) at a flowrate of 300 nL/min across an EASY-Spray C18 analytical column (75 µm×25 cm, 2 µm particle size, 100 Å pore size, Thermo Fisher Scientific). The stepwise gradient used for elution began at 2% MPB, where it was held for 8 minutes during loading. The percentage MPB then increased from 2-17% over 35 minutes, again from 17-25% over 45 minutes, and finally from 25-40% over 10 minutes. The most hydrophobic species were removed by increasing to 98% MPB over 5 minutes, then holding there for 10 minutes. The total runtime for the method was 135 minutes and allowed sufficient time for column re-equilibration. Wash cycles were performed in between non-identical analytical injections to minimize carry-over.

Mass analyses were performed with a Q Exactive Basic (Thermo Fisher Scientific) mass spectrometer. Precursor ion mass spectra were measured across an m/z range of 400-1600 Da at a resolution of 70,000. The 10 most intense precursor ions were selected and fragmented in the HCD cell using a collision energy of 27, and MS/MS spectra were measured across an m/z range of 200-2000 Da at a resolution of 35,000. Ions with charge states from 2-4 were selected for fragmentation and the dynamic exclusion time was set to 30 seconds. An exclusion list containing 14 common polysiloxanes was utilized to minimize misidentification of known contaminants.

6.9.1.4. Data Processing

Proteins were first identified and quantified (label-free) using Proteome Discoverer software (version 2.1.1.21, Thermo Fisher Scientific) and the Sequest HT algorithm combined with the Target Decoy PSM Validator. Searches were performed against the full Swiss-Prot *Homo sapiens* (taxonomy 9606 version 2017-05-10: 42,153 entries) reference database, as well as a custom Uniprot database containing Ela proteins (7 entries). The following search parameters were used: enzyme, trypsin; maximum of 2 missed cleavages; minimum peptide length of 6 residues; 10 ppm precursor mass tolerance; and 0.02 Da fragment mass tolerance. The search also included specific dynamic modifications (oxidation of M; deamidation of N or Q; phosphorylation of S, T, or Y; pyro-glutamation of peptide-terminal E; and acetylation of protein N terminus) and static modifications (carbamidomethylation of C).

In the Target Decoy PSM Validator, the maximum delta Cn and both strict and relaxed target false discovery rates (FDRs) were set to 1 because the data were searched again using Scaffold software (version 4.8.2, Proteome Software Inc.). In Scaffold, the data were also searched using the X! Tandem open source algorithm to identify proteins using a protein threshold of 99.0%, a minimum of 2 peptides, and a peptide threshold of 95%.

To determine the identity of novel exosome-specific proteins, total peptide spectral matches (PSMs) were compared for proteins found in the top exosome fraction of the Optiprep™ gradient versus those in the lower fraction. As shown in FIG. 2, there was weak correlation between the top-fraction proteins (Y-axis) and the bottom-fraction proteins (X-axis). Proteins plotted above the dotted line represent exosome-enriched proteins, while those below the dotted line represent contaminant-enriched proteins. Importantly, there were a number of membrane-associated proteins identified that were highly enriched in the exosomes fraction, including (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), and (8) a class of ATP transporter proteins (ATP1A1, ATP1A2, ATP1A3, ATP1A4, ATP1B3, ATP2B1, ATP2B2, ATP2B3, ATP2B4). As shown in the tryptic peptide coverage maps in FIGS. 3-5, the mass spectrometry study resulted in broad coverage of PTGFRN (FIG. 3), IGSF8 (FIG. 4), and Basigin (FIG. 5). Together, these results demonstrate that there are numerous transmembrane proteins enriched in purified exosome populations that may be useful for purifying exosomes from heterogeneous populations or for use as scaffolds in generating engineered exosomes.

6.9.2. Example 2: Verification of Surface Protein Expression

To confirm that the exosome-specific proteins identified in the mass spectrometry studies were highly enriched on the surface of exosomes, protein blotting was carried out on total cell lysate and purified exosome populations from HEK293 cells. As shown in FIG. 6A, the total protein pattern differed substantially between total cell lysate (left) and exosome lysate (right). Specifically, there was a strong band at ~110 kDa in the exosome lysate that was absent in the total cell lysate. Western blotting for PTGFRN revealed a band at the expected size of ~110 kDa in the exosome lysate but not in the cell lysate (FIG. 6B), indicating that PTGFRN is highly enriched in exosomes, and may be visually detectable in total exosome lysate.

The mass spectrometry studies indicated the presence of several novel exosome-associated membrane proteins. To further confirm this association, exosome fractions were purified on self-forming Optiprep™ gradients and analyzed by Western blotting. As shown in FIG. 7A, total protein is detected in all fractions of the gradient and the exosome marker proteins Alix and Syntenin are enriched in fractions 2-6. Importantly, each of the novel surface marker proteins analyzed were enriched in these same fractions, indicating a strong and specific association with exosomes (FIG. 7B). The demonstration that these transmembrane proteins are highly expressed and enriched on exosomes provides an opportunity for purifying exosomes by using a binding agent directed against any of these proteins, as well as generating high expression surface-modified exosomes containing heterologous proteins fused to any of these novel proteins (FIG. 8).

6.9.3. Example 3: Domain Characterization of PTGFRN

PTGFRN, BSG, IGSF3, and IGSF8 are all type I single-pass transmembrane proteins with an N-terminus facing the extracellular/extravesicular environment and a C-terminus located in the cytoplasm/exosome lumen and contain at least two immunoglobulin V (IgV) repeats, as illustrated in FIG. 8. PTGFRN was the most highly enriched surface protein detected in the mass spectrometry analysis shown in FIG. 2. Expression constructs encoding fusion proteins between GFP and full length PTGFRN or various IgV truncation mutants of PTGFRN described in FIGS. 9A and B were stably expressed in HEK293 cells. Exosomes were isolated from the HEK293 cell culture using the method described in Example 1 and analyzed by Western blotting using an anti-GFP antibody. As shown in FIG. 9B, expression of the fusion proteins between GFP and full-length or truncated PTGFRN were detected in the purified exosomes. Interestingly, deletion of the first IgV domain resulted in a lower molecular weight band (marked as "cleaved product") that was not detectable with overexpression of the full-length protein. This smaller product was consistently detected in all truncation mutants, suggesting that it was generated as a result of protease cleavage. The exosomes containing various GFP-PTGFRN fusion proteins were analyzed on an SDS-PAGE mini-PROTEAN® TGX Stain-Free Gel (Bio-Rad, Inc.) to measure total exosome protein. The result is provided in FIG. 10. Expression of the fusion protein of GFP and full-length PTGFRN was easily detectable and very abundant, at a level as high as ~50% of the total proteins in the purified exosomes (lane 2). The lower molecular weight cleavage product (marked as "cleaved product") was not clearly visible and thus was absent in the native exosomes or exosomes over-expressing full length PTGFRN (lanes 1 and 2), suggesting that the first IgV domain (IgV 1) at the N-terminus of the protein may prevent the cleavage of PTGFRN.

Full-length PTGFRN and various truncated PTGFRN mutants were then stably expressed with an N-terminal FLAG tag in HEK293 cells (FIG. 11A). Exosomes from the cell culture were collected and analyzed by Western blotting with an anti-FLAG antibody. The result is provided in FIG. 11B. In contrast to the fusion proteins containing GFP in their C-terminus (FIGS. 9 and 10), fusion proteins containing a FLAG tag in the N-terminus did not yield a low molecular weight band (marked as "no cleavage product" in FIG. 11B), and the shorter truncations were detected at a low level. This result suggests that the cleavage event is likely removing the N-terminus of the protein linked to the FLAG epitope used for Western blotting (FIG. 11B).

PTGFRN is poorly detected in cell lysate and a mixture of intact and cleaved PTGFRN is detected in purified exosomes as suggested by the Western blot result provided in FIGS. 6A and B. This suggests that PTGFRN is being cleaved while being localized and integrated in the exosome membrane or during formation of exosomes. ADAM10 (A Disintegrin And Metalloproteinase Domain 10) is a conventional exosome protein and a membrane-associated metalloprotease. HEK293 cells were transfected with Cas9 and four guide RNAs targeting the ADAM10 locus (CRISPR32174_SG, CRISPR726928_SG, CRISPR726931_SG, and CRISPR726933_SG, Thermo Fisher Scientific) to generate ADAM10 knockout cells. ADAM10 knockout cells (ADAM 10−) or wild type cells (ADAM10+) were then stably transfected with either a construct encoding a fusion protein containing full-length PTGFRN fused to GFP or a different fusion protein containing truncated PTGFRN lacking the first three IgV domains fused to GFP (PTGFRN_IgV3-GFP). Exosomes were isolated from these cells and expression of the fusion proteins was measured by total protein PAGE and Western blotting using an anti-GFP antibody. FIG. 12A shows that comparable amounts of total proteins were loaded on each lane. Western blotting using an anti-ADAM10 antibody (ab124695; Abcam) showed efficient deletion of ADAM 10 in the knockout cells (FIG. 12B). Western blotting using an anti-GFP antibody showed high level expression of fusion proteins containing full length PTGFRN and GFP in both wild type (ADAM10+) and ADAM10 knockout cells (ADAM10−) as provided in FIG. 12C (lanes 1 and 2). This result is consistent with the result in FIG. 9B where no cleavage of fusion proteins containing the full length PTGFRN was detected. Interestingly, the cleavage product previously detected for PTGFRN_IgV3-GFP was detected in the wild type cells but was absent in the ADAM10 knockout cells (FIG. 12C, lanes 3 and 4). This suggests that ADAM10 mediates the cleavage of exosomal PTGFRN fragments. This result also suggests that a fusion protein containing truncated PTGFRN fragments would be more successfully expressed on exosomes from cells that lack ADAM10 (ADAM10−).

PTGFRN can be used as an attractive fusion partner for high-density exosome decoration/loading, but because of its size (~100 kDa) a smaller truncated version would be preferred to allow co-expression of large, biologically active molecules. The ADAM10-dependent cleavage detected in each of the IgV truncation mutants presents an issue for high-density loading because a certain percentage of any fusion protein would be cleaved from the exosome surface, reducing the degree of loading/display. To identify a minimal PTGFRN fragment that facilitates high density exosome surface display without suffering from protease cleavage, PTGFRN lacking five of the six IgV domains (PTGFRN_IgV6) was expressed as a fusion to a FLAG tag and a fusion partner protein (FIG. 13). Expression of fusion proteins containing PTGFRN_IgV6 yielded the predicted cleavage product identified previously (FIG. 14B, #451). Serial truncation mutants of PTGFRN_IgV6 lacking four additional amino acids at a time were also tested, and removal of 12 amino acids yielded exosomes that did not undergo cleavage of PTGFRN (FIG. 14A, FIG. 14B, #454). The PTGFRN #454 is a polypeptide of SEQ ID NO: 33. Additionally, because the FLAG tag is N-terminal to the cleavage site, shorter truncations of PTGFRN_IgV6 resulted in higher expression of the fusion protein, suggesting that cleavage is not occurring with these truncations (FIG. 14C).

The results provided in FIG. 15 further suggest that full-length PTGFRN (FL) and PTGFRN_454 (sIgV) would be ideal fusion partners for high-density expression of luminal (C-terminal fusions) or surface (N-terminal) proteins on and/or in exosomes. To test this hypothesis, several scaffold proteins were tested for their ability to produce high-density display exosomes. Fusion proteins comprising a scaffold protein and GFP were expressed in the cell culture, specifically fusion proteins containing GFP fused to the luminal side of the frequently used pDisplay scaffold (PDGF receptor), PalmPalm (palmitoylation sequence), CD81, or either full length PTGFRN (FL) or PTGFRN_454 (sIgV). A dose titration of exosomes purified from the cells stably expressing each fusion protein demonstrated that the PTGFRN fusion proteins resulted in much greater GFP fluorescence than any other scaffold, including the well-known exosome protein CD81. Compared to the pDisplay scaffold, full-length PTGFRN and sIgV resulted in >25-fold enhancement in loading efficiency (FIG. 15). These results suggest that use of the full-length PTGFRN or the truncated PTGFRN (sIgV) which is short enough to remove the cleavage site, as a fusion partner allows for high-density display or exosome loading.

6.9.4. Example 4: IGSF8 Overexpression does not Lead to High Density Exosome Display The expression level of PTGFRN suggests that it would be an ideal fusion partner for producing engineered exosomes. To determine if other members of the immunoglobulin-containing protein family would be suitable for exosome engineering, HEK293 cells were stably transfected with an IGFS8-GFP fusion protein and the resulting exosomes were purified (FIG. 16A). Native exosomes and IGSF8-GFP exosomes were analyzed on an SDS-PAGE mini-PROTEAN® TGX Stain-Free Gel (Bio-Rad, Inc.), which uses a tryptophan-binding dye to detect proteins, as provided in FIG. 16B. IGSF8 contains 10 tryptophan residues, allowing for its easy detection. Western blotting using an anti-GFP antibody confirmed expression of IGSF8-GFP on the overexpressing exosomes (FIG. 16B, bottom). Interestingly, when the IGSF8-GFP exosomes were tested for GFP fluorescence compared to GFP fusions to the pDisplay scaffold (PDGF receptor), CD81, or either full length PTGFRN (FL) or PTGFRN_454 (sIgV), IGSF8 (FL IGSF8) failed to show GFP enrichment over low-level stochastic display observed with pDisplay (FIG. 17). This result suggests that not every IgV family member can be used as a fusion protein for engineering high-density exosome surface display/luminal loading, and that PTGFRN and other family members are superior to IGSF8 in this respect. IGSF8 expression, however, was detected at high levels on the surface of unmodified exosomes, which would permit IGSF8 to be used as a target for exosome affinity purification.

6.9.5. Example 5: Expression and Characterization of the Extracellular Domain of PTGFRN in Mammalian Cells The extracellular domain (ECD) of PTGFRN is 98 kDa and contains six tandem IgV repeats. The ECD of PTGFRN may be a desirable target for exosome affinity purification reagents due to its size and high expression levels. To characterize this segment of PTGFRN, the PTGFRN ECD was expressed as a fusion protein with the endogenous signal peptide at the N-terminus (SP), and a PAR1 cleavage site and Fc domain at the C-terminus (FIG. 18). PAR1 is a substrate for thrombin and can be used to elute Fc fusion proteins using Protein A resin. PTGFRN has nine predicted N-linked glycosylation sites and 6 predicted disulfide bonds, which preclude the use of bacterial expression systems for the production of endogenous glycoproteins. The PTGFRN ECD was overexpressed using the Expi293 Expression System (Thermo Fisher Scientific), which is used to produce high yield mammalian recombinant proteins. Conditioned cell culture media from transfected Expi293 cells was 0.2 μm filtered and purified on Protein A followed by low pH glycine elution and immediate neutralization. The Fc tag was removed with thrombin treatment and the cleaved protein pool was re-run over Protein A. The flow-through was collected, concentrated, and polished on preparative SEC. The purified PTGFRN ECD was analyzed by gel filtration chromatography in PBS pH 7.4 using a Superdex 200 column (GE Healthcare) and detected at 280 nm UV fluorescence. FIG. 19A shows a single elution peak at ~55 mL and FIG. 19B shows a single protein product at the predicted size of PTGFRN ECD when the eluate peak was analyzed on a denaturing SDS-PAGE mini-PROTEAN® TGX Stain-Free Gel (Bio-Rad, Inc.), indicating PTGFRN ECD can be purified from mammalian cells.

To confirm proper expression of the PTGFRN ECD, the purified protein was analyzed by size exclusion chromatography/multiangle light scattering (SEC-MALS), using BSA and an anti-VLA4 antibody as standards for comparison. Recombinant PTGFRN ECD was eluted at ~2× its predicted molecular weight (198 kDa as opposed to the predicted molecular weight, 98 kDa; FIG. 20A). To determine whether PTGFRN ECD forms a homodimer in solution, recombinant PTGFRN ECD was run over an analytical SEC column (Tosoh, 7.8×30 cm, G3000SW xl) in PBS in the absence of guanidium chloride (GuHCl) or in the presence of 1M or 2M guanidinium chloride (GuHCl). FIG. 20B shows the elution profile of the PTGFRN ECD under increasing GuHCl (no GuHCl (a curve labeled "PTGFRN"), 1M GuHCl (a curve labeled "PTGFRN+1M GuHCl"), or 2M GuHCl (a curve labeled "PTGFRN+2M GuHCl")) and the conversion of the predicted dimeric peak to a monomeric peak. These results suggest that PTGFRN ECD forms a homodimer, and that PTGFRN dimerization may naturally occur on the exosome surface.

6.9.6. Example 6: PTGFRN Protein Array

PTGFRN is poorly characterized in the literature, and its role as an exosomal protein is largely unexplored. PTGFRN is also known as CD9 Partner 1 (CD9P-1) due to its interaction with CD9, which is also found on the surface of exosomes. To further understand which proteins PTGFRN binds to, recombinant mono-biotinylated human PTGFRN ECD was generated and probed on a protein microarray containing over 20,000 proteins encompassing 81% of the human proteome (CDI Laboratories). Binding analysis was performed at pH 5.6 and 7.4 to represent the pH of the acidifying endosome and the cytosol, respectively. Nine positive hits were identified at pH 7.4, and 16 were identified at pH 5.6. Three proteins (LGALS1, galectin-1; FCN1, ficolin-1; MGAT4B, alpha-1,3-mannosyl-glycoprotein 4-beta-N-acetylglucosaminyltransferase B) were identified at both pH 5.6 and pH 7.4 (FIG. 21). LGALS1 is known to bind to monomeric carbohydrates and complex glycans but has not been implicated as a PTGFRN binding partner. To confirm the interaction between PTGFRN and LGALS1, biotinylated recombinant PTGFRN ECD was bound to a Streptavidin optical probe and analyzed by bio-layer interferometry (BLI) using an Octet® RED96 (Pall). Dose-dependent binding of galectin-1 to PTGFRN was confirmed by BLI (FIG. 22). The interaction between LGALS1 and PTGFRN was reversible and competed by lactose in a dose-dependent manner (FIG. 23), demonstrating the specificity of this interaction. These results also suggest that exosomes may be purified by using PTGFRN binding partners as affinity reagents.

6.9.7. Example 7: Binding of Anti-PTGFRN Antibody to PTGFRN or Exosomes

Biotinylated PTGFRN was bound to a Streptavidin probe of an Octet® RED96 (Pall) and incubated in PBS+0.1% Tween 20 with increasing concentrations of a monoclonal rat antibody against CD315, an alias for PTGFRN (MABT883, Millipore Sigma). Dose-dependent binding was detected suggesting specific recognition of PTGFRN by the antibody (FIG. 24). To determine whether the anti-CD315 antibody could bind to exosomes, the anti-CD315 antibody was bound to a Protein L probe and incubated with increasing amounts of Optiprep™ purified HEK293 exosomes (FIG. 25). As shown in FIG. 25, the dose-dependent deflection after incubation with purified exosomes shows that the anti-CD315 antibody can recognize endogenous PTGFRN on the exosome surface. A similar experiment was performed with HEK293 cells stably transfected with full length PTGFRN to generate PTGFRN overexpressing exosomes (PTGFRN++ exosomes). The overexpressing exosomes were incubated with the immobilized anti-CD315 antibody and resulted in a dose-dependent deflection indicating specific binding between the antibody and exosomes (FIG. 26). To compare the extent of antibody binding to native or PTGFRN overexpressing exosomes, 1.1E11 exosomes of each variety were incubated in the presence of the anti-CD315 antibody and measured by BLI. As shown in FIG. 27, the PTGFRN overexpressing exosomes led to a much greater deflection than the native exosomes, indicating that increased levels of PTGFRN leads to greater binding, and that PTGFRN binding can therefore be used for exosome purification.

6.9.8. Example 8: Domain Recognition by Anti-PTGFRN Antibodies

The results in Examples 6 and 7 suggest that exosomes may be purified based on affinity interactions with PTGFRN. Full length PTGFRN and a series of truncation mutants were expressed as mono-biotinylated recombinant proteins using the Expi293 system described above (FIG. 28, left). Each of the truncations was incubated with the anti-CD315 antibody and binding was measured by BLI. Only full length PTGFRN bound the anti-CD315 antibody, indicating that the epitope is at the N-terminus of the protein in the first IgV domain.

Polyclonal antibody pools were generated by injecting rabbits with recombinant full-length ecto-domain of PTGFRN similar to construct 1 in FIG. 28 but lacking a biotinylation sequence. Polyclonal antibody pools were purified from terminal bleeds by Protein A and tested for reactivity against PTGFRN truncation fragments. Each of the fragments was analyzed on a denaturing SDS-PAGE mini-PROTEAN® TGX Stain-Free Gel (Bio-Rad, Inc.) confirming expression of correct length proteins (FIG. 29A). Western blotting was then carried out on the samples using the pooled polyclonal rabbit antibodies, and correct sized bands were detected in each lane as well as for control native exosomes, confirming specific reactivity with polyclonal PTGFRN antibodies (FIG. 29B). To confirm this result, each of the biotinylated PTGFRN fragments was analyzed by BLI and the results are provided in FIG. 30. Incubation with the polyclonal antibody pools showed binding in all conditions, demonstrating broad reactivity with the antibodies for each of the IgV domain of PTGFRN.

6.9.9. Example 9: Exosomes from Diverse Cell Lines Express IgV Family Members and Other Novel Surface Proteins Cell lines of different tissues of origin (HEK293SF, kidney; HT1080, connective tissue; K562, bone marrow; MDA-MB-231, breast; Raji, lymphoblast) were grown to logarithmic phase and transferred to media supplemented with exosome-depleted serum for ~6 days. Bone marrow-derived mesenchymal stem cells (MSC) were grown on 3D microcarriers for five days and supplemented in serum-free media for three day. Supernatant was isolated, and exosomes were purified using the Optiprep™ density-gradient ultracentrifugation method described above. Each of the purified exosomes was analyzed by LC-MS/MS as described above, the number of peptide spectrum matches (PSMs) for several exosome surface proteins was quantified (PTGFRN, IGSF8, IGSF3, BSG, SLC3A2, ITGB1, CD81, and CD9), and the results are provided in FIG. 31. The tetraspanins CD81 and CD9 were detectable in most purified exosome populations, but were, in some cases, equal to or lower than the other surface markers (e.g., compare CD9 to PTGFRN, BSG, and SLC3A2 in all cell lines). This finding indicates that the newly-identified surface markers, including the IgV protein family members are suitable targets for developing exosome affinity purification methods for several unrelated cell lines derived from different tissues.

6.9.10. Example 10: Generation of PTGFRN Knockout Cells and Exosomes

To generate PTGFRN knockout cells, HEK293 SF cells were transfected with recombinant Cas9 and guide RNAs targeting exon 2 and the transmembrane region of PTGFRN. The guide RNAs targeting exon2 generated by Thermo-Fisher included: (1) CGTTGGCAGTCCGCCTTAAC, CRISPR926045 CR (SEQ ID NO: 36); (2) CATAGTCACT-GACGTTGCAG, CRISPR926054 CR (SEQ ID NO: 37); (3) TTGTGGAGCTTGCAAGCACC, CRISPR926055 CR (SEQ ID NO: 38); and (4) GTTCTTTATGTGGAGCTCCA, CRISPR926071 CR (SEQ ID NO: 39). The guide RNAs targeting the transmembrane region generated by Thermo-Fisher included (1) TATCCCTTGCTGATCGGCGT, TMgRNA5.1.97 (SEQ ID NO: 40); (2) GCTGCAGTAC-CCGATGAGAC, TMgRNA3.7.87 (SEQ ID NO:41).

Targeted gene editing and deletion of the exon 2 and the transmembrane region of PTGFRN was confirmed by PCR and sequencing. Exosomes from five clonal PTGFRN knockout (PTGFRN KO) cell lines were purified as described above and analyzed by PAGE and Western blotting using the polyclonal rabbit antibody pools described in Example 8. As shown in FIG. 32B, bands corresponding to PTGFRN were not detected in any of the five knockout clones, demonstrating targeted deletion of PTGFRN in producer cells and purified exosomes. Importantly, exosome production yield and overall protein banding patterns (FIG. 32A) were not affected by PTGFRN deletion, indicating that PTGFRN KO exosomes can be used for experimental purposes.

To determine whether PTGFRN deletion altered the proteomic profile of purified exosomes, native exosomes and PTGFRN KO exosomes were analyzed by comparative mass spectrometry. As shown in FIG. 33, the protein content of the native and PTGFRN KO exosomes were very similar with the sole exception of PTGFRN, which was undetectable in the PTGFRN KO exosomes. The exosome markers Alix, CD81, TSG101, and CD9 were not significantly different between the groups. These data demonstrate that PTGFRN can be removed from exosomes without altering the proteomic profile of the exosomes.

To verify that PTGFRN deletion resulted in complete functional removal of PTGFRN and to demonstrate that the anti-PTGFRN (anti-CD315) antibody described in Example 7 is specific to PTGFRN, exosome binding experiments using BLI were carried out with native exosomes, PTGFRN overexpressing exosomes (PTGFRN++) and PTGFRN KO exosomes. Similar to the experimental results described in FIG. 27 and Example 7, PTGFRN++ exosomes bound to the immobilized anti-CD315 antibody with a greater affinity than native exosomes (FIG. 34). In contrast, an equal number of PTGFRN KO exosomes failed to bind to the immobilized antibody (FIG. 34), demonstrating that PTGFRN deletion ablates interaction of the PTGFRN KO exosomes with anti-PTGFRN affinity reagents.

6.9.11. Example 11: Exosomes can be Purified with Affinity Reagents Recognizing PTGFRN Custom monoclonal antibodies against PTGFRN were generated from the immunized rabbits as described in Example 8. To determine whether exosomes could be isolated by pulling PTGFRN, $5 \times 10^{10}$ native or PTGFRN KO exosomes were added to either magnetic Protein A beads (catalog #10001D; Invitrogen) or Protein A beads functionalized with 10 µg of a custom anti-PTGFRN monoclonal antibody. Each exosome-bead mixture was incubated for 30 minutes at room temperature and washed three times with PBS+0.1% v/v TWEEN® 20. Washed beads were eluted by incubating in elution buffer (20 mM glycine pH 3.6, 2× Laemmli sample buffer (catalog #1610737, Bio-Rad, Inc.), 10% β-mercaptoethanol) at 95° C. for 10 minutes and the boiled supernatant was analyzed by PAGE and anti-PTGFRN Western blotting using a different custom anti-PTGFRN monoclonal antibody. Total protein analyzed by PAGE showed a band corresponding to the molecular weight of PTGFRN only in the native exosome condition in the presence of the anti-PTGFRN antibody (FIG. 35A). This band was verified as PTGFRN by western blotting (FIG. 35B). HC and LC correspond to the heavy chain and light chain, respectively, of the anti-PTGFRN antibody used for purification. These data demonstrate that PTGFRN-containing exosomes can be purified from a solution by pulling PTGFRN on the exosome surface.

6.9.12. Example 12: Diverse Heterologous Proteins can be Fused to PTGFRN to Facilitate Overexpression on Exosomes Experimental data provided in FIGS. 11, 13, 14 and 15 demonstrates that several proteins can be dramatically overexpressed by using PTGFRN as an overexpression scaffold. The overexpression using PTGFRN was significantly better than expression using other exosome overexpression scaffolds. To determine the breadth of proteins that can be successfully overexpressed by being fused to PTGFRN, several engineered exosomes were generated. Factor VIII (FVIII) is a large enzyme involved in the coagulation cascade. A fragment of FVIII lacking the B Domain (BDD-FVIII) was fused to the N-terminus (externally facing side) of PTGFRN and expressed in HEK293 SF cells. Purified exosomes were analyzed by PAGE (FIG. 36A) and Western blot (FIG. 36B). A light chain of FVIII generated by processing of a full length FVIII in cell culture was readily detected in the engineered exosomes but not in the native exosomes using antibodies against FVIII (FIG. 36B; catalog #GMA-8025, Green Mountain Antibodies). A full-length FVIII has a molecular weight of 165 kDa, which is significantly larger than the molecular weight of PTGFRN (~120 kDa), demonstrating that very large proteins, including enzymes, can successfully be expressed as PTGFRN fusions on the surface of exosomes.

The PTGFRN fusion partners described above are all proteins with an ordered three-dimensional structure. XTEN® peptides (Amunix; Mountain View, Calif.) have long, disordered, repeated sequences with a dramatically increased apparent molecular mass compared to their primary sequence. A fusion construct encoding XTEN (a protein comprising randomized 288-amino acids which include 8% Ala, 12% Glu, 18% Gly, 17% Pro, 28% Ser and 17% Thr), a fragment of PTGFRN (SEQ ID NO: 33) and GFP was stably expressed in HEK293SF cells. Purified exosomes were isolated and analyzed by PAGE (FIG. 37A) and Western blotting (FIG. 37B). As shown in FIG. 37B, the C-terminal GFP of the fusion protein was detected by Western blotting, demonstrating in-frame translation of the fusion protein on the purified exosomes. These results demonstrate that unstructured proteins can also be stably expressed as fusions to PTGFRN. Furthermore, these results show that heterologous proteins can be simultaneously fused to the N- and C-termini of PTGFRN and result in intact proteins displayed on the exosome surface and lumen, respectively. Thus, PTGFRN is a robust scaffold that is amenable to protein fusions ranging in size from several amino acids (e.g., a FLAG tag) to over 150 kDa (BDDFVIII) of various structures and classes on either one or both of the N- or the C-termini.

6.9.13. Example 13: PTGFRN Sequences are Better at Expressing Heterologous Proteins on Exosomes than Other Exosomal Overexpression Systems The data in Example 3 and FIG. 15 demonstrate that PTGFRN is superior to other exosome scaffolds at expressing heterologous proteins in a bulk population of exosomes. These results cannot, however, differentiate between increased expression in a subset of exosomes versus a uniformly increased expression across all exosomes in a purified population. For the purposes of developing a uniform exosome therapeutic, it is preferred to have a homogenous exosomes population with uniformly increased expression rather than a heterogeneous exosome population including highly overexpressing exosomes and unmodified exosomes. To address this issue, we characterized individual exosomes in exosome populations on a particle-by-particle basis by nano-flow cytometry using the Flow NanoAnalyzer (NanoFCM, Inc.; Xiamen, China). The Flow NanoAnalyzer can measure light scattering and fluorescence emission of individual nanoparticles as small as 10 nm in diameter. Native exosomes and modified exosomes encoding luminal GFP fusions to CD9, CD81, or PTGFRN were isolated from stably transfected HEK293SF cells and purified by Optiprep® density gradient ultracentrifugation as described above. Analysis by Flow NanoAnalyzer set to excitation 488/emission 509 demonstrated that CD9-GFP exosomes were ~48% positive, CD81-GFP exosomes were ~80% positive, and PTGFRN-GFP exosomes were ~97% positive for GFP expression in the particle-by-particle analysis (FIG. 38, left). Furthermore, the mean fluorescence intensity (MFI) followed a similar trend, with PTGFRN-GFP exosomes being ~2-fold brighter than CD81-GFP exosomes overall (FIG. 38, right). These data demonstrate that exosomes modified to express PTGFRN-GFP fusion protein are a homogenous exosome population highly expressing the fusion protein, and the overall expression level was much higher than native or other modified exosomes expressing GFP fused to other exosome scaffolds.

The N-terminus of PTGFRN consists of a predicted signal peptide sequence (amino acids 1-21; SEQ ID NO: 8). To determine whether this sequence can enhance the expression of a transgene on purified exosomes, the PTGFRN signal peptide was compared to a signal peptide of a heterologous protein, DsbA11. HEK293 SF cells were stably transfected with expression constructs encoding (i) full length wild-type PTGFRN fused to GFP; (ii) a short fragment of PTGFRN (454-PTGFRN; SEQ ID NO: 33) containing the endogenous PTGFRN signal peptide fused to GFP; or (iii) a short fragment of PTGFRN (454-PTGFRN; SEQ ID NO: 33) having the endogenous PTGFRN signal peptide replaced with a signal peptide from the bacterial gene DsbA11 (Koerber et al., Journal of molecular biology, 427.2 (2015): 576-586), fused to GFP. As shown in FIG. 39, cells expressing GFP fusion protein containing full-length or truncated PTGFRN-GFP containing the endogenous PTGFRN signal peptide produced exosomes including GFP at similarly high levels. Cells expressing GFP fusion protein containing truncated PTGFRN with the DsbA11 signal peptide, however, produced exosomes expressing GFP at much lower levels. These results demonstrate that the PTGFRN signal peptide promotes high density decoration of engineered exosomes.

6.9.14. Example 14: Antibody Fragments can be Functionally Expressed on the Exosome Surface Using PTGFRN as a Scaffold Experimental data described above demonstrate that PTGFRN is a robust scaffold amenable to overexpression of many classes of proteins. Antibodies and antigen-binding fragments of antibodies are an important class of therapeutic peptides with diverse applications in many treating many diseases. To determine whether a functional antigen-binding fragment could be expressed on exosomes using PTGFRN as a scaffold, HEK29SF cells were stably transfected to overexpress a fusion protein consisting of a single chain Fab recognizing the lectin CLEC9A (clone 10B4, Millipore Sigma, catalog #04-148; and as described in Caminschi et al., Blood, 112: 8 (2008)), full-length PTGFRN, GFP, and a FLAG tag (FIG. 40A). Optiprep™ purified exosomes were run on a stain-free protein gel and blotted with an antibody against the FLAG tag showing significant overexpression of the full-length fusion protein (FIG. 40B).

The purified anti-CLEC9A exosomes were tested by BLI for binding to immobilized CLEC9A-Fc (R&D Systems, catalog #6049-CL-050; and as described in Uto et al., Nature Communications 7: 11273 (2016)). CLEC9A-Fc was bound to Protein A probes at a final concentration of 0.5 µg/ml in PBS+0.1% (v/v) Tween20, and incubated with $1 \times 10^{11}$ unmodified exosomes or exosomes modified to express the fusion protein consisting of a single chain Fab recognizing the lectin CLEC9A, a full-length PTGFRN, GFP, and a FLAG tag ("αCLEC9A-PTGFRN") shown in FIG. 40A. As shown in FIG. 41, only the anti-CLEC9A-PTGFRN exosomes bound to the CLEC9A-Fc probe, demonstrating functional recognition between a cell surface marker and exosomes engineered to overexpress an antigen-binding fragment.

6.9.15. Example 15: Mesenchymal Stem Cells Express PTGFRN

Therapeutic exosomes from several cell types have been used for research and clinical purposes. Stem cells of several varieties, including neural precursor stem cells and mesenchymal stem cells have been shown to have therapeutic benefit, but most studies using these cells rely on natural, unmodified exosomes. It would be desirable, therefore, to engineer these cell lines to overexpress specific ligands or other target proteins. Bone marrow-derived mesenchymal stem cells were grown in a 1.1 L microcarrier-based 3D bioreactor system. After five days of cell expansion, the growth media was discarded, and the cells were cultured for another three days in serum-free media. The serum-free media was filtered through a 100 µm filter to remove microcarriers and centrifuged at low speed to remove cell debris and contaminants. The clarified media was then purified by Optiprep™ density-gradient ultracentrifugation as described in Example 1. Purified exosomes from HEK293SF cells and MSCs were analyzed by Western blotting for PTGFRN, and the established exosome proteins ALIX, TSG101, CD63, CD9, and CD81. As shown in FIG. 42, all of these proteins were expressed in both HEK293 SF cells and MSCs, suggesting that the exosome proteins, e.g., PTGFRN, can be used as a scaffold for generating surface-engineered MSC exosomes.

6.9.16. Example 16: PTGFRN can be Overexpressed on Exosomes from Non-Human Cells The results in Examples 9 and 15 demonstrate that numerous human-derived cell naturally express PTGFRN and the other novel exosome proteins identified in Example 1. To determine whether PTGFRN can be used as a universal exosome scaffold protein, Chinese hamster ovary (CHO) cells were stably transfected with a plasmid expressing full-length PTGFRN fused to a FLAG tag ("the PTGFRN-FLAG plasmid"). Exosomes were purified from wild-type HEK293SF cells, HEK293SF cells transfected with the PTGFRN-FLAG plasmid, CHO cells, and CHO cells transfected with the PTGFRN-FLAG plasmid using the method described in Example 1. As shown in FIGS. 43A-C, PTGFRN-FLAG was successfully overexpressed in both HEK293 SF cells and CHO cells as detected by stain-free PAGE (FIG. 43A) and Western blotting with antibodies against PTGFRN (FIG. 43B) and FLAG (FIG. 43C). This result demonstrates that non-human cells (e.g., CHO cells) as well as human cells (e.g., HEK cells) can produce exosomes that overexpress human PTGFRN. This result indicates that PTGFRN is a universal scaffold protein for generating engineered exosomes from many different cell types and species.

6.9.17. Example 17: PTGFRN Provides Improved Loading of Luminal Cargo Compared to Conventional Exosome Proteins Previous examples demonstrated that PTGFRN overexpression results in exosomes with greater protein number and/or activity compared to conventional exosome proteins (e.g., Example 13; FIG. 15). Since PTGFRN is a transmembrane protein and has its N-terminus on the extravesicular face and its C-terminus in the exosome lumen, PTGFRN may be a suitable scaffold protein to load the lumen of exosomes with cargo proteins. To investigate this possibility, HEK293SF cells were engineered to stably express a bipartite reporter system that uses the small molecule rapamycin to facilitate protein-protein interactions. Either CD9 (FIG. 44A) or PTGFRN (FIG. 44B) were fused to GFP, a FLAG tag, and FKBP. The cells were also engineered to stably express mCherry fused to a V5 tag and FRB. In the presence of the small molecule Rapamycin, the proteins FRB and FKBP dimerize to form a stable complex. Culturing cells in the presence of Rapamycin therefore may allow for association between the mCherry cargo protein and either CD9 or PTGFRN during exosome biogenesis. Exosomes purified from these cells will be washed to remove Rapamycin, allowing for release of the mCherry as soluble cargo in the exosome lumen. (FIGS. 44A-B).

The CD9 loading reporter cells were grown in the presence of Rapamycin for 0, 1, or 2 days. The PTGFRN loading reporter cells were grown in the presence of Rapamycin for 5 days. Exosomes were purified from the cell cultures in the absence of Rapamycin allowing for cargo release in the exosome lumen. Purified exosome samples were run on a denaturing polyacrylamide gel and analyzed for the presence of total protein and Western blotting against the scaffold protein (anti-FLAG) or the mCherry cargo (anti-V5). The PTGFRN samples were loaded on the polyacrylamide gel with much less material compared to the CD9 samples, but PTGFRN was readily detectable by FLAG Western blotting. The cargo mCherry was also detected at a comparable level between the PTGFRN and CD9 scaffold samples (FIG. 45A). When the scaffold and cargo protein bands were measured by densitometry and normalized to the amount of collected exosomes, the PTGFRN scaffold was expressed at a higher level and was able to load much more mCherry cargo contained to the CD9 scaffold proteins (FIG. 45B). These data indicate that PTGFRN can be expressed as a fusion protein to a luminal loading peptide to a greater extent than the conventional exosome protein CD9, and that the use of PTGFRN results in greater directed cargo loading compared to the conventional exosome protein. These data indicate that complex, multi-part engineering systems can be used in the context of a PTGFRN scaffold and result in robust cargo loading in the exosome lumen.

6.9.18. Example 18: Generation of Modified Exosome Proteins

A polynucleotide encoding a modified exosome protein is generated using a polynucleotide encoding a whole exosome protein or a truncated exosome protein. A specific truncated exosome protein is selected by screening various truncated exosome proteins and selecting a truncated protein having optimal capabilities to incorporate into exosome membranes and interact with a binding agent. Targeting of the truncated proteins to exosome membranes is tested by nano-flow cytometry.

A polynucleotide encoding a modified exosome protein is generated by adding a polynucleotide encoding an affinity tag (glutathione-S-transferase, S-peptide, FLAG tag, GFP, etc.) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein. The polynucleotide is further modified to improve their targeting into exosome membranes and/or their affinity to a binding agent.

A different type of polynucleotide encoding a modified exosome protein is generated by adding a polynucleotide encoding a therapeutic peptide (e.g., an antibody, an enzyme, a ligand, a receptor, an antimicrobial peptide, a variant or a fragment thereof) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein presented on the surface of an exosome. The fusion protein maintains therapeutic activity of the therapeutic peptide.

A different type of polynucleotide encoding a modified exosome protein is generated by adding a polynucleotide encoding a targeting moiety (e.g., a targeting moiety specific to a specific organ, tissue or cell) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein presented on the surface of an exosome. The fusion protein allows the exosome to be targeted to a specific organ, tissue or cell.

Localization of modified exosome proteins on the exosome surface is also tested by nano flow cytometry.

6.9.19. Example 19: Generation of Surface-Engineered Exosomes

A producer cell generating surface-engineered exosomes is made by introducing an exogenous sequence encoding an exosome protein or a variant or a fragment of the exosome protein. A plasmid encoding an exosome protein is transiently transfected to induce high-level expression of the exosome protein on the exosome surface. A plasmid encoding a modified exosome protein is transiently transfected to produce exosomes having the modified exosome protein on the surface.

A polynucleotide encoding an exosome protein, a variant or a fragment of an exosome protein, or an exogenous sequence encoding an affinity tag, a therapeutic peptide or a targeting moiety is stably transformed into a producer cell to produce surface-engineered exosomes. The exogenous sequence encoding an affinity tag, a therapeutic peptide or a targeting moiety is inserted into a genomic site encoding an exosome protein to generate a fusion protein comprising the affinity tag attached to the exosome protein. A polynucleotide encoding a modified exosome protein is knocked in to a genomic site encoding an exosome protein.

A producer cell line is generated by stably transfecting at least two polynucleotides, each encoding an exosome protein, a variant or a fragment of an exosome protein, or an exogenous peptide (e.g., affinity tag, targeting moiety, therapeutic peptide). A different producer cell line is also generated by inserting two or more exogenous sequences (e.g., exogenous sequences encoding an affinity tag, a marker, a targeting peptide, a therapeutic peptide, etc.) into multiple genomic sites, within or in a close proximity to the genomic sequence encoding an exosome protein, to generate a surface-engineered exosome comprising multiple modified exosome proteins. Each of the plurality of modified exosome proteins is targeted to the surface of exosomes. The exosomes have affinities to two different binding agents and are purified by either or both of the binding agents.

6.9.20. Example 20: Isolation, Purification and Sub-Fractionation of Exosomes by Affinity Purification Binding agents for affinity purification of exosomes are developed by biopanning/directed evolution that elute under mild conditions.

The binding agent is attached to a solid support (e.g., a porous agarose bead) and formed into a conventional chromatography system (e.g., GE AKTA). A sample containing exosomes is applied to the column for affinity purification

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

The present disclosure provides, inter alia, compositions of cannabinoid and entourage compositions. The present disclosure also provides method of treating neurodegenerative diseases by administering the cannabinoid and entourage compositions. While various specific embodiments have been illustrated and described, the above specification is not restrictive. It will be appreciated that various changes can be made without departing from the spirit and scope of the invention(s). Many variations will become apparent to those skilled in the art upon review of this specification.

---

What is claimed is:

1. A pharmaceutical composition comprising:
   a. an exosome comprising a scaffold protein which comprises Prostaglandin F2 Receptor Negative Regulator (PTGFRN) or a functional fragment thereof, wherein the scaffold protein is present at a density that is higher than the density of the scaffold protein in a native exosome, and:
   b. an excipient.

2. The pharmaceutical composition of claim 1, wherein the scaffold protein comprises the amino acid sequence as set forth in SEQ ID NO: 1 without the PTGFRN signal peptide.

3. The pharmaceutical composition of claim 1, wherein the scaffold protein comprises the amino acid sequence as set forth in SEQ ID NO: 33.

4. The pharmaceutical composition of claim 1, wherein the exosome further comprises a therapeutic protein.

5. The pharmaceutical composition of claim 1, wherein the density of the scaffold protein is 2-fold to 1000-fold higher than the density of the scaffold protein in a native exosome.

6. The pharmaceutical composition of claim 5, wherein the exosome further comprises a targeting moiety.

7. The pharmaceutical composition of claim 6, wherein the targeting moiety is specific to an organ, a tissue, or a cell.

8. The pharmaceutical composition of claim 1, wherein the density of the scaffold protein is 32-fold to 400-fold higher than the density of the scaffold protein in a native exosome.

9. The pharmaceutical composition of claim 1, wherein the density of the scaffold protein is 100-fold to 200-fold higher than the density of the scaffold protein in a native exosome.

10. The pharmaceutical composition of claim 4, wherein the therapeutic protein is selected from the group consisting of:
    (a) an antibody or an antigen-binding fragment thereof,
    (b) an enzyme or a functional fragment thereof
    (c) a ligand or a functional fragment thereof,
    (d) a receptor or a functional fragment,
    (e) an antimicrobial peptide or a functional fragment,
    (f) a functional fragment of any of (a)-(e), or
    (g) any combination of (a)-(f).

11. The pharmaceutical composition of claim 4, wherein the therapeutic protein is fused to the scaffold protein.

12. The pharmaceutical composition of claim 1, wherein the exosome further comprises atherapeutic compound.

13. The pharmaceutical composition of claim 12, wherein the therapeutic compound is selected from the group consisting of a nucleotide, an amino acid, a lipid, a carbohydrate, a small molecule, and any combination thereof.

14. The pharmaceutical composition of claim 12, wherein the therapeutic compound is conjugated to the scaffold protein.

15. The pharmaceutical composition of claim 1, wherein the composition is substantially free of contaminating proteins.

* * * * *